(12) United States Patent
Hofmeister et al.

(10) Patent No.: US 10,876,095 B1
(45) Date of Patent: Dec. 29, 2020

(54) BIOMIMETIC LAMELLAR TISSUE SCAFFOLDS

(71) Applicant: Ultra Small Fibers, LLC, Wartrace, TN (US)

(72) Inventors: William Hudson Hofmeister, Nashville, TN (US); Robert A. Van Wyk, St. Petersburg, FL (US); Christopher P. Dougherty, Rogers, AR (US); Collin David Anderson, Chicago, IL (US)

(73) Assignee: ULTRA SMALL FIBERS, LLC, Wartrace, TN (US)

( * ) Notice: Subject to any disclaimer, the term of this patent is extended or adjusted under 35 U.S.C. 154(b) by 0 days.

(21) Appl. No.: 16/777,762

(22) Filed: Jan. 30, 2020

Related U.S. Application Data

(63) Continuation of application No. 16/210,210, filed on Dec. 5, 2018, now abandoned.

(51) Int. Cl.
| | |
|---|---|
| *A61L 27/14* | (2006.01) |
| *A61L 27/58* | (2006.01) |
| *C12N 5/0775* | (2010.01) |
| *A61L 27/22* | (2006.01) |
| *A61F 2/02* | (2006.01) |
| *A61L 15/32* | (2006.01) |
| *A61K 38/39* | (2006.01) |
| *A61L 15/58* | (2006.01) |
| *A61L 27/54* | (2006.01) |
| *A61L 15/22* | (2006.01) |

(Continued)

(52) U.S. Cl.
CPC ............ *C12N 5/0667* (2013.01); *A61F 2/02* (2013.01); *A61K 38/39* (2013.01); *A61L 15/225* (2013.01); *A61L 15/32* (2013.01); *A61L 15/44* (2013.01); *A61L 15/58* (2013.01); *A61L 27/225* (2013.01); *A61L 27/54* (2013.01); *A61F 2002/30766* (2013.01); *A61L 2300/412* (2013.01); *B82Y 5/00* (2013.01)

(58) Field of Classification Search
None
See application file for complete search history.

(56) References Cited

U.S. PATENT DOCUMENTS

| | | |
|---|---|---|
| 2006/0229735 A1 | 10/2006 | Roy et al. |
| 2010/0129908 A1 | 5/2010 | Fang et al. |

(Continued)

OTHER PUBLICATIONS

White et al., "Single-pulse ultrafast-laser machining of high aspect nanoholes at the surface of SiO2," Optics Express, vol. 16, No. 19, p. 14411-14420 (2008).

*Primary Examiner* — Kevin S Orwig
(74) *Attorney, Agent, or Firm* — Eric B. Fugett; Mark A. Pitchford; Pitchford Fugett, PLLC

(57) ABSTRACT

A biomimetic lamellar tissue scaffold for tissue regeneration comprises a plurality of lamellae formed of a polymer film and each having a first surface and a second surface. A patterned array of polymer nanofibers protrudes from the first surface of each lamella of the plurality. The lamellae form a plurality of interlamellar spaces between the first and second surfaces of adjacent lamellae. Protuberances formed on the first surface of each lamella maintain the interlamellar spaces. The arrays of polymer nanofibers on the first lamellar surface of each lamella protrude into the interlamellar spaces between adjacent lamellae and are configured to influence the propagation and differentiation of cells populated to or recruited to the scaffold.

20 Claims, 47 Drawing Sheets

(51) Int. Cl.
*A61L 15/44* (2006.01)
*B82Y 5/00* (2011.01)
*A61F 2/30* (2006.01)

(56) References Cited

U.S. PATENT DOCUMENTS

| | | |
|---|---|---|
| 2013/0216779 A1 | 8/2013 | Hofmeister et al. |
| 2015/0004692 A1 | 1/2015 | Le Berre et al. |
| 2016/0222345 A1 | 8/2016 | Hofmeister et al. |
| 2017/0072349 A1 | 3/2017 | Hofmeister et al. |
| 2017/0320057 A1 | 11/2017 | Hofmeister et al. |

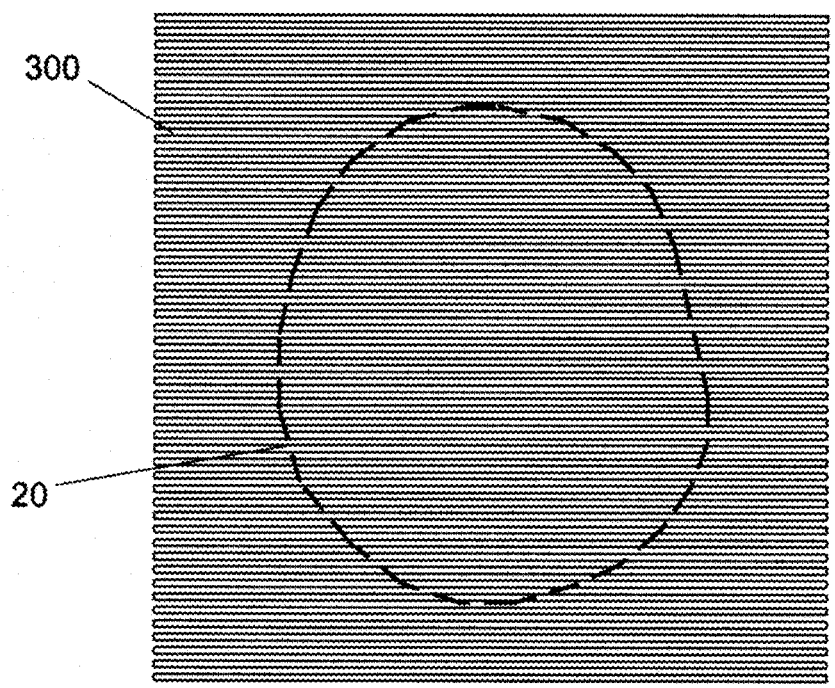
Fig. 19
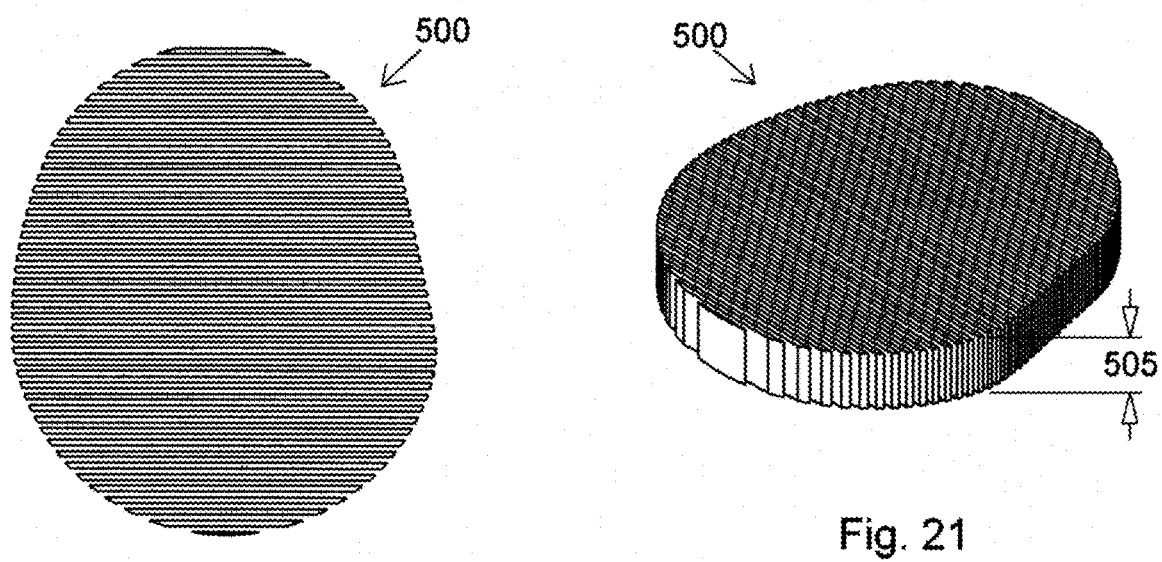
Fig. 20
Fig. 21

10,876,095 B1

BIOMIMETIC LAMELLAR TISSUE SCAFFOLDS

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

CROSS-REFERENCES TO RELATED APPLICATIONS

Not Applicable.

STATEMENT REGARDING FEDERALLY SPONSORED RESEARCH OR DEVELOPMENT

Not Applicable

REFERENCE TO SEQUENCE LISTING OR COMPUTER PROGRAM LISTING APPENDIX

Not Applicable

BACKGROUND OF THE INVENTION

Stem Cells and the Extracellular Matrix

The use of stem cells for regenerative treatment of injuries is now commonplace. Stem cells from bone marrow aspirate or other sources are frequently injected into knees as a treatment for arthritis. While these injections may be beneficial for many conditions, their regenerative abilities are limited because they lack a physiologically structured extracellular matrix ("ECM"). This matrix surrounds cells and provides support and organization that allows the creation of organs and other tissue structures.

The ECM is more than a structural support network. The ECM is a highly complex structure that heavily influences the behavior of cells within the matrix. Cells respond to external signals received from the matrix, and provide signals to the matrix that cause the matrix to beneficially adapt. Cells bind to features of the ECM and significant chemical and mechanical signaling occurs between the ECM and the cell. In "outside-in" signaling, physical cues play a significant and, until recently, underappreciated role in cell fate. For stem cells, particularly human mesenchymal stem cells ("hMSCs"), these signals heavily influence the decision to either maintain their stem cell phenotype or differentiate towards a specified cell lineage.

Scaffolds of various types have been devised that function as a temporary substitute for the ECM so as to enable the regeneration of complex tissue structures. These scaffolds may have a variety of configurations and be formed of a wide range of bioabsorbable materials. Flexible scaffolds may be used for various applications including the reinforcement, support and augmentation of soft tissue.

The biomaterials community has been reorienting their design process towards generating an optimal scaffold that can reliably and reproducibly mimic the extracellular matrix, one of the primary environmental constituents that heavily influence cell fate.

The need for tissue scaffolds is evidenced by the number of patent applications filed wherein the subject is a tissue scaffold. The subject inventions are focused on creating constructs that temporarily perform the functions of an extracellular matrix. These applications address a myriad of ways of providing a structure to support cells and providing channels for their propagation. These inventions also address numerous ways of controlling aspects of the behavior of stem cells—their propagation, maintaining their "sternness", and their differentiation into desired cell types. Of interest herein are primarily scaffolds of lamellar construction.

Gingras in U.S. Pat. No. 9,642,943 describes a tissue scaffold with a lamellar structure with lamellae parallel to the basal plane of the scaffold. The lamellae have a plurality of perforations ("pores") of varying sizes, shapes and orientations such that intersecting perforations in adjacent lamellae form irregular passages through which cells may propagate. By varying the size, orientation and spacing of the perforations, passages may be formed that have varying pore sizes determined by the degree of overlap in the pores on adjacent lamellae. Scaffolds so formed may have stratified properties intended to favor the growth of stratified tissue structures that approximate that of native tissue. Optionally these scaffolds may have passage surfaces containing or coated with adhesion ligands "to facilitate integrin-dependent migration of cells, such as fibroblasts and endothelial cells, to and into the scaffolds." Though the channels formed by intersecting lamellar perforations follow an irregular path these channels are substantially normal to the plane of the scaffold. There are no interlamellar spaces in the Gingras scaffolds.

Nobosky et al. in U.S. Pat. No. 8,724,203 and Kolewe et al., in US 2014/0243995 also describe scaffolds with lamellar constructions. As with Gingris, passages are formed by perforations in the lamellae and the cellular propagation is normal to the basal plane of the scaffold. While the shape of the perforations in the lamellae vary in configuration and distribution, the pore size in the passages is determined by the relative positioning and overlap of the perforations in adjacent lamellae. Through the choice of size and position of the perforations on the lamellae and relative position of the perforations on adjacent lamellae, portions of the scaffold may be configured to achieve desired outcomes in cellular development through the control of pore size. In this manner stratified tissue structures may be created. The scaffold constructs described do not have interlamellar spaces and cell propagation and fluid flow parallel to the plane of the lamellae is precluded.

In US 2003/0012805 Chen et al. describe scaffolds formed of a composite material, the composite having a lamellar construction useful for an implant for cartilage tissue regeneration. The composite material has alternating layers of "porous structure of naturally occurring polymer" and "mesh of bioabsorbable synthetic polymer". As described, the combination has a "high mechanical strength" so that collapse of the scaffold due to the application of a compressive load is prevented. The lamellae forming the scaffold are oriented perpendicular to the basal plane of the scaffold and may have either a "stacked" parallel arrangement or may be coiled with the coil axis normal to the basal plane of the scaffold. Propagation through the matrix is parallel to the plane of the lamellae. There are no interlamellar spaces within the scaffold, and the scaffold is formed of two dissimilar materials.

Articular Lesions

Hereafter, scaffolds for the treatment of lesions formed in articular surfaces will be considered. The treatment of these defects requires a scaffold that supports stem cells as they refill the lesion with fibrocartilage or hyaline-like cartilage.

Chondral and osteochondral lesions may lead to the development of osteoarthritis with the resulting impacts on the patient's quality of life. The incidence of these lesions is increasing due to a greater emphasis on physical activity and the effects of an aging population. Accordingly, there is an emphasis on the development of methods of treatment to reduce the associated joint pain and restore quality of life to patients.

Articular cartilage cells are embedded in an extracellular matrix of collagen fibers and proteoglycans. Articular cartilage cells are dependent on diffusion for the supply of oxygen and nutrients since the structure contains no blood vessels. Accordingly, its ability to heal is very limited.

Articular cartilage has a complex stratified structure that has a virtually frictionless surface and has resiliently compressive underlying structures that prevent injury due to impacts to the articular surface. Strategies for treating chondral and osteochondral lesions are focused on creating conditions that allow stem cells to recreate this complex cartilage structure.

One such technique, commonly referred to as microfracture, is a bone marrow stimulation technique. After removing calcified cartilage from the bottom of the lesion so as to expose healthy bone, and creating stable walls of healthy cartilage at the margins of the lesion, small diameter holes are punched or drilled in the bone surface to a depth sufficient to reach the underlying marrow. This allows stem cells to migrate through the passages created to the fibrin clot of the defect, creating an ECM during healing. The fibrocartilage created by this healing process ideally completely fills the defect. In practice, the microfracture procedure typically does not completely fill defects to depths greater than about, two millimeters. Additionally, properties of the fibrocartilage formed are significantly inferior to the original and surrounding hyaline cartilage.

Current methods for treating chondral and osteochondral lesions are focused on creating hyaline-like cartilage through the use of scaffolds that are used to temporarily create a structure that mimics the cartilage architecture and supports cell growth. The scaffold forms range from suspensions of particles in an autologous solution that can be introduced to the defect by flow like BioCartilage by Arthrex, Inc. (Naples, Fla.) to the fibrous scaffolds like the Hyalofast made by Anika Therapeutics (Bedford, Mass.).

The BioCartilage product contains articular cartilage extracellular matrix with type II collagen and proteoglycans. A standard microfracture treatment is first completed. Thereafter, the BioCartilage material is mixed with an autologous blood solution, the mixture is introduced into the defect, and the surface is subsequently sealed with a fibrin glue. It is specified by the manufacturer that the defect not be completely filled, and that space be left for the fibrin glue. The BioCartilage material provides a scaffold for the marrow elements from the microfracture holes. While flowable scaffolds may provide some benefits over the standard microfracture method, scaffolds of this type are not able to support a compressive load. The body does not allocate resources to soft tissue that is not stressed (Davis' Law). Accordingly, because the cartilage being formed is not stressed, the body may not provide it with the proper determinates of cell fate required to create hyaline cartilage. Generally, only fibrocartilage is created and the defect is not completely filled.

Typical in form to other non-woven mat-type scaffolds, the HyaloFast product is composed of a single 3D fibrous layer of HYAFF®, a benzyl ester of hyaluronic acid. The implant is soft, may be cut to size and shape, and conforms to the shape of the lesion. It may be layered if required to completely fill the lesion. The scaffold may be used as a supplement to microfracture like the BioCartilage scaffold material, or in combination with bone marrow aspirate. According to the manufacturer, mesenchymal stem cells differentiate into chondrocytes for cartilage regeneration and osteocytes for subchondral bone formation. Because the scaffold is made of a soft compressible material, it cannot be load bearing. Accordingly, pressure applied to the construct will result in compression of the matrix so that the exposed surface does not match the contour of the surrounding articular surface and the fill is incomplete. The soft compressible nature of the scaffold also prevents the application of controlled compressive force to the scaffold and the developing tissue within it. As a result, no shear stress is applied to the developing tissue, and, because this shear stress is absent, the growth of true hyaline cartilage is not promoted.

Other scaffolds for treating chondral and osteochondral lesions do not have a uniform density and/or material throughout their thickness. With the intention to create in the regenerated tissue a stratified structure that mimics articular cartilage, some scaffolds have a layered construction, the layers having characteristics to produce osteocytes for subchondral bone, and chondrocytes for the middle and superficial zones. An example of a scaffold of this type is the MaioRegen product by FinCeramica (Faenza RA, Italy). Like the HyaloFast product previously described, the MaioRegen is formed of fibers in a non-woven mat. The scaffold has a "subchondral" layer formed of 30% equine collagen and 70% magnesium-enriched hydroxyapatite (Mg-HA), a "tide mark" middle layer formed of 60% equine collagen and 40% Mg-HA, and an outer "collagen layer" formed of 100% equine collagen. The "subchondral" layer simulates the subchondral bone layer; the top layer resembles cartilaginous tissue, and the middle layer simulates the "tide mark" region in which the transition between the top and bottom regions occurs. As the mesenchymal stem cells entering the MaioRegen scaffold from the subchondral bone propagate upward through the scaffold, differentiation into osteocytes and chondrocytes is controlled by signaling from the compositional characteristics of the layers. Because the scaffold has a non-woven mat structure, it does not have appreciable compressive strength and will permanently deform under load, with the associated deleterious effects. As with the previously described prior art scaffolds, the soft compressible nature of this scaffold prevents the application of controlled compressive force to the scaffold and the developing tissue within it. As a result, no shear stress is applied to the developing tissue, and, because this shear stress is absent, the growth of true hyaline cartilage is not promoted.

Scaffolds are formed of bioabsorbable materials, the structure being replaced by extracellular matrix as the scaffold degrades after having performed its function.

The propagation and differentiation of stem cells is affected by the geometric characteristics of a scaffold. In the case of fibrous scaffolds, the diameter of the fibers may affect the ability of the stem cells to attach to the fibers. The pore size and composition also affect stem cell behavior. For instance, native bone has a porosity of between fifty and ninety percent with an average pore size typically in the one millimeter range. Providing a scaffold with similar pore density and size favors the growth of osteocytes and vascularization. Smaller pores favor chondrocyte growth. Accordingly, there is an emphasis on manufacturing methods for scaffolds that allow control of the fiber diameter and density to achieve desired effects. The fabrication of polymer filaments on the scale of fibrous ECM elements (2-200 nm) is accomplished by electrospinning. The electrospinning process forms long fibers of polymer solvent solution which are extruded at high (>10 kV) potential to a collector base plate that is traversed at a predetermined rate to form layers of fiber mat. The orientation of these long fibers is substantially random within planes parallel to the plane of the base plate. By controlling the parameters of the electrospinning process and movement of the collector, fiber size and density may be optimized for a given application. Other scaffolds, not generally commercially available at this time, may be formed as a porous foam with controlled pore size and pore density. And researchers are also working on methods in which additional pores are created in a formed scaffold by laser drilling, or in which scaffolds are manufactured by 3D printing.

It should be understood that, while in some discussions of fibrous scaffolds the term "pore" is used, a "pore" is defined as "a minute opening in a surface". Scaffolds formed of fibrous mats do not have the requisite surfaces to have actual pores. The fiber diameter, density and average inter-fiber spacing of the fibers in a fibrous scaffold may be adjusted to favor a preferred cell behavior through control of the average cross-sectional area of the highly irregular channels for cell propagation. This may be considered an effective pore size.

Scaffolds with optimized fiber size, and effective pore size and density designed to achieve a desired effect on the propagation and differentiation of stem cells are broadly referred to as "tuned" scaffolds. Additionally, the term "tuned" may be applied to fibrous scaffolds in which the direction of the elongate continuous fibers have a preferred range of orientation in planes parallel to the basal plane of the scaffold. These "tuned" scaffolds may also have two or more discrete regions in which the porosity characteristics of each region are optimized to favor the differentiation of stem cells to favor, for example, osteocytes and chondrocytes. Frequently, scaffolds with these discrete regions with differing characteristics are also referred to as "biomimetic", that is mimicking a naturally occurring structure that favors stem cell propagation and differentiation to form structures within the body. In the case of scaffolds for treating osteochondral lesions, a scaffold that has at least a first portion with fiber diameter and fiber densities that mimic those of native bone, and a second portion with fiber diameter and densities that mimic those of the cartilaginous extracellular matrix would be considered biomimetic under the commonly used definition.

However, it must be noted that the fiber length in these "tuned" fibrous scaffolds is not controlled and therefore cannot be optimized for a given use. And the fiber orientation is only controlled within a broad range, and then only in planes parallel to the basal plane of the scaffold. The control of fiber orientation is not sufficient to allow optimization except within a very broad range, and fiber orientations other than substantially parallel to the basal plane are impossible. While these scaffolds may be referred to as tuned, they are only optimized for parameters that can be controlled in the manufacturing process. Indeed, the average density and effective pore size can only be controlled within broad ranges. Advantages that may be achieved through control of the length, orientation, and three-dimensional arrangement of fibers cannot be realized with current commonly used manufacturing techniques. Naturally occurring structures within the body are not limited in the way that these manufactured scaffolds are limited. Accordingly, while the manufactured scaffolds may be referred to as "biomimetic" in that they grossly mimic natural structures, the development of advanced manufacturing methods that allow improved control of additional fiber characteristics and the three-dimensional arrangement of these fibers will enable the creation of scaffolds that achieve enhanced results through their ability to more closely approximate naturally occurring structures of the ECM.

Accordingly, what is needed are improvements in tissue scaffolds and methods for treating patients using same.

BRIEF SUMMARY

The presently disclosed subject matter overcomes some or all of the above-identified deficiencies of the prior art, as will become evident to those of ordinary skill in the art after a study of the information provided in this document.

Scaffolds with enhanced biomimetic features formed using advanced manufacturing methods are the subject of the instant invention, along with methods for their use. Specifically, scaffolds of the present invention have patterned matrices of nanofibers that are spaced on the micron scale formed on elements of the scaffold, the nanofibers being similar in size and morphology to collagen fibrils universally found within mammalian cells. This biomimetic aspect of these scaffolds is enabled by an advanced manufacturing method and imparts beneficial properties unachievable in other, less biomimetic scaffolds.

In healthy, naturally occurring tissue the extracellular matrix is formed of many types of collagen. More specifically, the basement membrane is formed of highly cross-linked collagen IV, which is quite stiff, while Type II collagen fibrils constitute the bulk of hyaline cartilage. Type II collagen fibrils are flexible and are the primary conduits for chemokine and proteoglycan communication between cells. Focal adhesions formed by stem cells on Type II fibrils affect the behavior of stem cells through "outside in" signaling. One specific mechanical aspect of this is communication from the collagen forming the ECM to a stem cell is through the tendrils attached to a stiff matrix. Another is through the creation of shear stresses between the cell and the ECM. To create shear stress at the focal adhesions the tendrils must have not only sufficient strength but a degree of rigidity. Here we come to the most overlooked aspect of biomimetic scaffolds. Many flexible Type II fibrils are anchored to and protrude from a stiff basement membrane. This stiffness gradient in Type II collagen is sensed by the cell and is a primary driver in cell mobility and an important cue in determining cell fate.

It will be understood that prior art scaffolds, while claiming to be "biomimetic" lack the fine complex features of the extracellular matrix that control cell adhesion, propagation and differentiation in the natural structure.

Scaffolds of the present invention mimic the tendril arrays present on the basement membrane of cross-linked collagen forming the ECM. This is accomplished by providing arrays of nanofibers formed on surfaces of the scaffold, the nanofibers of an array having a spacing similar to the collagen tendril attachment to a stiffer matrix of cross-linked fibers, and, like the tendrils, the nanofibers are substantially normal to the surface at the attachment site. The nanofibers may have somewhat irregular shapes in that they may have bumps, ridges, seams, and portions with asymmetric cross sections, however the nanofibers are generally tapered with a distally decreasing cross-section over their length. Each nanofiber may be viewed as a cantilevered beam with decreasing stiffness along its length, the greatest stiffness being adjacent to its attachment point to the surface. This allows secure attachment by cells through focal adhesions formed at the tips of the nanofibers, and also allows the creation of shear stresses between the scaffold and cells attached thereto. Additionally, nanofiber arrays of the present invention may provide outside-in signaling to cells within the scaffold that determine, for instance, the tendency of stem cells to maintain their "sternness" or to differentiate, and, in the case of differentiation, to increase the proclivity of the cells to differentiate to a preferred cell type.

Disclosed herein are weight-bearing, biomimetic tissue scaffolds having a lamellar structure. Scaffolds of the present invention are formed of a plurality of lamellae on which are integrally formed nanofibers patterned on the micron scale over expanses of surfaces of the lamellae. Unlike the fibers of prior art scaffolds previously herein described, nanofibers of the present invention have a predetermined length and are oriented substantially normal to the basal plane of the lamella. The fibers are generally tapered over their length so that the stiffest part of the fiber is adjacent to its attachment to the surface of the lamella. The fibers are arranged in ordered arrays (matrices) in which the nanofibers may be arranged in rows, the spacing of the nanofibers within a row and the spacing between rows being regular or irregular and predetermined by the manufacturing method used. Lamellae of the present invention have an elongate planar base formed of a film of a suitable bioabsorbable material, with nanofiber arrays formed on a first surface thereof. To construct a scaffold of the present invention, lamellae are arranged in a substantially parallel configuration with the first surface of each lamella adjacent to the second surface of its adjacent lamella. In addition to the nanofiber arrays, on the first side of each lamella, structural elements are formed that maintain the spacing between adjacent lamellae to create an interlamellar space. The lamellae may also contain perforations to allow the flow of materials and the propagation of cells through a lamella between adjacent interlamellar spaces.

In some embodiments of the present invention the lamellae are oriented perpendicularly to the basal plane 5 of the scaffold so that the propagation of stem cells is from the basal plane 5 of the scaffold outward or upward, away from the exposed bone, through spaces formed between adjacent lamellae of the scaffold. In use, for instance, when implanted into a defect, the basal plane 5 of the scaffold is parallel with the basal plane of the defect and the lamellae perpendicular to the basal plane of the defect. When placed on a tissue surface, the basal plane 5 of the scaffold is parallel to the tissue on which it is placed. In these embodiments, stem cells align perpendicular to the basal plane 5 of the scaffold. The portion of the construct bounded by adjacent rows of nanofibers, the first surface of the lamella on which the fibers are formed, and the second surface of the adjacent lamella forms a virtual pipeline through which cells may propagate during tissue regeneration, and through which fluids, nutrients, chemokines, etc. can easily be conveyed to the entire depth of the regenerating tissue. The spacing between rows of nanofibers, and also the spacing of nanofibers within a row may be chosen (tuned) to favor the propagation of stem cells while maintaining their "sternness" or to favor their differentiation into cells of a predetermined type. In some embodiments the pattern and physical characteristics of nanofibers on a lamella may be uniform over the entire first surface of the lamella. In other embodiments a lamella may have two or more regions with each region having its own spacing of nanofibers within its rows and/or between its rows of nanofibers, and nanofibers each with unique height, diameter and profile characteristics. In this manner, scaffolds may be created with discrete zones, each of which is optimized for the propagation and/or differentiation of a selected cell type. For instance, in a scaffold optimized for regenerating tissue in an osteochondral lesion, a first zone adjacent to the basal plane basal plane 5 of the scaffold may have nanofiber and row spacings that favor the transformation of stem cells into osteocytes, a second zone near the chondral surface may have a nanofiber matrix that favors the formation of chondrocytes, and a third zone that forms a transition between the first and second zones, the nanofiber matrix of this third zone being optimized for this purpose.

A preferred method for manufacturing lamellae with tuned nanofiber arrays for scaffolds of the present invention is hot pressing, a method in which a suitable polymeric film is positioned between a planar heating plate and a silica substrate/mold in which patterns of nanoholes have been formed, the pattern of the nanoholes being complementary to the pattern of nanofibers to be produced. The heater plate, silica mold and film are heated to a predetermined temperature and a force is applied to the heater plate so as to press the film against the silica mold. When the temperature of the film material reaches a sufficient level, the softened film material flows into the nanoholes in the mold. In some embodiments with certain materials the softened polymer infiltrates the nanoholes due to surface tension effects only. In other embodiments with films formed of the same or different materials, infiltration of the nanoholes is accomplished by a combination of hydrostatic pressure and surface tension. Thereafter the system is cooled sufficiently to allow the film to be peeled off of the substrate with the molded nanofibers attached to its first surface. Optionally, the structural features for maintaining the space between adjacent lamellae may be simultaneously formed by the same method. The hot-pressing method for producing tissue growth substrates with nanofiber arrays is described in detail by Hofmeister, et al. in US 2016/0222345, herein incorporated by reference. While hot pressing is a preferred method for forming lamellae for scaffolds of the present invention, solution casting may also be used. The solution casting method for producing tissue growth substrates with nanofiber arrays is described in detail by Hofmeister, et al. in US 2015/0093550. Any alternate method capable of producing integral arrays of nanofibers of predetermined lengths, diameters, and profiles perpendicular to a first surface of a film, and wherein the spatial arrangement of the fibers has a predetermined pattern may be used. All scaffolds formed of lamellae with nanofiber features configured as previously described fall within the scope of this invention regardless of the manufacturing method used to produce the lamellae.

Lamellar scaffolds of the present invention, wherein the lamellae are perpendicular to the basal plane of the scaffold, may have any configuration in which the nanofiber arrays formed on the first surface of a first lamella protrude into the interlamellar space created between that first surface of a first lamella and the second surface of an adjacent second lamella, the space being maintained by structural features protruding from the first surface of the first lamella. In some embodiments a plurality of lamellae are stacked together in the manner of a deck of cards perpendicular to the basal plane. In other embodiments, one or more elongate lamellae are wound into a planar spiral winding, the axis of the winding being normal to the basal plane of the scaffold. Other configurations for lamellar scaffolds of the present invention are anticipated. All fall within the scope of this invention.

Unlike prior art scaffolds previously described herein, lamellar scaffolds of the present invention in which the lamellae are perpendicular to the basal plane 5 of the scaffold have a load bearing capability. These scaffolds have a resilient compressive strength due to the construct in which the lamellae are parallel and closely adjacent with the space between lamellae being filled with fluids and cells. This arrangement prevents buckling of the lamellae when loaded on their edges, with additional compressive strength supplied by hydrostatic and hydrodynamic effects due to the fluids and cells filling the interlamellar spaces. Indeed, the response to a compressive load applied to these lamellar scaffolds is rate dependent largely due to these hydrostatic and hydrodynamic effects. When a scaffold is placed in an osteochondral lesion for the purpose of regenerating tissue therein, the repetitive loading caused by walking and other activities causes resilient (transient) compression of the scaffold. This resilient repetitive compression enhances the flow of viscous elements within the scaffold. This effect, along with shear stresses applied to cells growing in the scaffold, beneficially enhances cell development and the adhesion of cells to the scaffold. Additionally, scaffolds that have a rigidity comparable to that of the native tissue tend to favor the differentiation of stem cells into that type of tissue. In certain embodiments in which enhanced compressive strength is desirable, additional lamella of a more rigid material, or with a heavier cross-section may be added to the scaffold. These supplementary lamellae provide structural strength only, do not have nanofiber arrays formed on their surfaces, and do not participate in the regeneration process.

In other embodiments of the present invention, lamellar scaffolds are formed in which the plane of the lamellae is parallel to the basal plane of the scaffold, the lamellae being stacked parallel to the basal plane. Lamellae for these embodiments, like those for scaffolds with lamellae perpendicular to the basal plane of the scaffold, have formed on a first lamellar surface an engineered array of rows of nanofibers and perforations through the lamellae. In previously described scaffolds with lamellae oriented perpendicular to the basal plane of the scaffold, cells propagate in a substantially linear path, normal to the basal plane, directed by rows of nanofibers and the lamellar surfaces. In scaffolds of the present invention with lamellae oriented parallel to the basal plane of the scaffold, cell propagation away from the basal plane occurs in a labyrinth formed by the rows of nanofibers, surfaces of adjacent lamellae, and holes formed in the lamellae, the holes allowing propagation to proceed from one inter-lamellar space to the next inter-lamellar space. In the same manner as previous embodiments, spacing between rows of nanofibers, and also the spacing of nanofibers within a row may be chosen (tuned) to favor the propagation of stem cells while maintaining their "stemness" or to favor their differentiation into cells of a predetermined type. In some embodiments of the present invention the lamellae forming the scaffold have a uniform configuration throughout. In others the stack of lamellae forming the scaffold may have discreet portions of multiple lamellae with the lamellae in each portion having arrays of nanofibers tuned for the propagation or differentiation of specific cell types. For instance, a portion of the lamellae near to the base of the scaffold may have nanofiber arrays configured for the propagation of stem cells while maintaining their stemness; an adjacent portion may be optimized for the differentiation of stem cells into osteocytes; and a third portion may be optimized for differentiation into chondrocytes. Scaffolds with stacked lamellae parallel to the basal plane of the scaffold also have resilient compressive strength that is enhanced by the hydrostatic and hydrodynamic effects of fluids and cells in the interlamellar spaces of the scaffold. Repetitive loading of a scaffold of this type not only causes enhanced flow of viscous fluid elements within the scaffold, but also creates shear stress on the cells within the scaffold thereby enhancing cell development and attachment to the scaffold.

Biomimetic lamellar scaffolds of the present invention may be used for the regeneration of virtually any soft tissue or bone. Hereafter the use of these scaffolds will be described for the treatment of chondral and osteochondral lesions. This is for illustrative purposes only and not intended in any way to limit the scope of methods and devices of the present invention.

When treating a chondral or osteochondral lesion using a lamellar scaffold of the present invention, the site is typically prepared in the same manner as for microfracture treatment. Lamellar scaffolds of the present invention may be supplied to the surgeon as blanks of various sizes that the surgeon may cut and shape to match the geometry of the prepared lesion. Alternatively, the scaffolds may be provided in a range of standardized sizes and shapes ready for placement in the defect. For example, these scaffolds may be provided as a selection of incrementally sized round and/or oblong shapes, the preparation of the lesion by the surgeon including the additional step of sizing and shaping the lesion to accept one of the standard scaffolds. Thereafter the scaffold is placed in the lesion. Optionally the scaffold is secured in the lesion by fibrin glue applied at the perimeter of the scaffold. Other means of securing the scaffold in the defect may include sutures and bioabsorbable PLLA staples. Methods for treating chondral and osteochondral lesions with biomimetic lamellar scaffolds with nanofiber arrays as previously herein described fall within the scope of this invention regardless of the method by which they are secured in a defect.

After the scaffold is secured in the defect, the exposed surface of the scaffold may be shaped to match the contour of the surrounding articular surface.

Optionally, the scaffold may be soaked in concentrated stem cells and growth factors prior to placement in the prepared lesion. In a preferred embodiment, autologous materials are used. In other embodiments, cells from another source are used. When using autologous cells, the surgeon first aspirates bone marrow from a suitable location after which the bone marrow is centrifuged to concentrate the stem cells and growth factors. Optionally, minced healthy cartilage harvested during debridement of the lesion margins to establish stable walls may be added, as may cultured autologous chondrocytes. When centrifuging is complete, the scaffold is soaked in the concentrated stem cells and growth factors from the centrifuge until the scaffold is saturated. The scaffold is then placed in the prepared site as previously described. Optionally a coating of fibrin glue is applied to the surface to ensure that stem cells and growth factors remain in place at least temporarily.

Optionally, the surgeon may perform a microfracture procedure prior to placement of the scaffold in an articular lesion. Stem cells and growth factors flowing from the bone marrow through the microfracture passages enter the scaffold and propagate therethrough.

Optionally, the surgeon may apply a thin coating of a bioactive material to the bottom surface of the prepared lesion site to stimulate the growth of bone adjacent to the surface. The bioactive material may be, for instance, calcium hydroxyapatite, silicon nitride, or magnesium, the latter two materials providing an antimicrobial benefit as well as an osteoinductive effect. Other bioactive materials may also be used for achieving desired results with regard to the tissue types to be regenerated in specific zones of the defect.

Stem cells and growth factors that populate the scaffold regenerate tissue in the defect, the cell type distributions being determined by characteristics of the scaffold. The biodegradable material from which the scaffold is formed is replaced by extracellular matrix during the process.

While the use of scaffolds of the present invention has been described primarily with reference to the treatment of articular lesions, scaffolds of the present invention may be used to regenerate virtually any soft tissue or bone. For instance, scaffolds of the present invention may be used to augment a rotator cuff repair through the growth of additional cuff tendon tissue. In this and other applications, scaffolds of the present invention may be combined with other absorbable patches that provide additional physical strength to the construct during tissue formation and absorption of the scaffold. Scaffolds of the present invention, optimized for the purpose, may be used to regenerate myocardial tissue to replace portions of the heart damaged by heart attacks. Though the blood supply to the sites is undesirably limited, scaffolds of the present invention may provide advantages over other currently used tissue scaffolds for the treatment of diabetic foot ulcers.

While in vivo applications for biomimetic lamellar scaffolds of the present invention have been heretofore described, in vitro uses are also contemplated and fall within the scope of this invention. For instance, it is anticipated that knee structures like ligaments and menisci can be grown using shaped scaffolds of the present invention combined with suitable biologic materials. An anterior cruciate ligament (ACL) or posterior cruciate ligament (PCL) or indeed any elongate tissue structure can be generated using an elongate scaffold of the present invention. Lamellae for these scaffolds have nanofiber arrays that encourage cell orientations aligned with the axis of the scaffold. This alignment may be enhanced and the strength of the resulting tissue structure increased by subjecting the graft to intermittent cyclic loading. Some embodiments of scaffolds of the present invention for producing elongate tissue structures have features at their ends for attachment to an external means for applying tensile, torsional or compressive forces to the scaffold and to cells propagating therein. In certain embodiments, scaffolds of the present invention may comprise portions that are biocompatible but not bioabsorbable. These scaffolds form a composite structure in the regenerated tissue with the non-absorbed scaffold portions dispersed in a tissue matrix. The non-absorbed portions of the scaffold provide enhanced mechanical properties to the composite tissue structure. These non-absorbable portions of the scaffold may or may not have nanofiber arrays on their surfaces.

The configuration of a tissue structure formed in vitro using scaffolds of the present invention will have a form and cellular composition that are determined by the scaffold. In the case of an elongate structure like an ACL or PCL, the structure may be composed of a single cell type and orientation, or be made up of more than one cell type. For instance, by forming the scaffold of lamellae that have discrete zones in which the central portion has nanofiber arrays optimized for the growth of ligament cells, and end portions with nanofiber arrays optimized for the growth of bone. The resulting tissue structure has a central portion formed of ligament tissue, and end portions formed of bone, a construction known as a bone-tendon-bone (BTB) graft commonly harvested from a patellar tendon. Tissue structures created using scaffolds of the present invention may have a form like that of the native structures that they are replacing. In other cases, the tissue structures may differ. For instance, while native ACLs have a more or less cylindrical form, those grown in vitro using scaffolds of the present invention may have a square, rectangular, or oval cross-section. Other beneficial features for increasing the ease of fixation of the graft at implantation may be formed on the graft. For instance, scaffolds of the present invention may be configured to form an eyelet on the end of an ACL or PCL, the eyelet being suitable for suspensory fixation in a femur.

Scaffolds and methods of the present invention may be used for the in vitro growing of not only tissue structures that mimic native structures, but also tissue structures with additional features beneficial for fixation of the structure at implantation and for enhanced vascularization, among other benefits.

Accordingly, in one aspect this disclosure provides a cell growth scaffold comprising a plurality of lamellae formed of a bioabsorbable polymer film with a patterned array of integrally formed polymer nanofibers protruding from a surface of the film, wherein the matrix is configured to modulate the propagation and differentiation of cells cultured in or recruited to the scaffold.

In another aspect this disclosure provides a method for tissue generation in which a lamellar scaffold comprising a plurality of lamellae formed of a bioabsorbable polymer film with a patterned array of integrally formed nanofibers protruding from a surface of the film is placed at a treatment site of a patient. The scaffold is provided with a source for stem cells and growth factors such that stem cell propagation and differentiation occur within the scaffold so as to create tissue of the desired type, the scaffold being absorbed during the process Numerous other objects, advantages and features of the present disclosure will be readily apparent to those of skill in the art upon a review of the following drawings and description of exemplary embodiments.

BRIEF DESCRIPTION OF THE DRAWINGS

Non-limiting and non-exhaustive embodiments are described with reference to the following figures, wherein like reference numerals refer to like parts throughout the various drawings unless otherwise specified. In the drawings, not all reference numbers are included in each drawing, for the sake of clarity.

FIG. 19 is a plan view of the scaffold of FIG. 10 with the approximate outline of the prepared lesion of FIG. 17 marked thereon in preparation for shaping of the scaffold for placement in the lesion.

FIG. 20 is a plan view of the scaffold configured for placement in the lesion of FIG. 17.

FIG. 21 is a perspective view of the objects of FIG. 20

DETAILED DESCRIPTION

Figure 1:
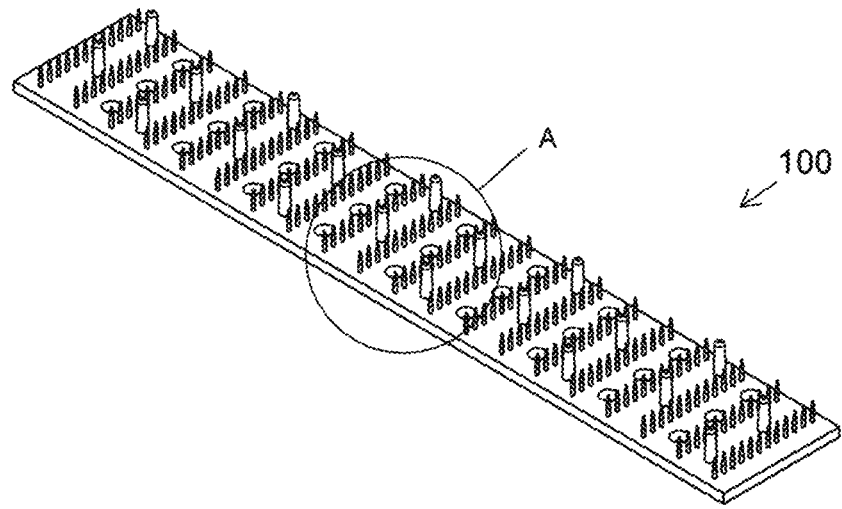
FIG. 1 is a perspective view of a lamella for a scaffold of the present invention.
Figure 2:
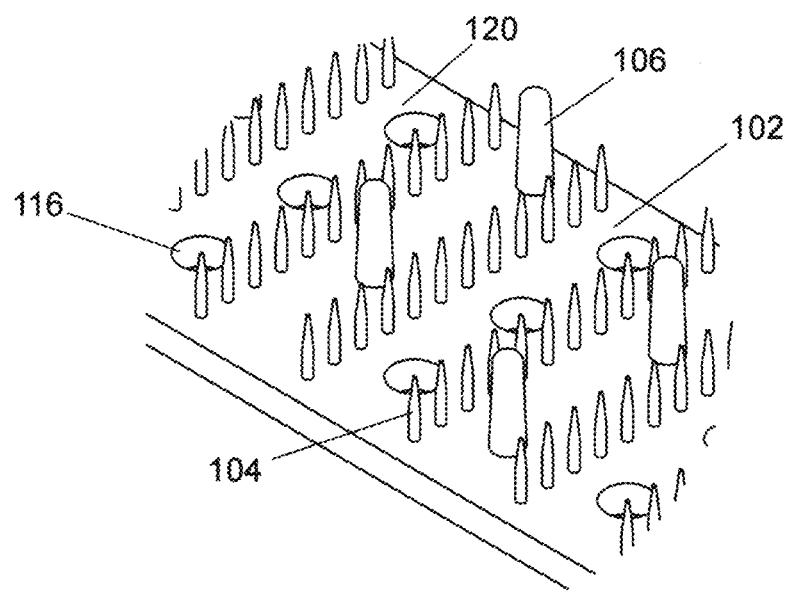
FIG. 2 is an expanded view of the lamella of FIG. 1 at location A.
Figure 3:
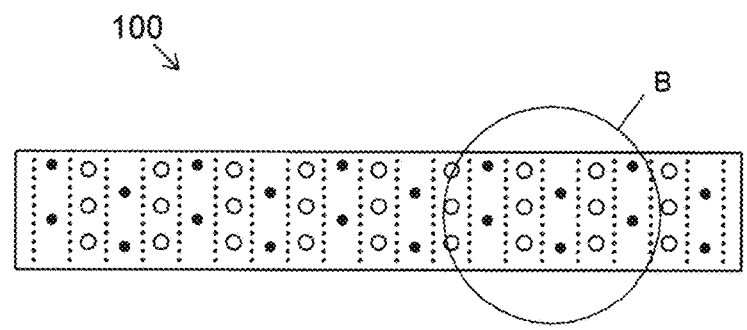
FIG. 3 is a plan view of the objects of FIG. 1.
Figure 4:
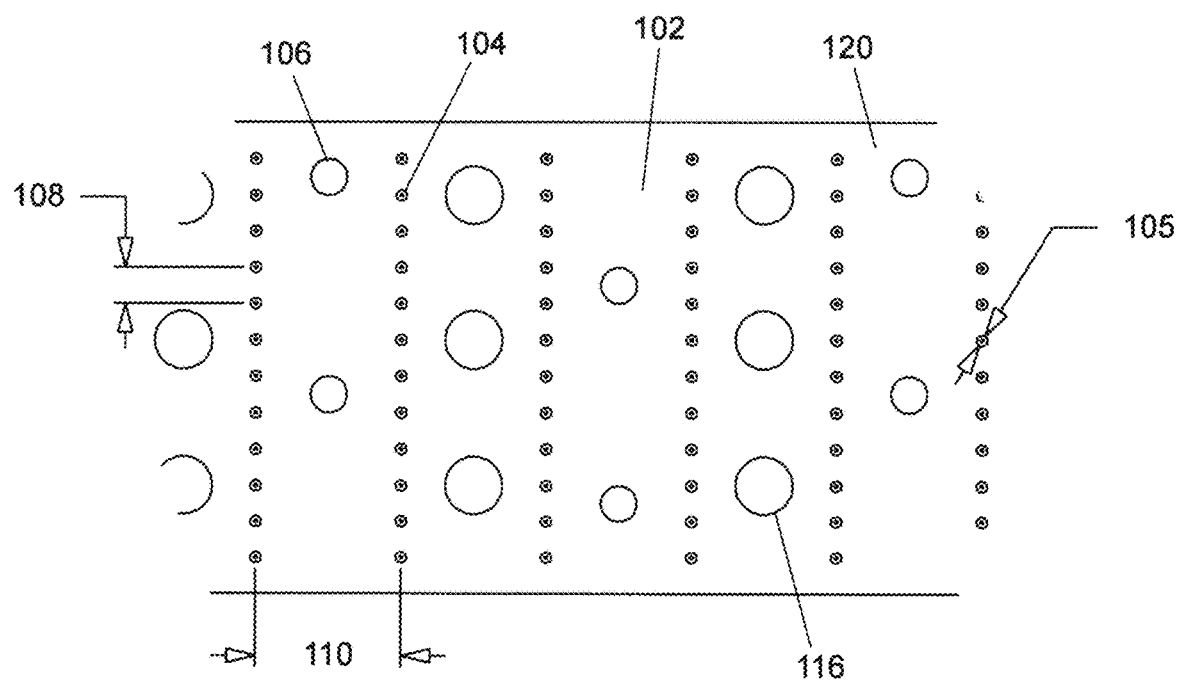
FIG. 4 is an expanded view of the objects of FIG. 3 at location B.
Figure 5:
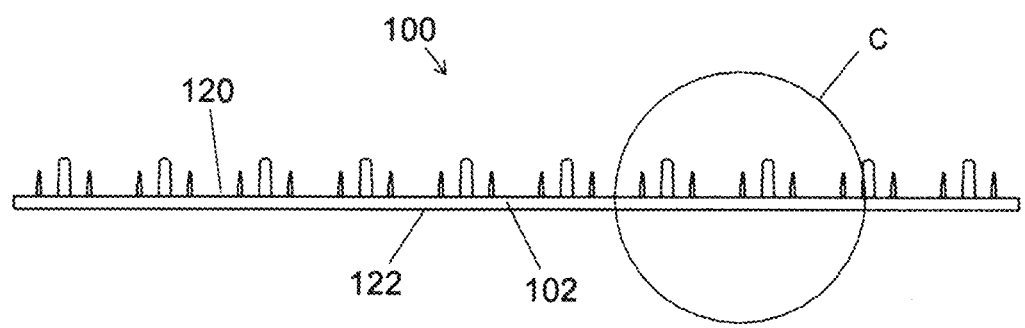
FIG. 5 is a side elevational view of the objects of FIG. 1.

While the making and using of various embodiments of the present invention are discussed in detail below, it should be appreciated that the present invention provides many applicable inventive concepts that are embodied in a wide variety of specific contexts. The specific embodiments discussed herein are merely illustrative of specific ways to make and use the invention and do not delimit the scope of the invention.

To facilitate the understanding of the embodiments described herein, a number of terms are defined below. The terms defined herein have meanings as commonly understood by a person of ordinary skill in the portions relevant to the present invention. Terms such as "a," "an," and "the" are not intended to refer to only a singular entity, but rather include the general class of which a specific example may be used for illustration. The terminology herein is used to describe specific embodiments of the invention, but their usage does not delimit the invention, except as set forth in the claims.

The details of one or more embodiments of the presently disclosed subject matter are set forth in this document. Modifications to embodiments described in this document, and other embodiments, will be evident to those of ordinary skill in the art after a study of the information provided herein. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by one of ordinary skill in the art, definitions are set forth herein to facilitate explanation of the subject matter disclosed herein.

Unless defined otherwise, all technical and scientific terms used herein have the same meaning as commonly understood by one of ordinary skill in the art to which the subject matter disclosed herein belongs. Although any methods, devices, and materials similar or equivalent to those described herein can be used in the practice or testing of the presently disclosed subject matter, representative methods, devices, and materials are now described.

The terms "a", "an", and "the" refer to "one or more" when used in this application, including the claims. Thus, for example, reference to "a cell" includes a plurality of such cells, and so forth. The use of the word "a" or "an" when used in conjunction with the term "comprising" in the claims and/or the specification may mean "one," but it is also consistent with the meaning of "one or more," "at least one," and "one or more than one."

All references to singular characteristics or limitations of the present disclosure shall include the corresponding plural characteristic(s) or limitation(s) and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods and devices of the present disclosure, including components thereof, can comprise, consist of, or consist essentially of the essential elements and limitations of the embodiments described herein, as well as any additional or optional components or limitations described herein or otherwise useful.

Unless otherwise indicated, all numbers expressing physical dimensions, quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently disclosed subject matter.

As used herein, the term "about," when referring to a value or to an amount of mass, weight, time, volume, concentration, percentage or a physical dimension such as length, width, or diameter, is meant to encompass variations of in some embodiments ±20%, in some embodiments ±10%, in some embodiments ±5%, in some embodiments ±1%, in some embodiments ±0.5%, and in some embodiments ±0.1% from the specified value or amount, as such variations are appropriate to perform the disclosed methods.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The present disclosure relates to the inventor's demonstration that the patterned matrices of polymer nanofibers disclosed herein promote stemness and cell-cell interaction of stem cells. Accordingly, in some embodiments, the disclosure is directed to a novel scaffold, that is, a temporary structure that provides an environment suitable for the regeneration of tissues and organs. Embodiments of a scaffold for promoting tissue growth can include lamellae formed of a polymer film and a patterned matrix of polymer nanofibers protruding from a surface thereof.

By the term "lamella" (plural "lamellae") it is generally meant a thin plate-like structure. When describing biological tissue, a lamella may be a thin plate, membrane or layer, as in the basal lamella of an extracellular matrix. When used in reference to mimetic scaffolds of the present invention, "lamella" refers to a polymer film on which an ordered array of nanofibers has been formed integral to the film. Also, in reference to scaffolds of the present invention, "lamellar structure" is a construct formed of a plurality of lamellae arranged in a parallel fashion. A "lamellar scaffold" is a lamellar structure that temporarily mimics the extracellular matrix during tissue regeneration. "Interlamellar space" refers to a void formed between adjacent lamellae forming tissue scaffolds of the present invention for the purpose of cellular propagation therethrough.

As used herein, "lamina" is synonymous with "lamella", "laminae" or "laminas" is synonymous with "lamellae", and "laminar" is synonymous with "lamellar", the terms being interchangeable throughout.

The polymer film can be any bioabsorbable thermoplastic polymer. Examples of suitable bioabsorbable thermoplastic polymers include epsilon-polycaprolactone (PCL), polyglycolic acid (PGA), polylactic acid (PLA), polydioxanone (PDS), and copolymers of PGA and PLA, among others.

By the term "patterned" it is generally meant that the polymer nanofibers disclosed herein are arranged or ordered into a user-defined pattern or array. In some embodiments, the term "patterned" can refer to the spacing of polymer nanofibers on a lamella. On a substantially flat lamella, such as a polymer film, the nanofibers disclosed herein can be spaced along an X-axis and a Y-axis at the same or different intervals along either axis. In some embodiments, nanofibers can be spaced about 50 microns, 40 microns, 30 microns, 20 microns, 10 microns, 9 microns, 8 microns, 7 microns, 6 microns, 5 microns, 4 microns, 3 microns, 2 microns, or 1 microns apart on an X-axis and about 50 microns, 40 microns, 30 microns, 20 microns, 10 microns, 9 microns, 8 microns, 7 microns, 6 microns, 5 microns, 4 microns, 3 microns, 2 microns, or 1 micron apart on a Y-axis The term "matrix" as used herein refers generally to a structure or environment in which living cells can be cultured and "patterned matrix" refers to a matrix with engineered order. For example, a patterned matrix of polymer nanofibers can include a plurality of standing polymer nanofibers with user-defined physical dimensions arranged according to user-defined spatial parameters. User-tunable parameters include fiber spacing, diameter (also sometimes referred to herein as "width"), height (also sometimes referred to herein as "length"), and number of fibers per unit of surface area (also referred to herein as "fiber surface area density").

In some embodiments, a patterned matrix of polymer nanofibers can include nanofibers having an average length of at least 10.00 microns. In certain embodiments, the nanofibers can have a length of from about 10.00 microns to about 60.00 microns. In an exemplar embodiment, the nanofibers can have an average length of from about 15.00 microns to about 35.00 microns. In specific embodiments, the nanofibers can have a length of about 10.00 microns, 11.00 microns, 12.00 microns, 13.00 microns, 14.00 microns, 15.00 microns, 16.00 microns, 17.00 microns, 18.00 microns, 19.00 microns, 20.00 microns, 21.00 microns, 22.00 microns, 23.00 microns, 24.00 microns, 25.00 microns, 26.00 microns, 27.00 microns, 28.00 microns, 29.00 microns, 30.00 microns, 31.00 microns, 32.00 microns, 33.00 microns, 34.00 microns, 35.00 microns, 36.00 microns, 37.00 microns, 38.00 microns, 39.00 microns, 40.00 microns, 41.00 microns, 42.00 microns, 43.00 microns, 44.00 microns, 45.00 microns, 46.00 microns, 47.00 microns, 48.00 microns, 49.00 microns, 50.00 microns, 51.00 microns, 52.00 microns, 53.00 microns, 54.00 microns, 55.00 microns, 56.00 microns, 57.00 microns, 58.00 microns, 59.00 microns, or 60.00 microns.

In some embodiments, a patterned matrix of polymer nanofibers can include nanofibers having an average diameter of from about 0.10 microns to about 1.20 microns. In an exemplar embodiment, the nanofibers can have an average diameter of 0.24 microns to 0.34 microns. In certain embodiments, the nanofibers can have an average diameter of about 0.10 microns, 0.15 microns, 0.20 microns, 0.25 microns, 0.26 microns, 0.27 microns, 0.28 microns, 0.29 microns, 0.30 microns, 0.31 microns, 0.32 microns, 0.33 microns, 0.34 microns, 0.35 microns, 0.40 microns, 0.45 microns, 0.50 microns, 0.55 microns, 0.60 microns, 0.65 microns, 0.70 microns, 0.75 microns, 0.80 microns, 0.85 microns, 0.90 microns, 0.95 microns, 1.00 microns, 1.05 microns, 1.10 microns, 1.15 microns, or 1.20 microns.

The nanofiber lamella surface area density can range from about 1 to about 30 nanofibers per 100 microns$^2$. In some embodiments, the nanofiber surface area density can range from about 6 to about 25 nanofibers per 100 microns$^2$. In specific embodiments, the nanofiber surface density is about 6, 7, 8, 9, 10, 11, 12, 13, 14, 15, 16, 17, 18, 19, 20, 21, 22, 23, 24, or 25 nanofibers per 100 microns$^2$. In an exemplar embodiment, the nanofiber surface area density is about 16.7 nanofibers per 100 micron$^2$.

In certain embodiments, a matrix of polymer nanofibers is configured to modulate gene expression in stem cells cultured on or recruited to the scaffold relative to control cells cultured in the absence of the matrix. As used herein, "modulate gene expression" refers to increasing or decreasing the expression of one or more genes encoding a polypeptide involved in cell self-renewal or cell-cell interaction, alone or in combination with other transcription and/or translational regulatory factors or nucleic acids encoding such a polypeptide. As used herein, the term "stem cell" can be any type of undifferentiated cell of a multicellular organism that is capable of giving rise to more cells of the same type, and from which certain other kinds of cell arise by differentiation. Stem cells can be either embryonic or adult stem cells. In an exemplar embodiment, the stem cells are human mesenchymal stem cells. The terms "culture" and "cultured" as used herein refer to the cultivation or maintenance of cells under conditions suitable for growth. The term "control cells" refers to cells of the same type cultured under the same conditions as cells cultured on the matrix, except that the control cells are cultured on Tissue culture polystyrene (TCPS) or flat PCL in the absence of the matrix.

In specific embodiments, the patterned nanofiber matrix is configured to increase expression in cells cultured on or recruited to the matrix of a nucleic acid encoding a self-renewal transcription factor polypeptide or a cell-cell interaction marker polypeptide relative to control cells cultured in the absence of the matrix.

The terms "polypeptide" refers to a polymer of amino acids, or amino acid analogs, regardless of its size or function. Exemplary polypeptides include gene products, naturally occurring proteins, homologs, orthologs, paralogs, fragments and other equivalents, variants, and analogs of the foregoing.

Scaffolds of the present invention have a lamellar construction. In some embodiments the lamellae of the scaffold are perpendicular to the plane of the scaffold. In others they are parallel to the base. Nanofiber arrays optimally tuned for the propagation of a desired cell type are formed on a surface of each lamella. Pedestals formed on the surface maintain proper spacing between the lamellae so as to create inter-lamellar spaces through which cells may propagate and through which nutrients may be transported to the developing cells.

Referring now to FIGS. 1 through 6 diagrammatically depicting a lamella for forming scaffolds of the present invention, lamella 100 has an elongate flexible planar portion 102 with a first surface 120 and a second surface 122. First surface 120 has formed on it an array of nanofibers 104 and pedestals 106 integral with planar portion 102. Nanofibers 104 of basal diameter 105 are spaced distance 110 apart parallel to an elongate edge of planar portion 102, and distance 108 apart perpendicular to an elongate edge, distance 110 being greater than distance 108. Nanofibers 104 have a nominal height 112 with some variations in height occurring due to variations in the depth of nanoholes in the patterned substrate used to form the lamella, and possible stretching during removal of nanofibers 104 from the patterned substrate. Pedestals 106 have a height 114, height 114 being greater than nominal height 112. Distances 108 and 110, and heights 112 and 114 together are optimized to form a biomimetic cell culture substrate. Pedestals 106 are depicted as truncated cones. In other embodiments pedestals 106 may have elliptical, oval, or other cross-sections optimized for specific applications. In some embodiments planar portion 102 has formed therein holes 116. Holes 116 may be round, elliptical, slots, or have curvilinear shapes. The configuration, size, number and placement of holes 116 may be optimized to meet specific requirements.

Figure 6:
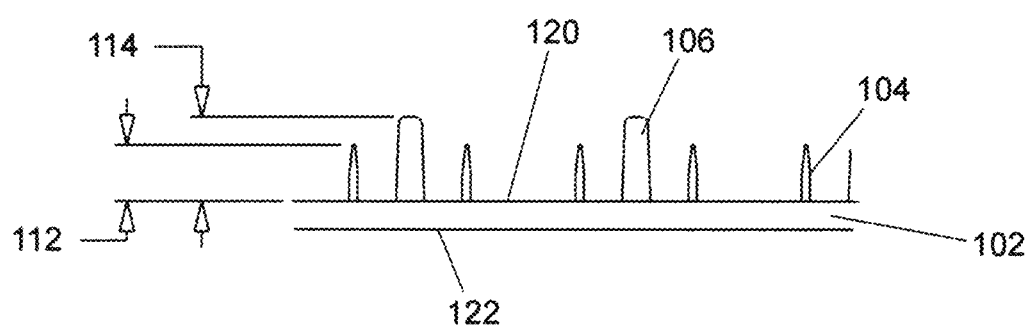
FIG. 6 is an expanded view of the objects of FIG. 5 at location C.

As best seen in FIG. 6, nanofibers 104 have a non-uniform cross-section. Specifically, nanofibers 104 are tapered so as to provide a reduced flexural rigidity in portions of fibers 104 more remote from first surface 120 of lamella 100. This rigidity profile is beneficial for the attachment of stem cells thereto and for the transfer of shear stresses to the cell with its associated previously described benefits.

Lamella 100 forms a biomimetic cell culture substrate as described in co-pending application US 2016/0222345. Lamella 100 mimics the extracellular matrix (ECM), a primary environmental constituent that heavily influences cell behavior. Tuned arrays of nanofibers 104 provide a form of "outside in" signaling that, along with other factors, determines cell behavior. Specifically, the tuned arrays of lamella 100 are optimized for stem cells and human mesenchymal stem cells ("hMSCs") to influence their decision to either maintain their stem cell phenotype or differentiate towards a specified cell lineage, for instance, to differentiate into chondrocytes for hyaline-like cartilage regeneration and/or osteocytes for subchondral bone formation. Nanofibers 104 are patterned on the micron scale over expanses of lamellar surfaces. The attachment of fibers 104 at the surface of planar portion 102 of substrate 100 mimics the basement membrane where fibrils of collagen forming an ECM are in contact with a highly cross-linked collagen IV layer. When used to culture hMSCs, biomimetic substrates typified by lamella 100 were found to significantly increase expression of critical regulators of self-renewal, as well as markers indicative of increased cell-cell interaction that are paramount in stem cell homeostasis.

Accordingly, nanofibers 104 may have a basal diameter preferably between 0.1 micron and 2.0 microns, and more preferably between 0.2 and 0.8 microns. Distances 108 and 110 between nanofibers 104 are preferably between 1 and 50 microns, and more preferably between 2 and 20 microns. Distances 108 and 110 may be equal or may differ. In some embodiments distances 108 and 110 may remain constant for the entirety of lamella 100. In other embodiments a first portion of the array of nanofibers 104 on lamella 100 may have first distances 108 and 110, and a second portion of the array in which distance 108 or distance 110 or both 108 and 110 differ from the values in the first portion. Indeed, distances 108 and 110 may have a range of values for the array of nanofibers 104 on a lamella 100, the range of values selected to achieve a specific outcome with relation to the propagation of hMSCs. The array of nanofibers 104 depicted on lamina 100 is formed of linear arrangements. In other embodiments arrays of nanofibers 104 may be formed of curvilinear or circuitous patterns of nanofibers 104.

Similarly, nominal height 112 of nanofibers 104 may be optimized to achieve specific outcomes. Height 112 of nanofibers 104 is preferably between 10 and 100 microns, and more preferably between 20 and 60 microns. In some embodiments the nominal height 112 of nanofibers 104 is constant. In other embodiments nominal height 112 of nanofibers 104 may have a first value for a first portion of the array of nanofibers 104 and a second value in a second portion of the array. As with the spacings 108 and 110 of nanofibers 104, nominal height 112 may have a range of values for the array of nanofibers 104 on a lamella 100, the range of values selected to achieve a specific outcome with relation to the propagation of hMSCs.

Lamella 100 is formed of a suitable bioabsorbable polymeric material. Among others, these materials include PCL (epsilon-polycaprolactone), PLLA (poly 1-lactic acid), PGA (polyglycolic acid), and PLGA (poly 1-lactic acid co-glycolic acid).

Nanofibers 104 may be formed on planar portion 102 by a variety of methods, planar portion 102 being a flexible polymeric film. In a preferred embodiment, nanofibers 104 are formed by hot pressing of the polymer film on a substrate in which arrays of nanoholes have been formed, the pattern of nanohole arrays being complementary to the pattern of nanofibers to be formed on the film. Prior to pressing, the film is heated sufficiently to allow the polymer to flow into the nanoholes when pressure is applied to the film. The film is cooled prior to removal from the substrate so as to allow the polymer to set sufficiently to allow removal of the nanofibers from the nanoholes in which they were formed. This hot-pressing method of nanofiber formation is described in detail in co-pending application US 2016/0223345. The arrays of nanofibers 104 may also be formed by solution casting. Like hot pressing, the solution casting process uses a substrate in which arrays of nanoholes have been formed, the pattern of nanohole arrays being complementary to the pattern of nanofibers to be formed on the film. A polymer/solvent solution is applied to a substrate in sufficient quantity to form a film on the surface of the substrate with the solution flowing into the nanoholes formed in the substrate. The solvent is then allowed to evaporate. When evaporation is complete, the film with nanofibers formed on its surface is peeled off of the substrate. A solution casting process for forming films with arrays of nanofibers is described in detail in co-pending application US 2015/0093550. The hot pressing and solution casting methods for forming a polymeric film with ordered nanofiber arrays on its surface are offered as examples of suitable manufacturing methods only. Any manufacturing method that allows the formation of ordered nanofiber arrays on the surface of a polymeric film suitable for forming lamellar scaffolds of the present invention may be used. Regardless of the manufacturing method, all lamella with ordered arrays of nanofibers formed integral with the film that forms the lamella fall within the scope of this invention.

Figure 7:
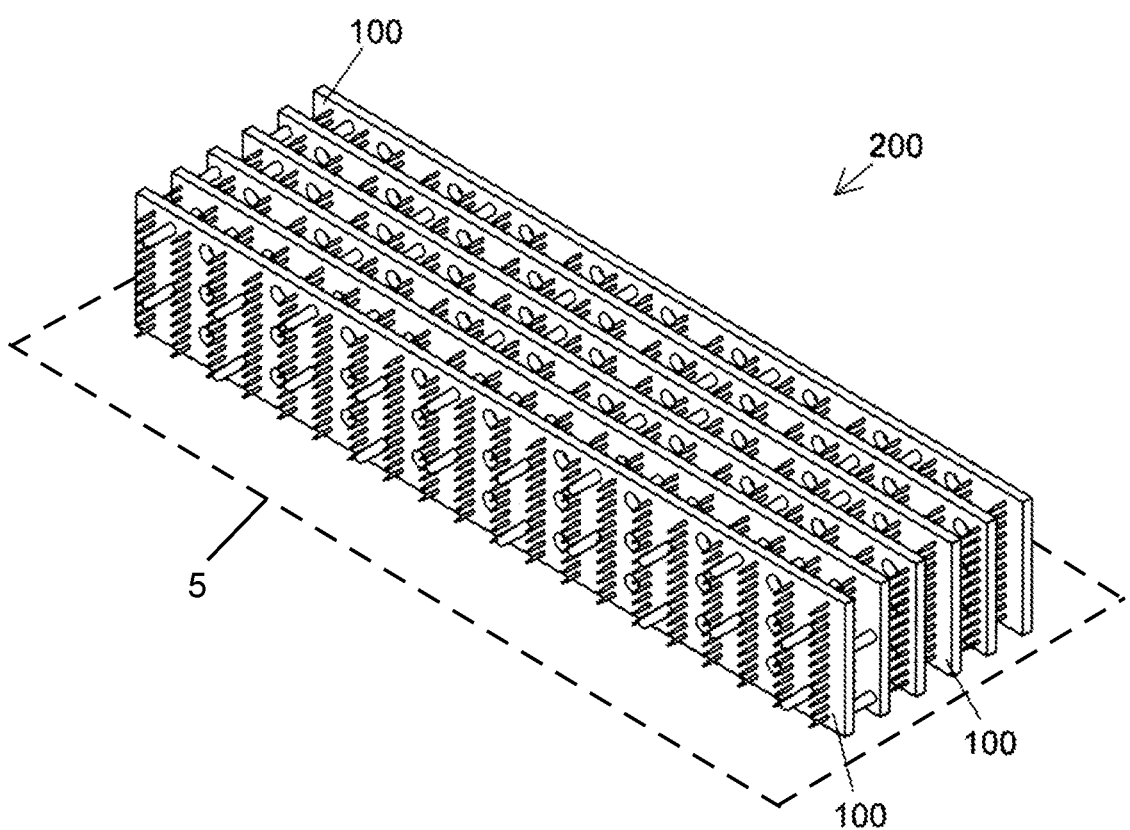
FIG. 7 is a perspective view of a segment of a lamellar scaffold of the present invention.
Figure 8:
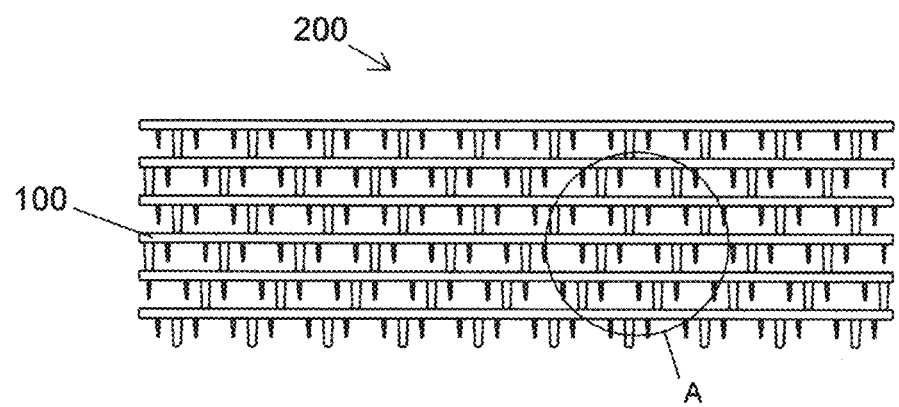
FIG. 8 is a plan view of the objects of FIG. 7.
Figure 9:
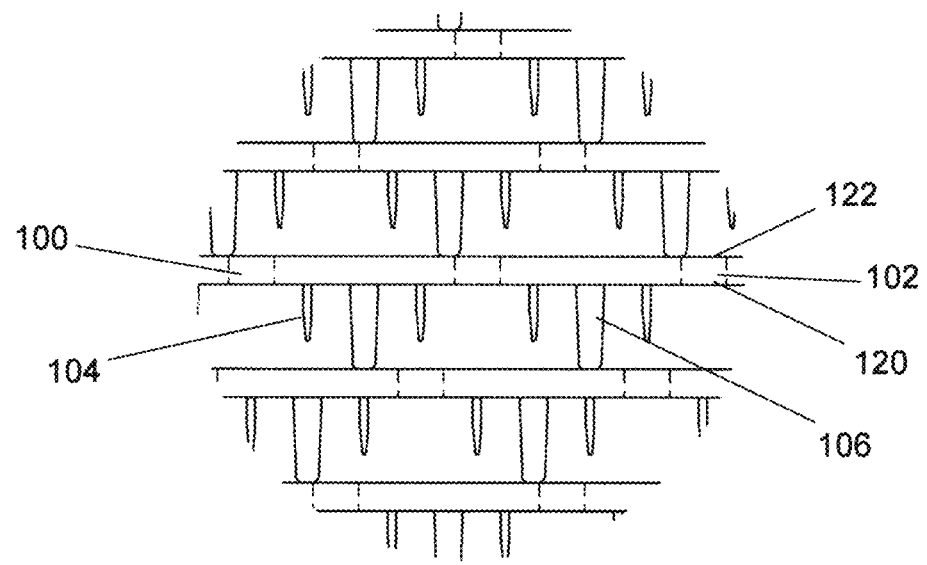
FIG. 9 is an expanded view of the objects of FIG. 8 at location A.

A portion of a lamellar scaffold of the present invention having lamellae oriented perpendicular to a basal plane 5 of the scaffold is diagrammatically depicted in FIGS. 7 through 9. Scaffold portion 200 is formed of a plurality of lamellae 100 positioned with pedestals 106 contacting second surface 122 of adjacent lamellae so as to maintain spacing between the lamellae. In the interlamellar space so created, rows of nanofibers 104 form virtually columnar pipes for the propagation of cultured cells.

Figure 10:
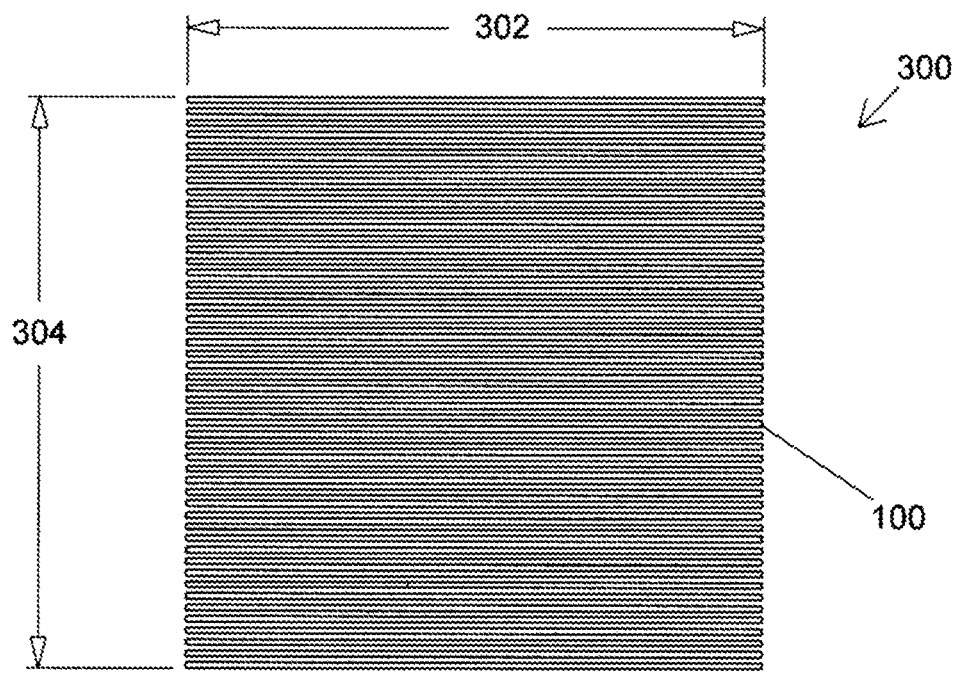
FIG. 10 is a plan view of a lamellar scaffold of the present invention with parallel planar lamellae.
Figure 11:
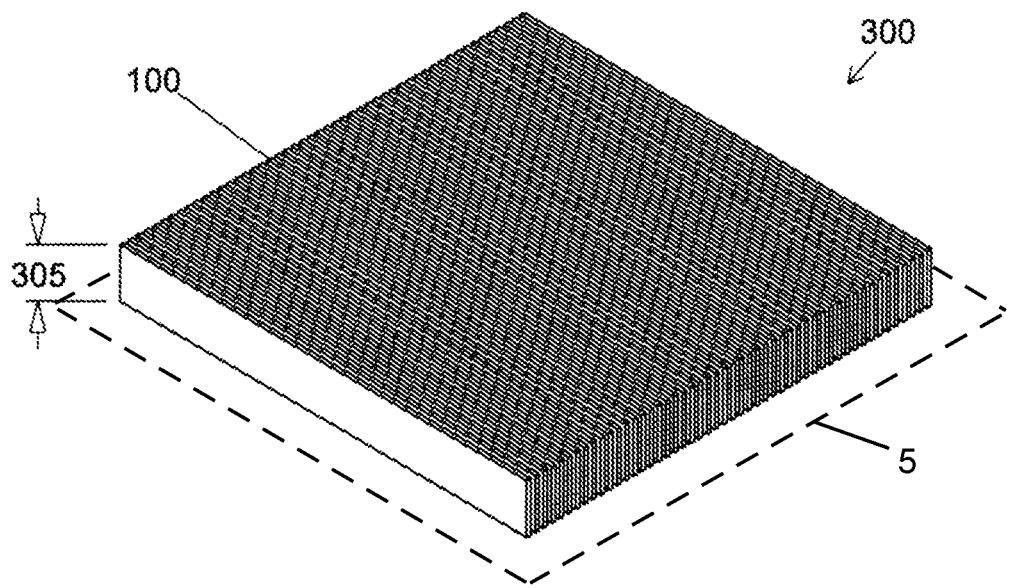
FIG. 11 is a perspective view of the objects of FIG. 10.

Lamellar scaffolds of the present invention may be formed with the lamellae in a parallel planar arrangement like scaffold blank 300 depicted in FIGS. 10 and 11. Scaffold blank 300 of length 302, width 304 and thickness 305 may be cut, etched, abraded, trimmed or shaped by some other method to configure it to meet the spatial requirements of a specific application.

Figure 12:
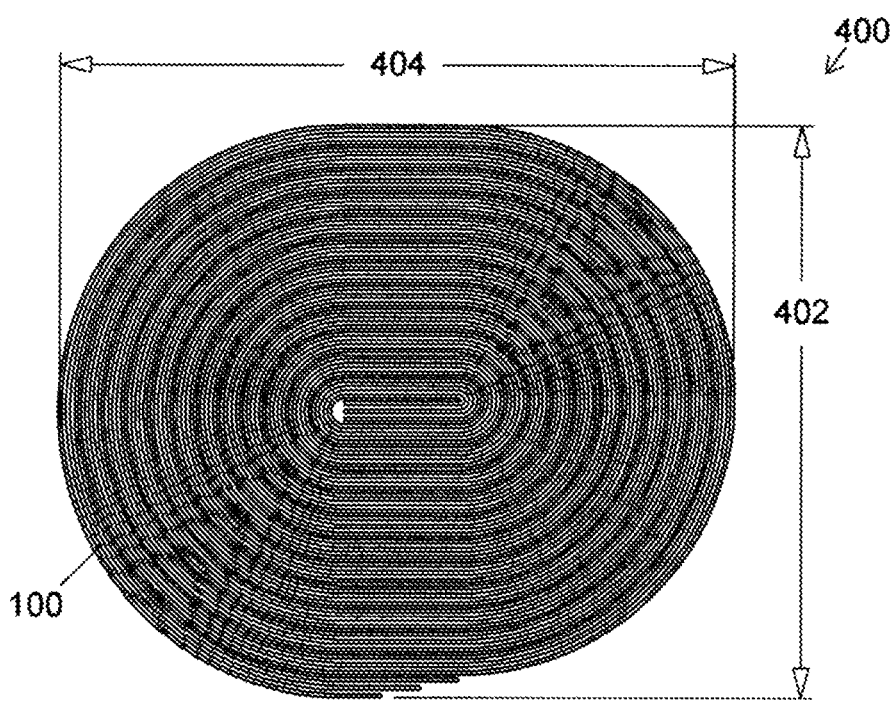
FIG. 12 is a plan view of a lamellar scaffold of the present invention with lamellae arranged in a spiral fashion.
Figure 13:
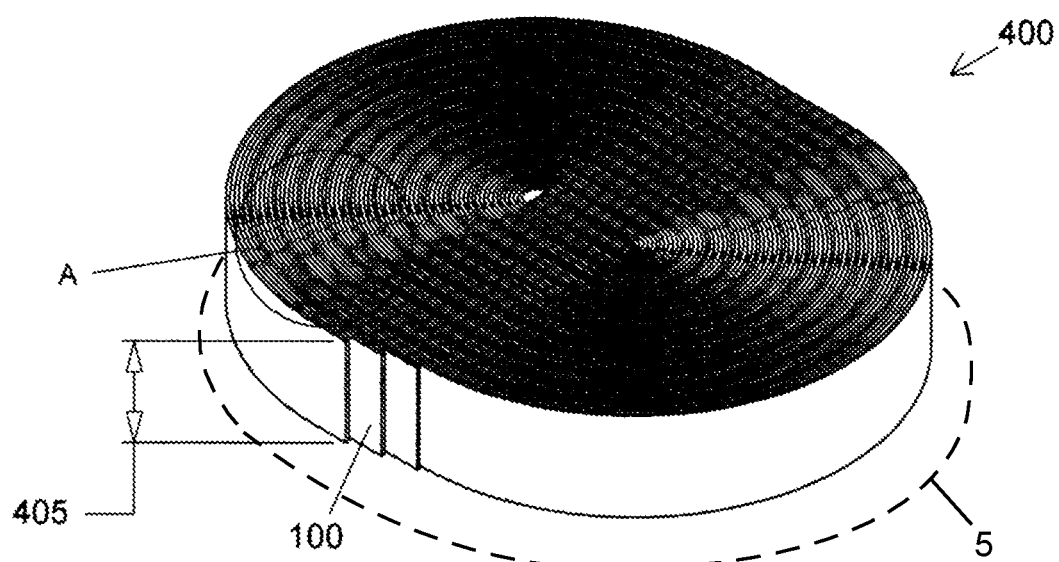
FIG. 13 is a perspective view of the objects of FIG. 12.

Scaffolds of the present invention may also be formed with lamella 100 oriented perpendicular to a basal plane 5 of the scaffold and wrapped in a spiral manner as in scaffold 400 depicted in FIGS. 12 and 13. Scaffold 400 has an oval shape with width 402, length 404 and thickness 405. In other embodiments scaffold 400 is round. Scaffold 400 may be supplied to the surgeon in a variety of standard sizes and configurations. In use, the surgeon selects a scaffold 400 with the size and shape most suitable for a given requirement, and the treatment site is sized and configured to accept the scaffold 400 without modification to scaffold 400.

Parallel planar and spiral arrangements of lamella 100 are depicted herein for example only. Any configuration in which lamella 100 are assembled in a lamellar manner with structural elements maintaining spacing so as to create interlamellar spaces between adjacent lamella or adjacent lamella portions falls within the scope of this invention.

Figure 15:
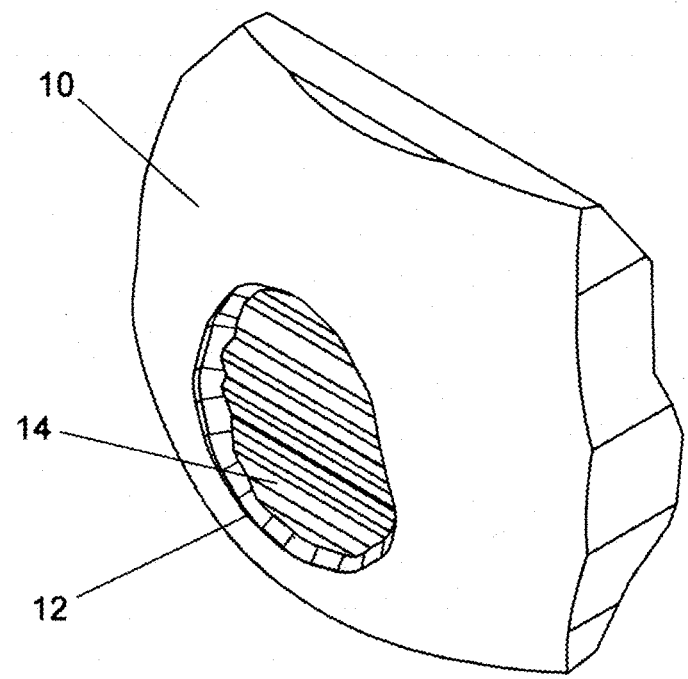
FIG. 15 is a perspective depiction of a lesion in a femoral condyle.
Figure 16:
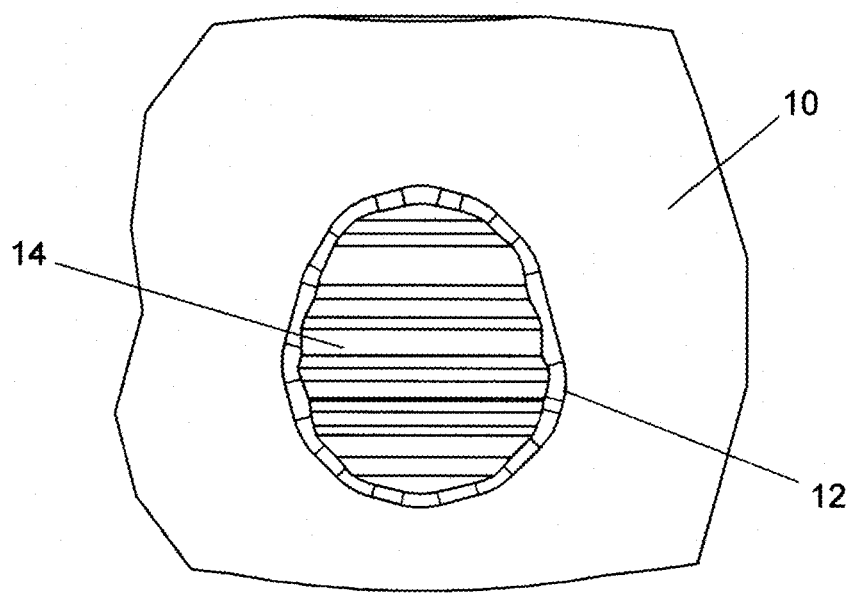
FIG. 16 is a side elevational view of the objects of FIG. 15.
Figure 17:
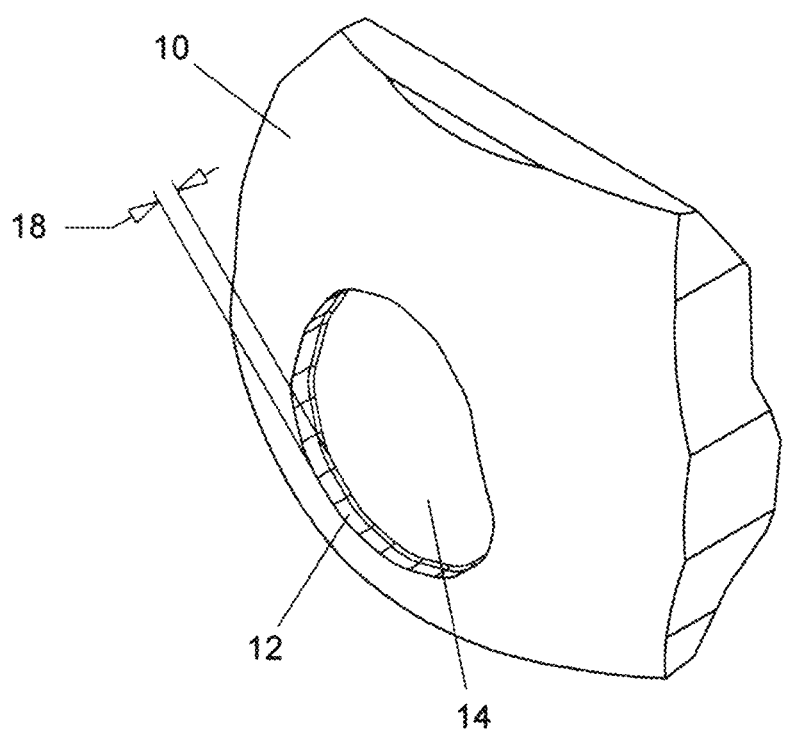
FIG. 17 is a perspective depiction of the condyle of FIG. 15 with the lesion prepared for placement of a lamellar scaffold of the present invention.
Figure 18:
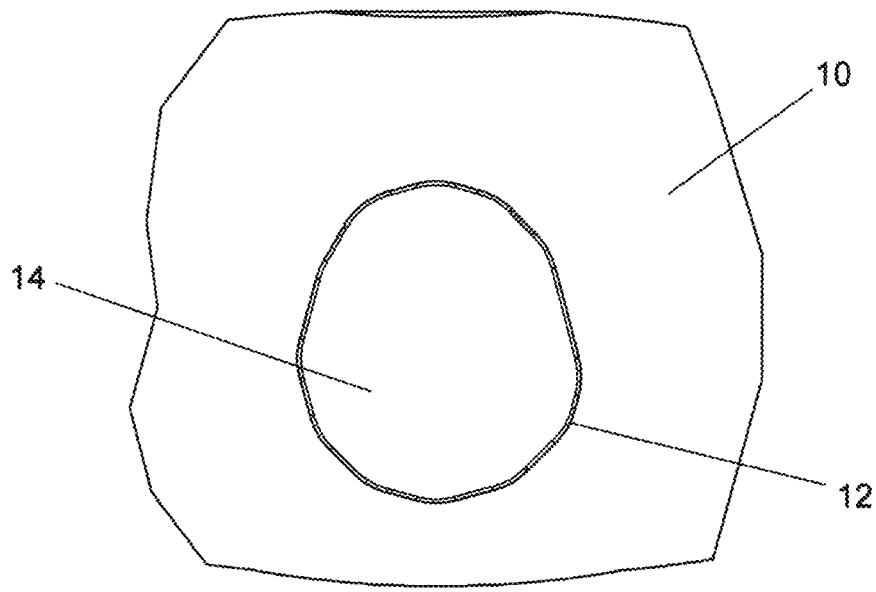
FIG. 18 is a side elevational view of the objects of FIG. 17.
Figure 22:
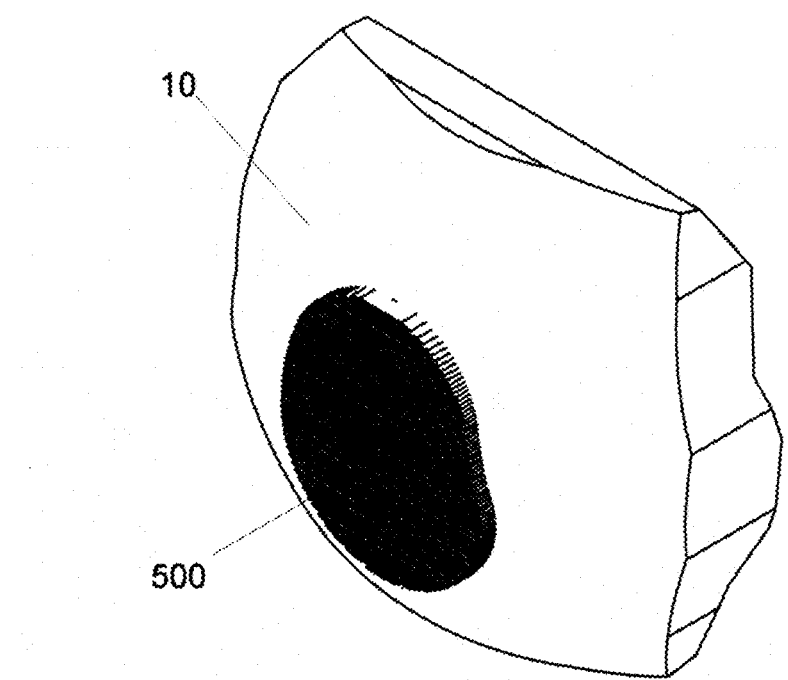
FIG. 22 is a perspective view of the condyle of FIG. 17 with the scaffold of FIG. 20 placed therein.
Figure 23:
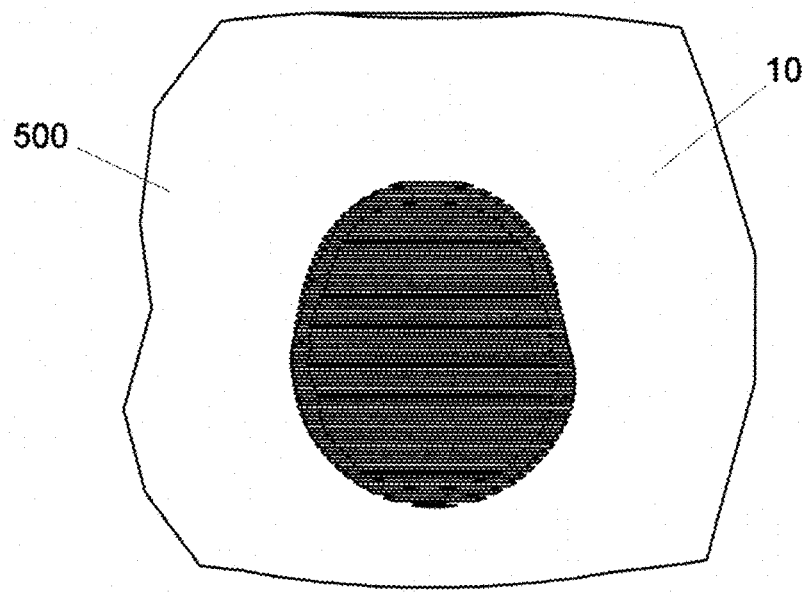
FIG. 23 is a side elevational view of the objects of FIG. 22.
Figure 24:
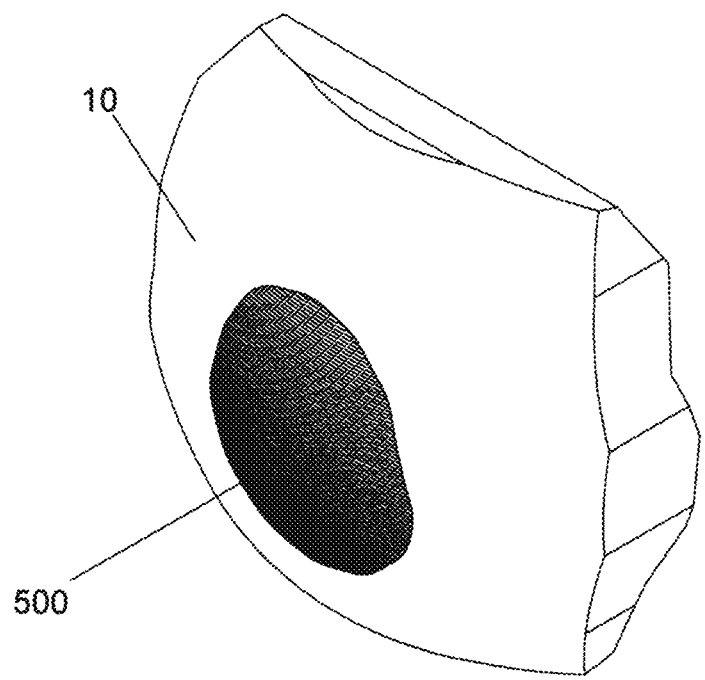
FIG. 24 is a perspective view of the condyle and scaffold of FIG. 22 with the scaffold contoured to match the condyle surface.
Figure 25:
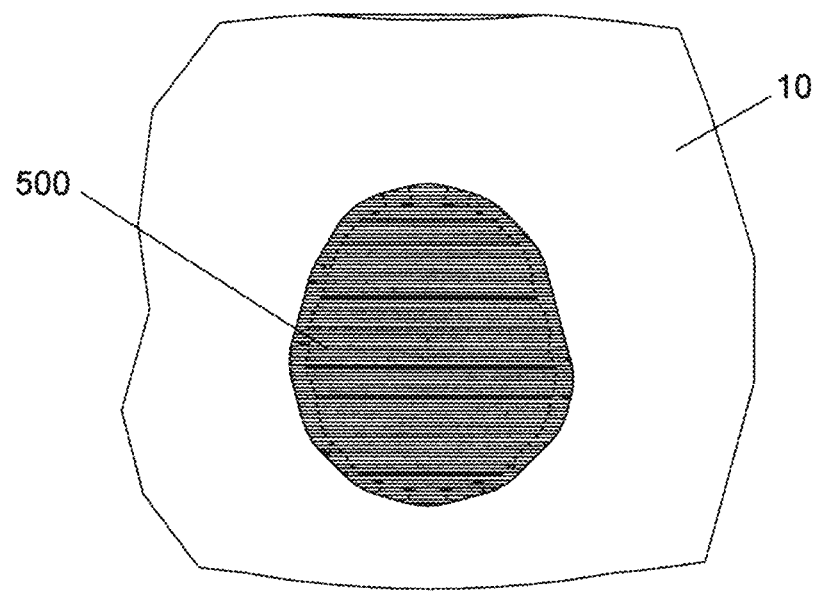
FIG. 25 is a side elevational view of the objects of FIG. 24.

Hereafter, the use of lamellar scaffolds of the present invention will be described with reference to treating an articular lesion on a femoral condyle in a method of the present invention. FIGS. 15 and 16 depict a portion of a femoral condyle 10 with a lesion 12 with recessed surface 14 composed of calcified cartilage and bone. The surgeon preps lesion 12 by removing loose cartilage portions at the perimeter of the defect until the side walls are formed of healthy cartilage and are perpendicular to surface 14. The surgeon removes calcified cartilage from surface 14 to expose underlying bone. Thereafter, the site is as depicted in FIGS. 17 and 18. The size, shape and depth 18 of defect 12 are determined and the outline scribed on scaffold blank 300 (see FIG. 19) with suitable length 302 width 304 and thickness 305. Blank 300 is then shaped to form scaffold 500 shown in FIGS. 20 and 21. Thickness 505 of scaffold 500 may be reduced from 305 of blank 300, so long as it is still greater than depth 18 of defect 12. Thereafter, scaffold 500 is placed in lesion 12 as depicted in FIGS. 22 and 23. If required, scaffold 500 may be secured to the healthy cartilage forming the perimeter of lesion 12 using fibrin glue. After the glue has set, the outer surface of scaffold 500 is contoured to match the shape of the surrounding articular surface as shown in FIGS. 24 and 25.

As described previously, the surgeon removes calcified cartilage from surface 14 of defect 12 to expose healthy underlying bone prior to placing scaffold 500. Mesenchymal stem cells and growth factors flow from the underlying bone into scaffold 500 so as to populate scaffold 500. Viscous fluids enter the scaffold from the exposed surface bringing nutrients to the developing cells. The propagation and differentiation of stem cells within scaffold 500 is modulated by scaffold 500 so as to create hyaline cartilage or hyaline-like cartilage completely filling the defect.

In an alternate embodiment treatment method of the present invention, scaffold 500 is soaked in concentrated stem cells and growth factors prior to placement in lesion 12. This alternate method is identical in all aspects of form and function to the method previously described except as specifically subsequently described. In a preferred embodiment, autologous materials are used. In other embodiments, cells from another source are used. When using autologous cells, the surgeon first aspirates bone marrow from a suitable location, the bone marrow subsequently undergoing centrifuging to concentrate the stem cells and growth factors. When centrifuging is complete, scaffold 500 is soaked in the concentrated stem cells and growth factors from the centrifuge until scaffold 500 is saturated. Thereafter, scaffold 500 containing the stem cells with which it is infused are placed in lesion 12 as depicted in FIGS. 22 and 23. The repair is then completed in the same manner as the method previously described. Optionally, a coating of fibrin glue is applied to the surface to ensure that stem cells and growth factors remain in place at least temporarily.

In another alternate embodiment treatment method of the present invention a microfracture procedure is performed prior to placing scaffold 500 as previously described to enhance the supply of stem cells and growth factors to scaffold 500. The increased flow may increase the rate of population of stem cells in scaffold 500 yielding an associated increase in the rate of cell proliferation and differentiation. In all other aspects the method of this embodiment is identical to that previously herein described.

In yet another embodiment treatment method of the present invention, a bioactive substance is applied to surface 14 of prepared lesion 12 prior to the placement of scaffold 500 for the purpose of stimulating the growth of subchondral bone. In preferred embodiments the bioactive substance is calcium hydroxyapatite. In other embodiments the substance is silicon nitride or magnesium, these substances also having antimicrobial properties. In yet other embodiments, bioactive substances are provided in the scaffold, more specifically, in selected portions of the scaffold to enhance certain cell behaviors in these regions.

Figure 14:
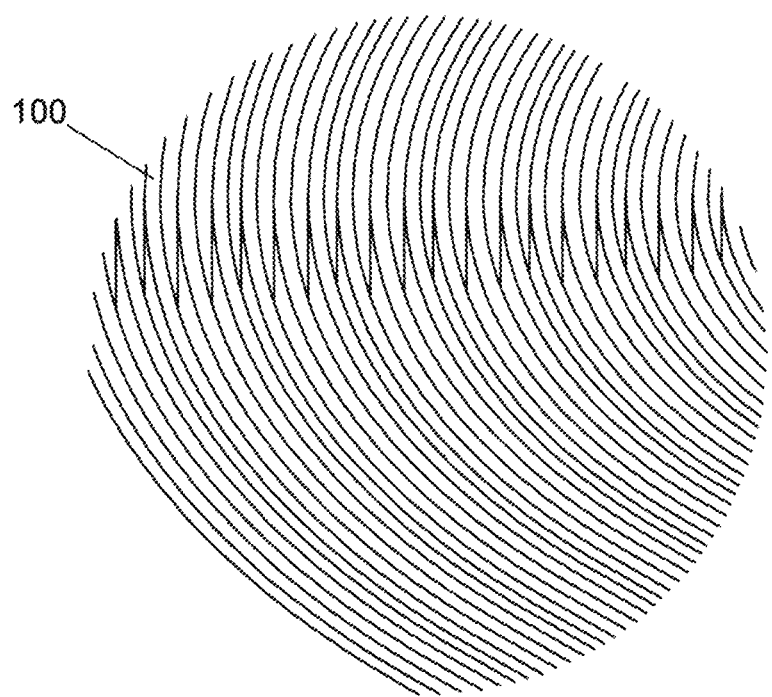
FIG. 14 is an expanded view of the objects of FIG. 13 at location A.
Figure 26:
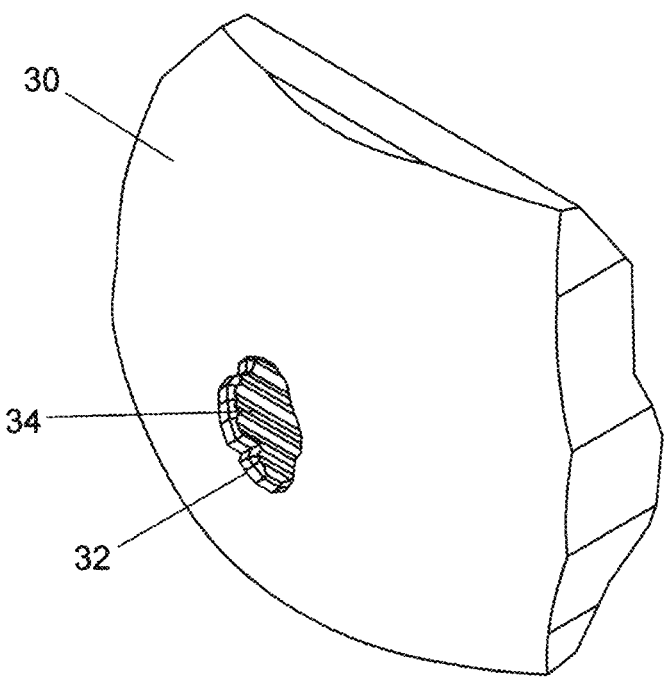
FIG. 26 is a perspective view of a femoral condyle with a lesion in the articular surface.
Figure 27:
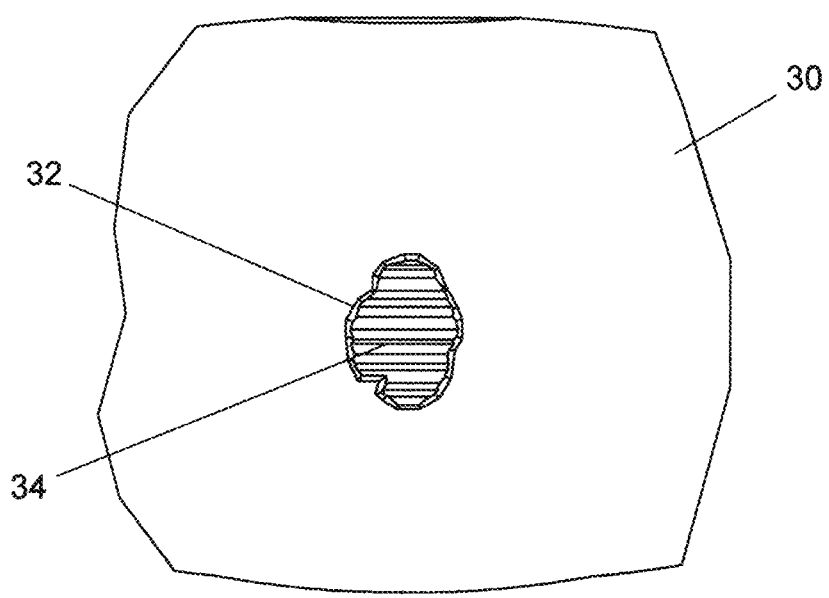
FIG. 27 is a side elevational view of the objects of FIG. 26.
Figure 28:
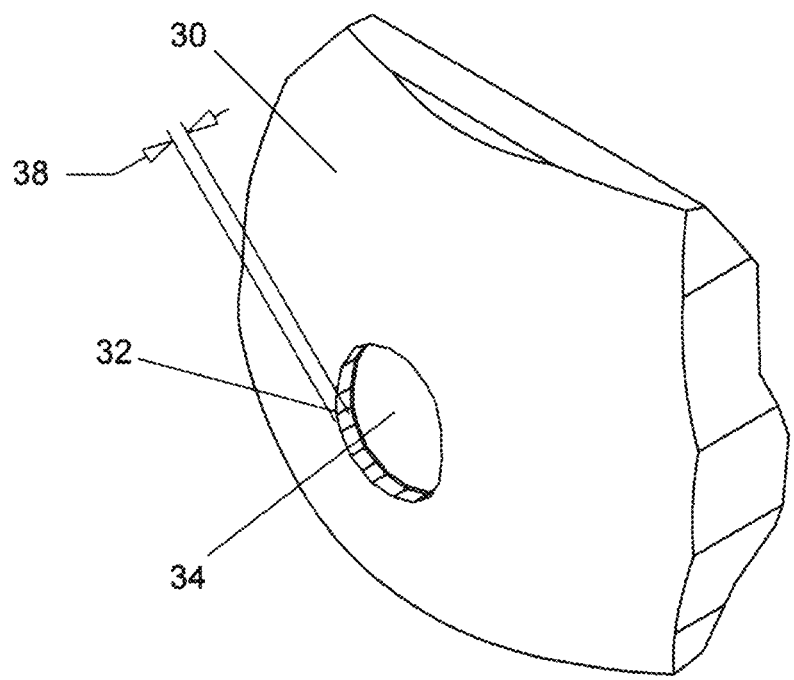
FIG. 28 is a perspective view of the condyle of FIG. 26 with the lesion prepared for placement therein of a lamellar scaffold of the present invention.
Figure 29:
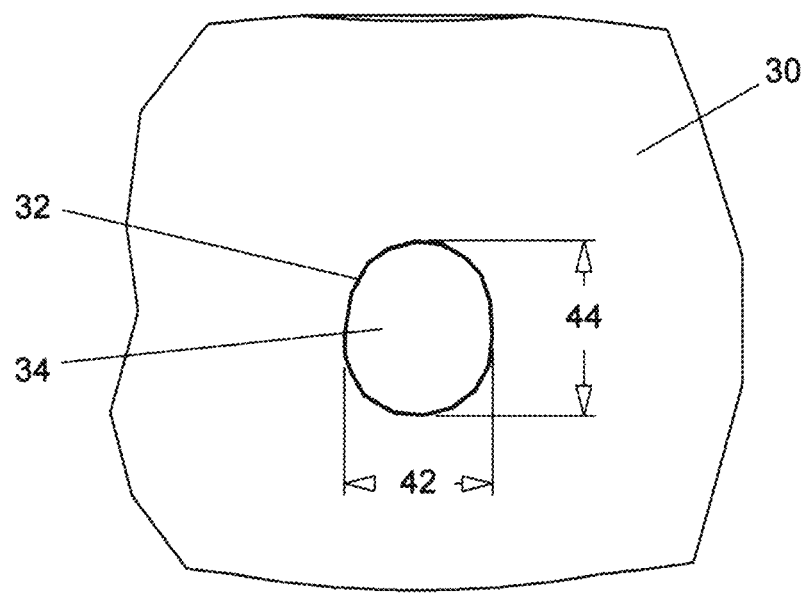
FIG. 29 is a side elevational view of the objects of FIG. 28.
Figure 30:
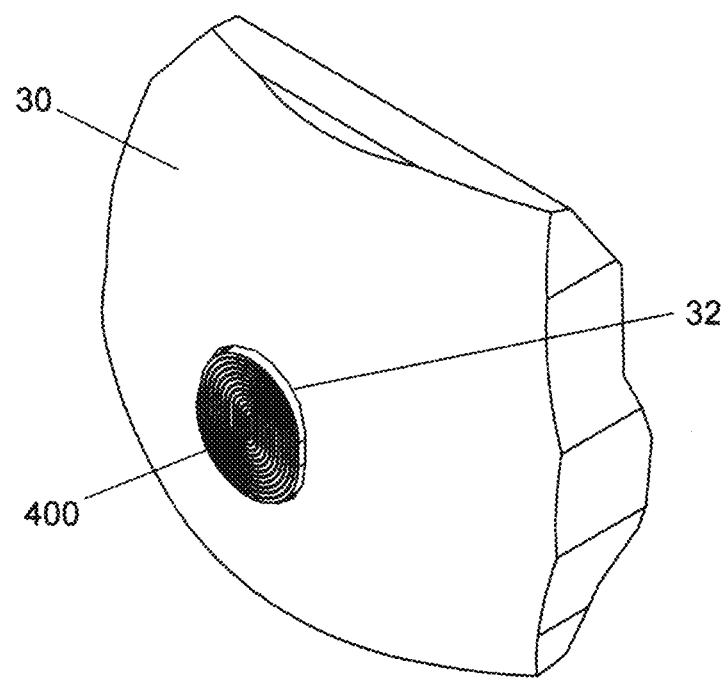
FIG. 30 is a perspective view of the condyle of FIG. 28 with the scaffold of FIG. 12 placed in the lesion.
Figure 31:
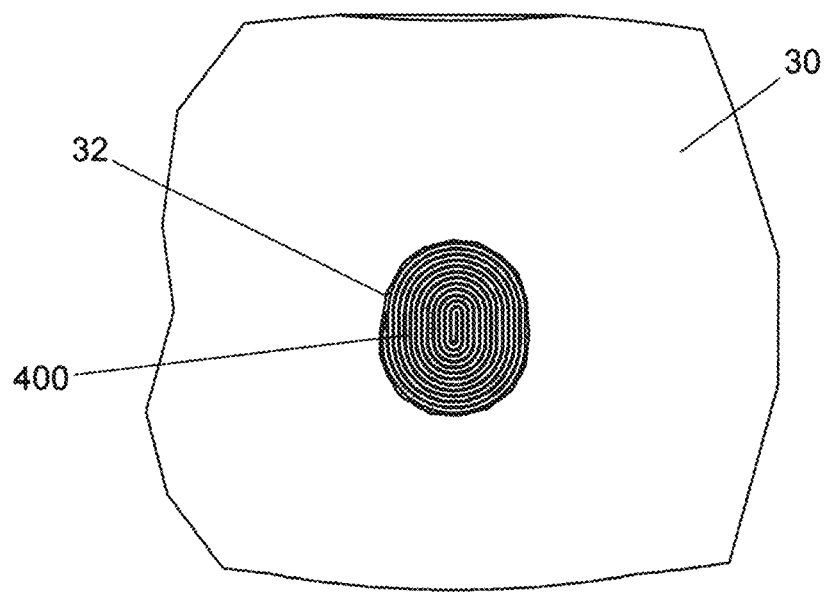
FIG. 31 is a side elevational view of the objects of FIG. 30.
Figure 32:
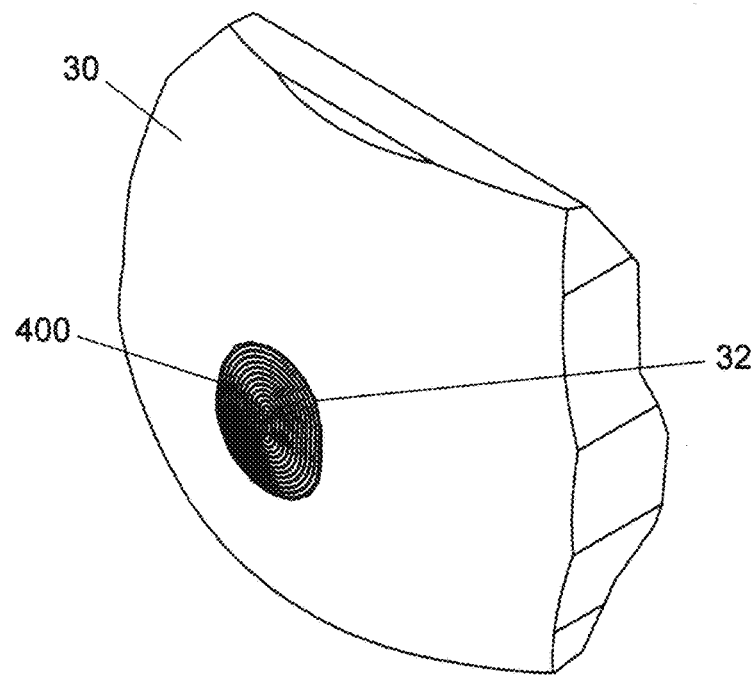
FIG. 32 is a perspective view of the condyle and scaffold of FIG. 32 with the scaffold contoured to match the condyle surface.
Figure 33:
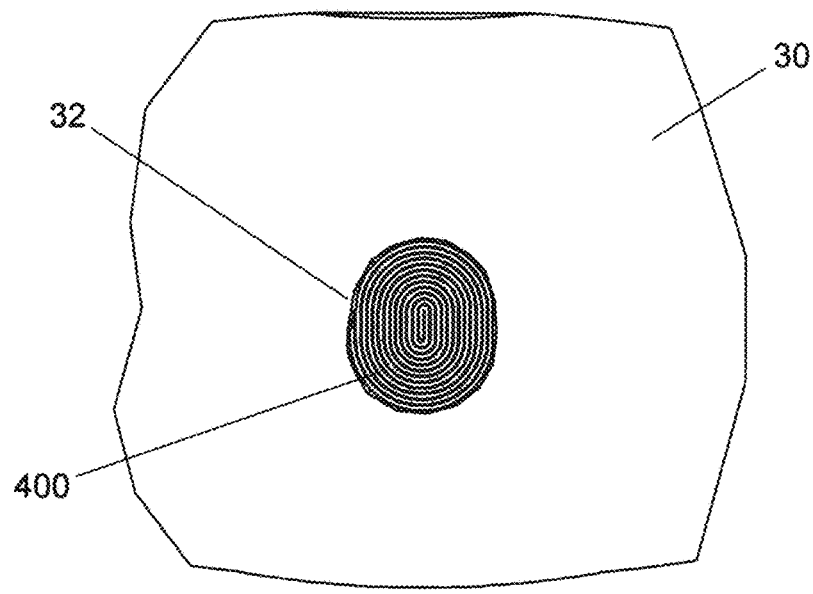
FIG. 33 is a side elevational view of the objects of FIG. 32.
Figure 34:
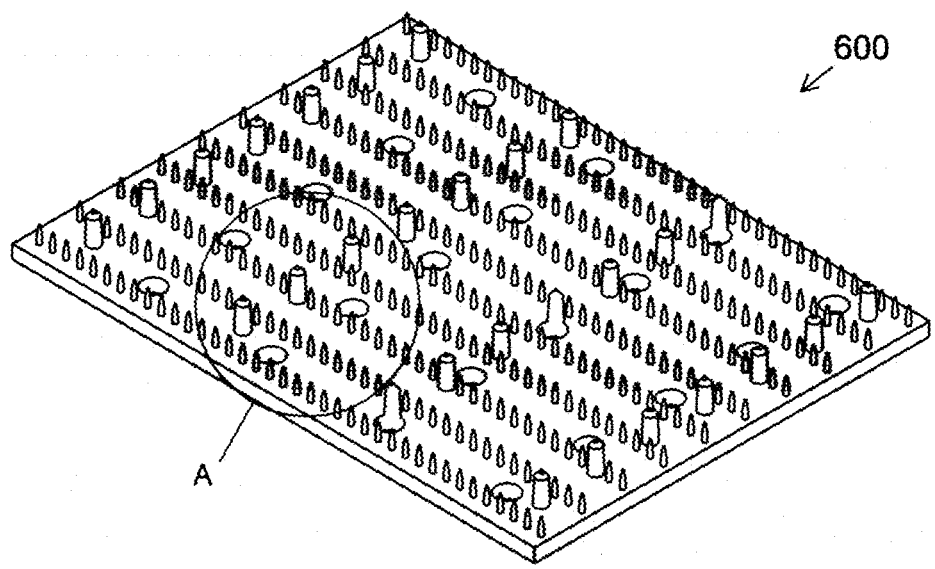
FIG. 34 is a perspective view of a lamella for an alternate embodiment lamellar scaffold of the present invention.
Figure 35:
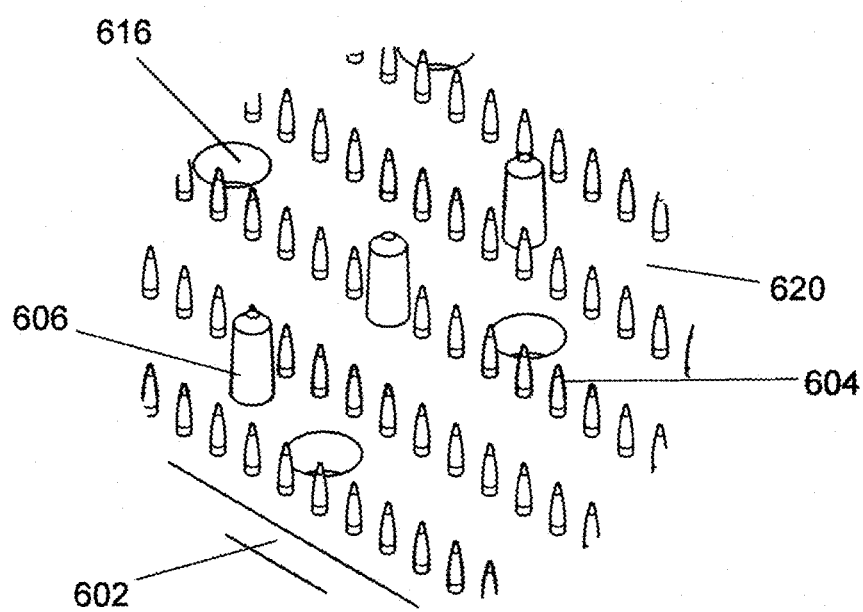
FIG. 35 is an expanded view of the objects of FIG. 34 at location A.
Figure 36:
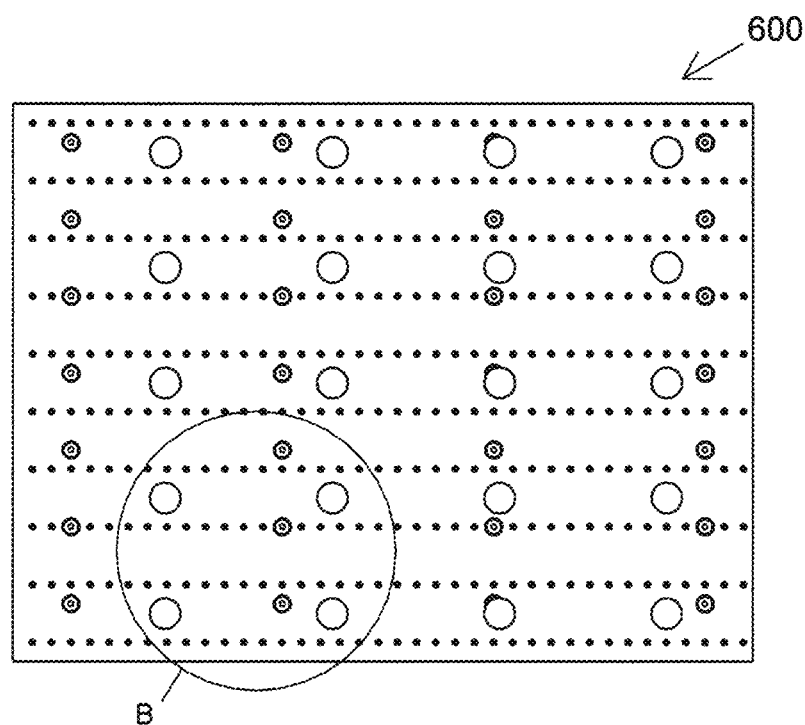
FIG. 36 is a plan view of the objects of FIG. 34.
Figure 37:
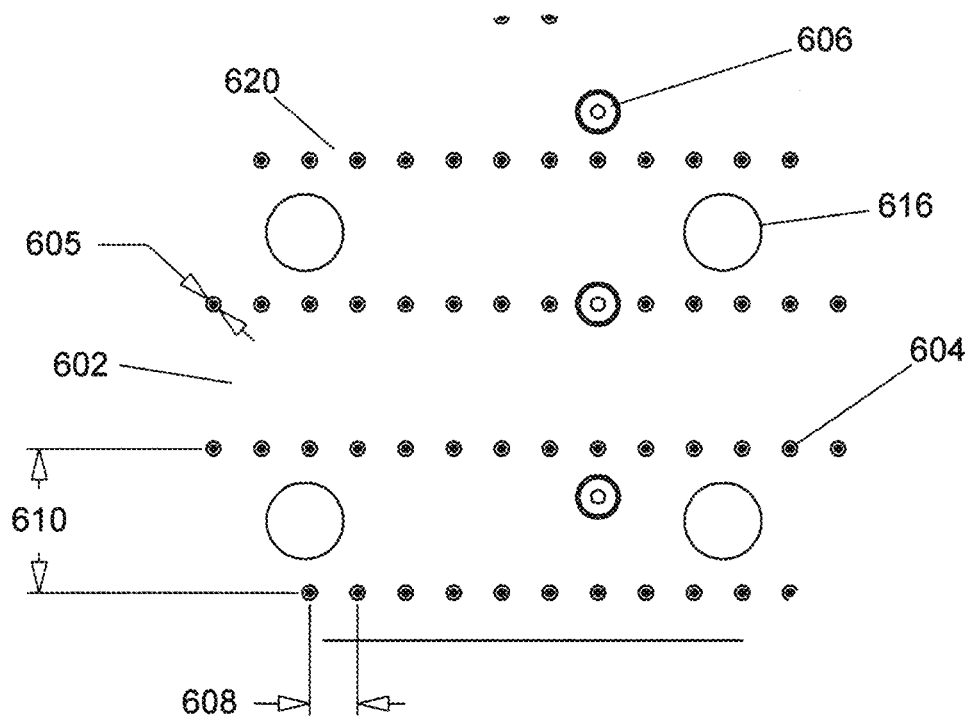
FIG. 37 is an expanded view of the objects of FIG. 36 at location B.
Figure 38:
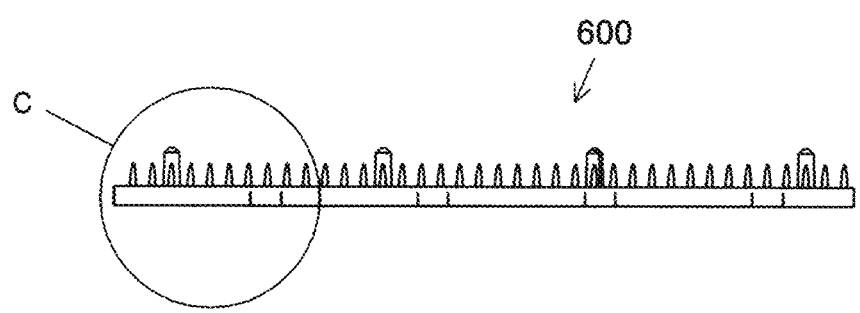
FIG. 38 is a side elevational view of the objects of FIG. 34.
Figure 39:
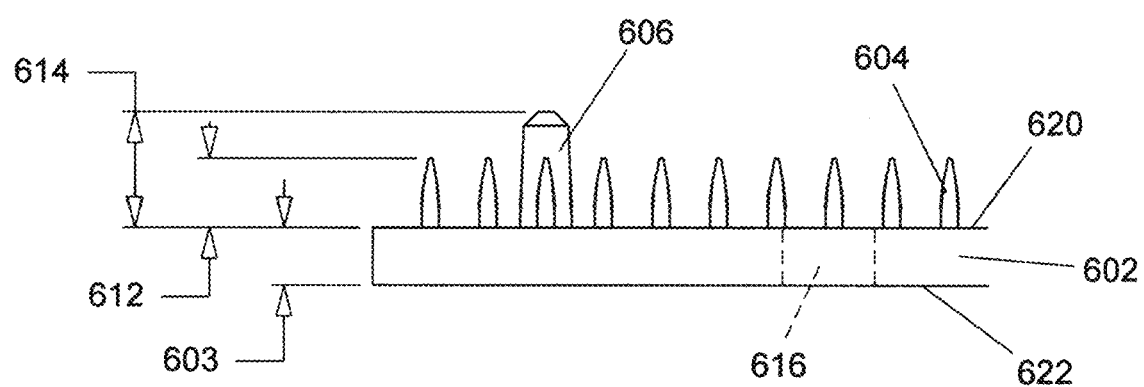
FIG. 39 is an expanded view of the objects of FIG. 38 at location C.
Figure 40:
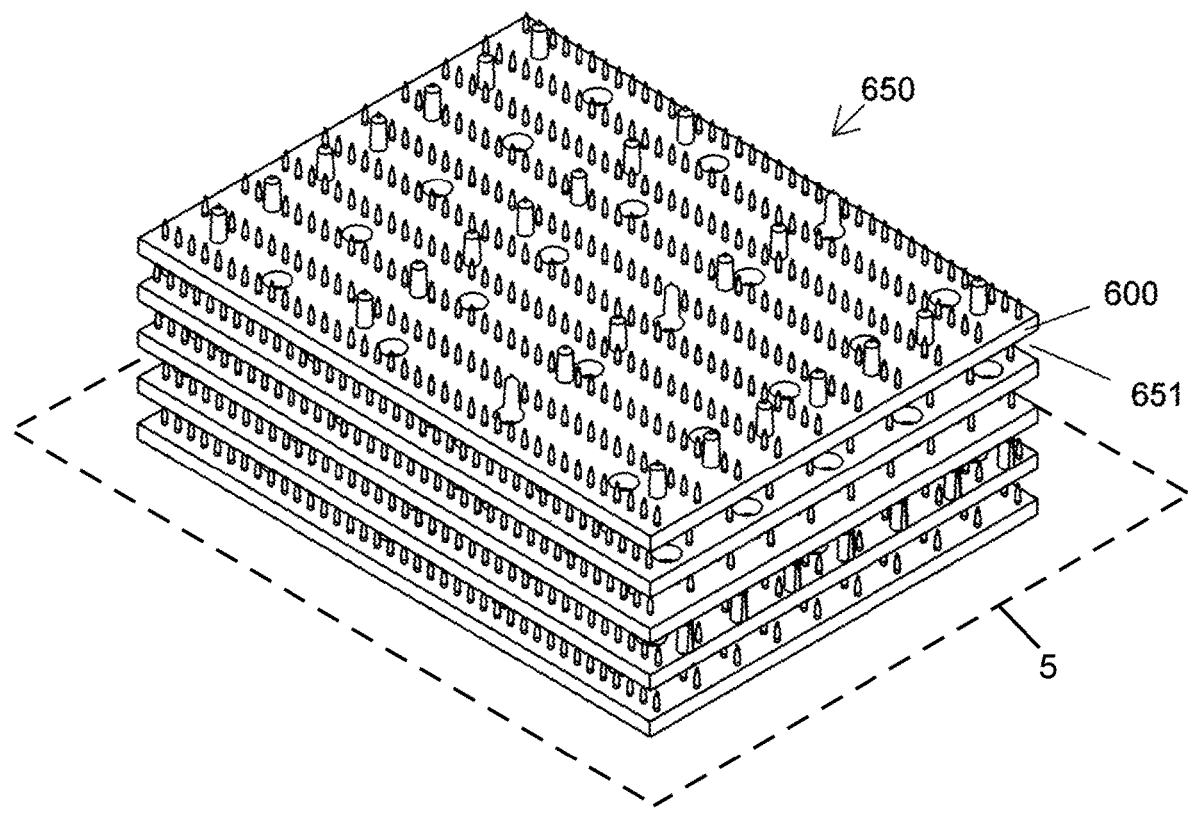
FIG. 40 is a perspective view of a segment of an alternate embodiment lamellar scaffold of the present invention using the lamella of FIG. 34.
Figure 41:
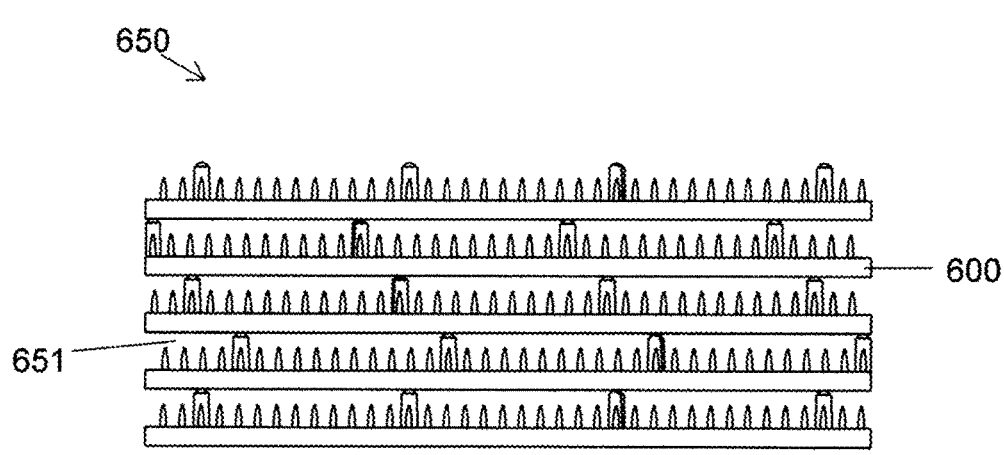
FIG. 41 is a side elevational view of the objects of FIG. 40.
Figure 42:
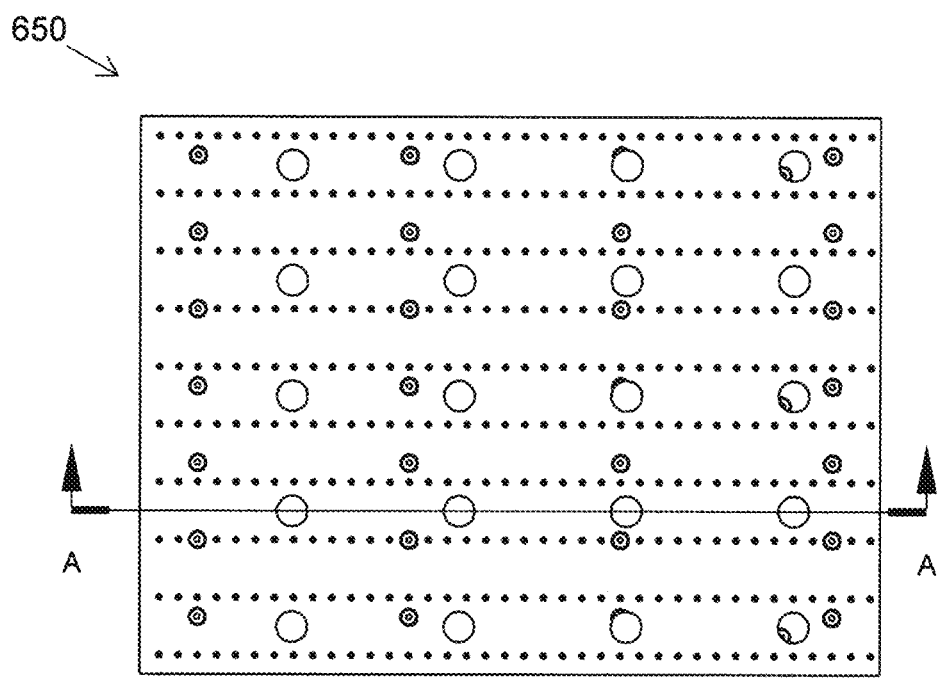
FIG. 42 is a plan view of the objects of FIG. 40.
Figure 43:
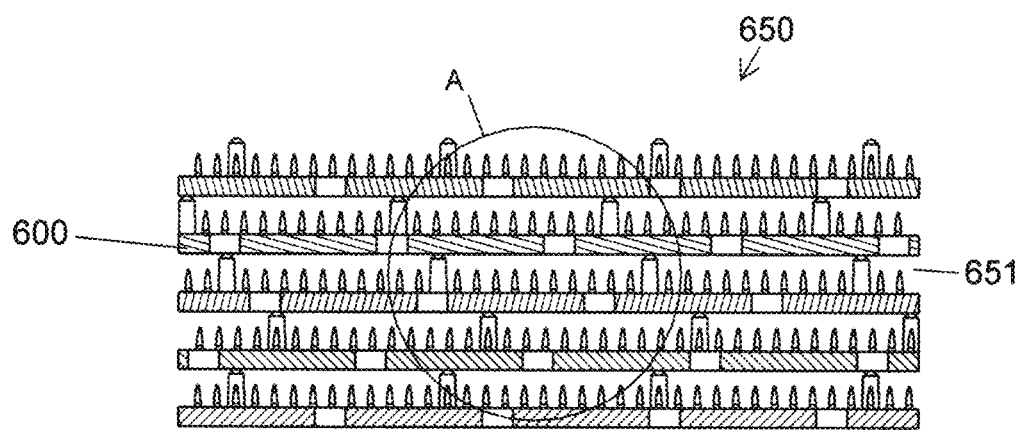
FIG. 43 is sectional view of the objects of FIG. 42 at location A-A.

In the articular cartilage defect treatment method of the present invention previously described, scaffold 500 was configured to match the shape of lesion 12. In an alternate repair method of the present invention the defect site is configured to match the shape of the scaffold used in the repair. Referring now to FIGS. 26 and 27, condyle 30 has formed thereon lesion 32 with recessed surface 34. The surgeon measures the size and depth of the lesion and selects a scaffold 400 (FIGS. 12 to 14) somewhat larger than the lesion. The surgeon removes calcified cartilage from surface 34 to expose underlying bone. Defect 32 is enlarged and configured as depicted in FIGS. 28 and 29, width 42 being slightly larger than width 402 of scaffold 400 (FIG. 12), and length 44 being slightly larger than length 404 of scaffold 400. Thickness 405 of scaffold 400 is greater than depth 38 of prepared lesion 34. Scaffold 400 is then positioned in defect 32 as depicted in FIGS. 30 and 31. Optionally, fibrin glue may be applied between the perimeter of scaffold 400 and the cartilage side walls of lesion 32. After the glue has set, scaffold 400 is contoured to match the shape of the articular surface of condyle 30.

Optionally, as with the previously described alternate method of treatment, the surgeon may aspirate bone marrow from a suitable location, with the bone marrow subsequently undergoing centrifuging to concentrate the stem cells and growth factors. Scaffold 400 is saturated with stem cells in the manner previously described, before being positioned in defect 32 as depicted in FIGS. 30 and 31. Also, as previously described, the surgeon may perform a microfracture procedure prior to the placement of scaffold 400 in the manner previously described.

Lamellar scaffolds of the present invention previously herein described are formed of lamellae that are perpendicular to the basal plane 5 of the scaffold. In other embodiments the lamellae are parallel to the basal plane 5 of the scaffold. A lamella 600 for a lamellar scaffold of the present invention in which the lamella are parallel to the basal plane 5 of the scaffold is depicted in FIGS. 34 through 39. Lamella 600 has an elongate flexible planar portion 602 with a first surface 620 and a second surface 622. First surface 620 has formed on it an array of nanofibers 604 and pedestals 606. Nanofibers 604 of basal diameter 605 are spaced distance 610 apart in a first direction, and distance 608 apart in a direction perpendicular to the first direction, distance 610 being greater than distance 608. Nanofibers 604 have a height 612 and pedestals 606 have a height 614, height 614 being greater than height 612. Distances 608 and 610, and heights 612 and 614 and the diametric profile of nanofibers 604 together are optimized to form a biomimetic cell culture substrate for the propagation of stem cells, or for the differentiation of stem cells into a desired cell type. Pedestals 606 are depicted as truncated cones. In other embodiments pedestals 606 may have elliptical, oval, or other cross-sections optimized for specific applications. Planar portion 602 has formed therein holes 616. Holes 616 may be round, elliptical, slots, or have curvilinear shapes. The configuration, size, number and placement of holes 616 may be optimized to favor a particular desired cell behavior.

Figure 44:
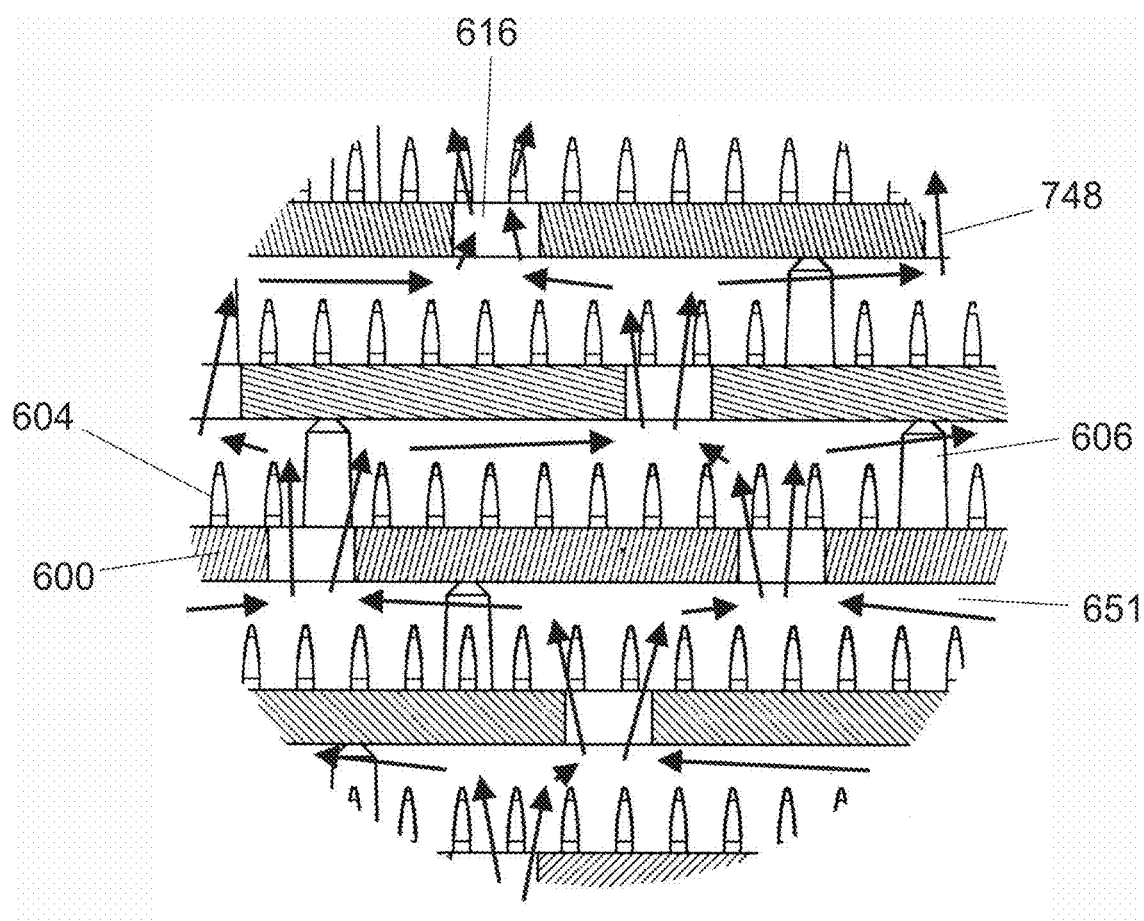
FIG. 44 is an expanded view of the objects of FIG. 43 at location A depicting the propagation of stem cells through the scaffold of FIG. 40.
Figure 45A:
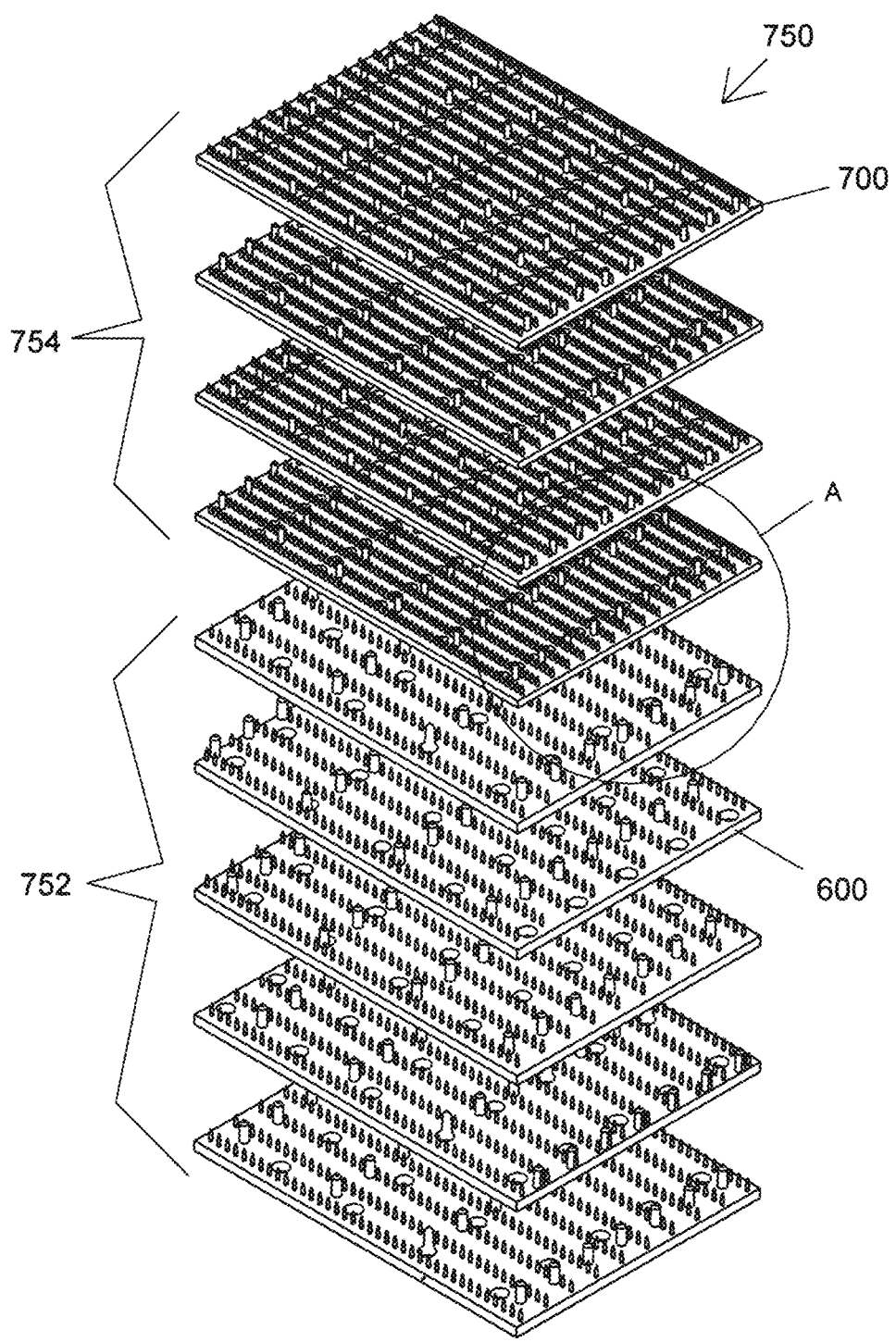
FIG. 45A is a perspective view of an alternate embodiment scaffold of the present invention.
Figure 45B:
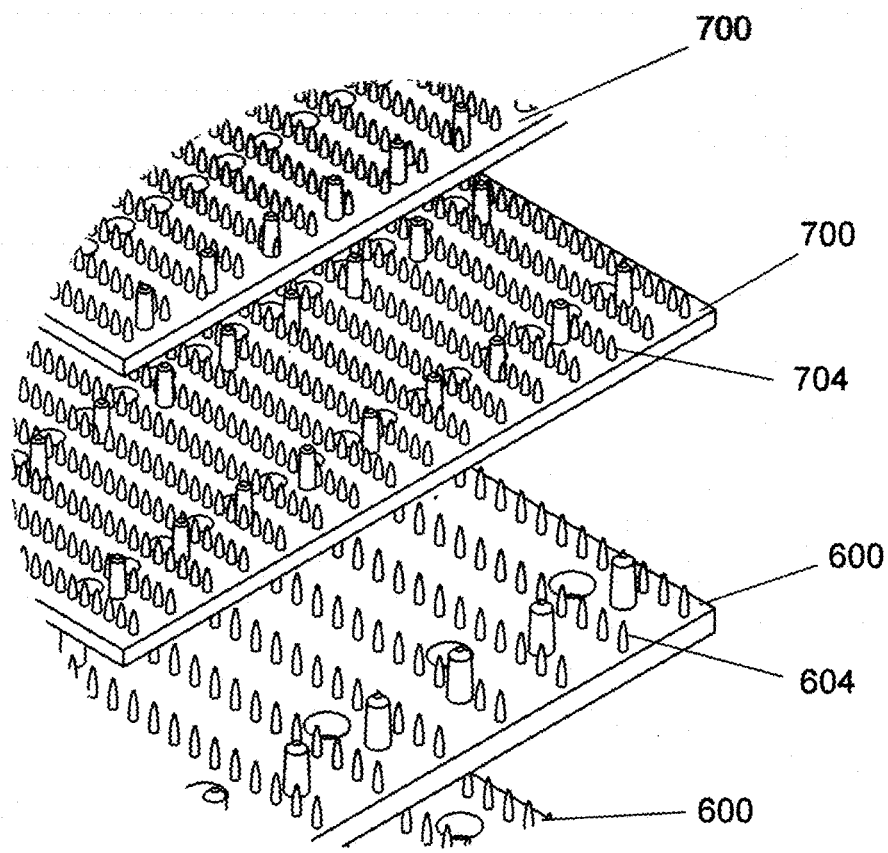
FIG. 45B is an expanded view of the objects of FIG. 45A at location A.

A lamellar scaffold 650 of the present invention with the lamellae parallel to the base 5 of the scaffold is diagrammatically depicted in FIGS. 40 through 43. Adjacent lamellae 600 have formed between them interlamellar spaces 651. Rows of nanofibers 604 in interlamellar spaces 651 form channels for the propagation of stem cells. As best seen in FIG. 44, these channels together with perforations 616 in lamellae 600 form a labyrinth through which cellular propagation, indicated by arrows 648, may occur. As in previously described lamellar scaffolds of the present invention, the geometry of nanofibers 604, and the geometry of the arrays formed of nanofibers 604 may be optimized for maintaining the stemness of stem cells populating scaffold 650, or may induce their differentiation into desired cell types. Scaffold 650 is formed of a plurality of lamellae 600 all of which have a single matrix geometry and that have nanofibers 604 of a single constant configuration throughout. In other embodiments of the present invention a scaffold may be formed wherein a first portion of the lamella stack forming the scaffold is formed of lamellae having a first array pattern and first nanofiber configuration optimized for the propagation of a first cell type, and a second portion of the stack formed of lamellae having a second array pattern and second nanofiber configuration optimized for the propagation of a second cell type. Such a scaffold of the present invention is depicted in FIGS. 45A and 45B. Scaffold 750 has a first portion 752 formed of lamellae 600, and a second portion 754 formed of lamellae 700. As best seen in FIG. 45B, nanofibers 604 of lamellae 600 differ in configuration from fibers 704 of lamellae 700. Also, the spacing of nanofibers 604 within the array of lamellae 600 differs from the spacing of nanofibers 704 within the array of lamellae 700. Lamellae 600 may have nanofibers 604 and the arrays of which they are formed optimized for the differentiation of stem cells populating region 752 of scaffold 750 into a first cell type, such as, for instance osteocytes. Lamellae 700 of region 754 of scaffold 750 may be optimized for the differentiation of stem cells populating region 754 of 750 into a second cell type, such as, for instance, chondrocytes. Indeed, by creating scaffolds with regions that favor the propagation of selected cell types scaffolds of the present invention may regenerate stratified tissue structures like hyaline cartilage.

Unlike prior art fibrous scaffolds, those of the present invention are able to support a compressive load without permanent deformation. Prior art fibrous scaffolds like those described by Arinzeh in US 2016/0354515 permanently deform when subjected to a load, resulting in incomplete filling of a defect, or flattening of the exposed surface contour. In contrast, lamellar scaffolds of the present invention are load bearing. They maintain their size and shape under load thereby allowing complete filling of a defect and the maintaining of contours of the exposed surface. Additionally, lamellar scaffolds of the present invention are resilient, that is, they elastically deform when subjected to a load and spring back when the load is removed or lessened.

Figure 46:
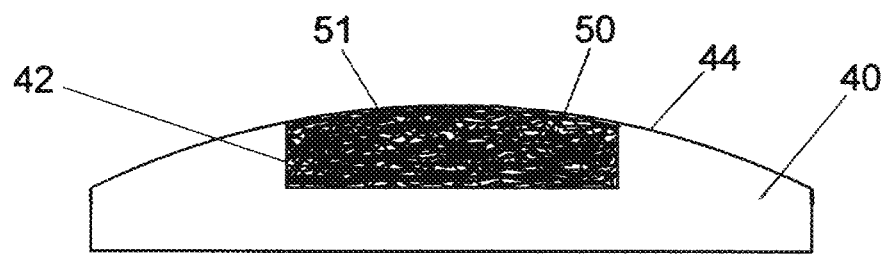
FIG. 46 is a diagrammatic sectional view of a prior art fibrous scaffold placed in a defect in an articular surface.
Figure 47:
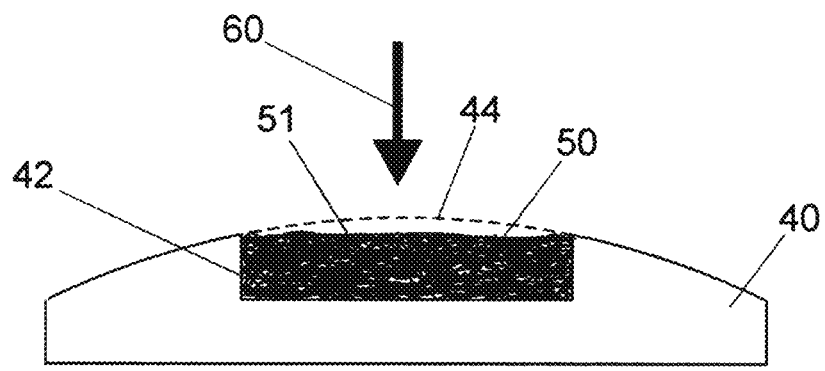
FIG. 47 depicts the objects of FIG. 46 with the scaffold subjected to a compressive load.
Figure 48:
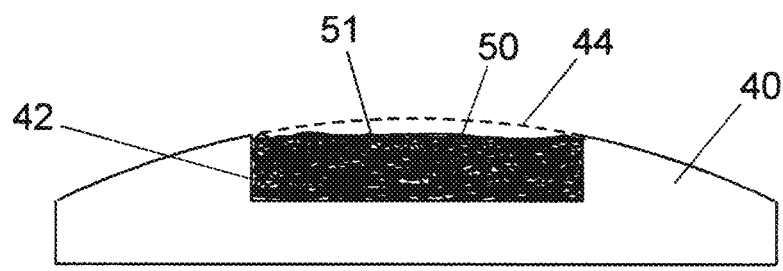
FIG. 48 depicts the objects of FIG. 46 with after the compressive load of FIG. 47 is removed.

Referring now to FIGS. 46 through 48 that depict a prior art fibrous scaffold 50 placed in defect 42 in condyle 40, initially, as depicted in FIG. 46, the profile of exposed surface 51 of scaffold 50 matches the profile of surface 44 of condyle 40. FIG. 47 depicts condyle 40 and scaffold 50 when scaffold 50 is subjected to a compressive load, shown as arrow 60. Scaffold 50 is compressed by the load such that surface 51 of scaffold 50 is flattened and displaced from surface 44 of condyle 40. FIG. 48 depicts scaffold 50 and condyle 40 after the compressive load is removed. Surface 51 of scaffold 50 remains flattened and displaced from the profile 44 of the surface of condyle 40. This will result in incomplete filling of lesion 42 as scaffold 50 is replaced by fibro cartilage. Importantly, with scaffold 50 compressed as shown, cells developing within scaffold 50 are not subjected to the shear stresses that enhance cell development. Specifically, because scaffold 50 is not subjected to repetitive compressive loading, cells developing within scaffold 50 will not experience the shear stresses required to optimally develop a tissue structure in which the cells are configured and aligned to resist a compressive load.

Figure 49:
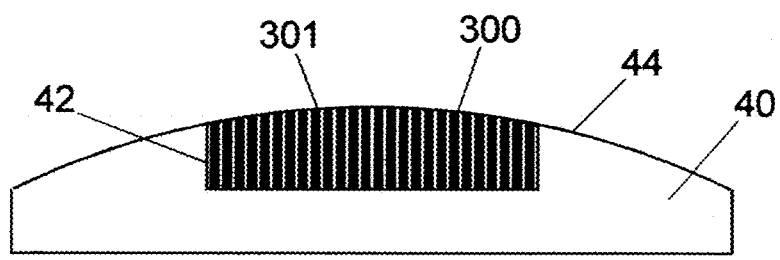
FIG. 49 is a diagrammatic sectional view of a lamellar scaffold of the present invention placed in a defect in an articular surface.
Figure 50:
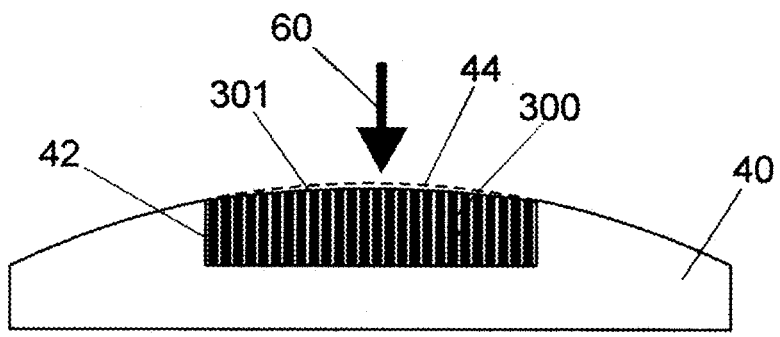
FIG. 50 depicts the objects of FIG. 49 with the scaffold subjected to a compressive load.
Figure 51:
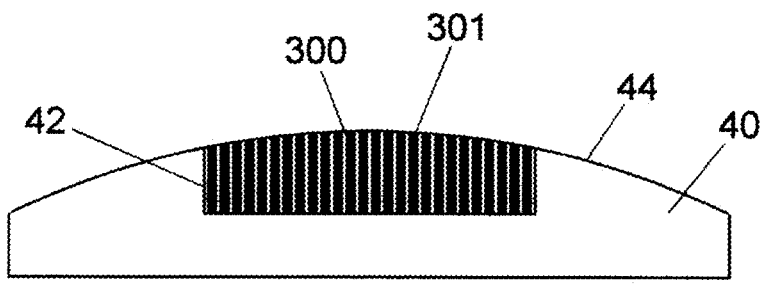
FIG. 51 depicts the objects of FIG. 50 after the compressive load of FIG. 50 is removed.

In contrast, highly ordered, lamellar scaffolds of the present invention are resilient, and capable of supporting a compressive load without appreciable permanent deformation. Referring now to FIGS. 49 through 51 depicting lamellar scaffold 300 of the present invention positioned in defect 42 in condyle 40, in FIG. 49 the contour of surface 301 of scaffold 300 matches the contour of surface 44 of condyle 40. Applying a compressive load, shown as arrow 60 depicted in FIG. 50, causes slight deformation of scaffold 300 such that the contour of surface 301 of scaffold 300 is slightly displaced from the contour of surface 44 of condyle 40. When compressive load 60 is removed (see FIG. 51) scaffold 300 returns to its original size and shape with surface 301 of scaffold 300 matching the contour of surface 44 of condyle 40. Repetitive cyclic loading of scaffold 300 subjects developing cells within it to shear stresses that enhance cell development and that create aligned cellular structures that are optimal for compressive strength in the regenerated tissue.

While the use of lamellar biomimetic scaffolds of the present invention has been described with reference to defects in condylar articular cartilage, this is for example only and is not limiting of the scope of this invention.

Lamellar scaffolds of the present invention may be used for the regeneration or augmentation of virtually any bone or soft tissue.

Tissue augmentation is well known in the art. Products such as the Regeneten BioInductive Implant by Smith and Nephew, Inc. (Andover, Mass.), Allopatch HD by Conmed, Inc. (Utica, N.Y.), and the DX Reinforcement Matrix by Arthrex, Inc. (Naples, Fla.) are used to treat deficiencies in soft tissue. Among other uses, the products are frequently used to treat rotator cuff disease including partial thickness tears. The products are furnished in flexible sheet-like form and are applied as a patch to the soft tissue at the site of the pathology. The patch provides mechanical bracing to the site, and serves as a scaffold for the growth of tendon-like tissue as it is absorbed.

Figure 52:
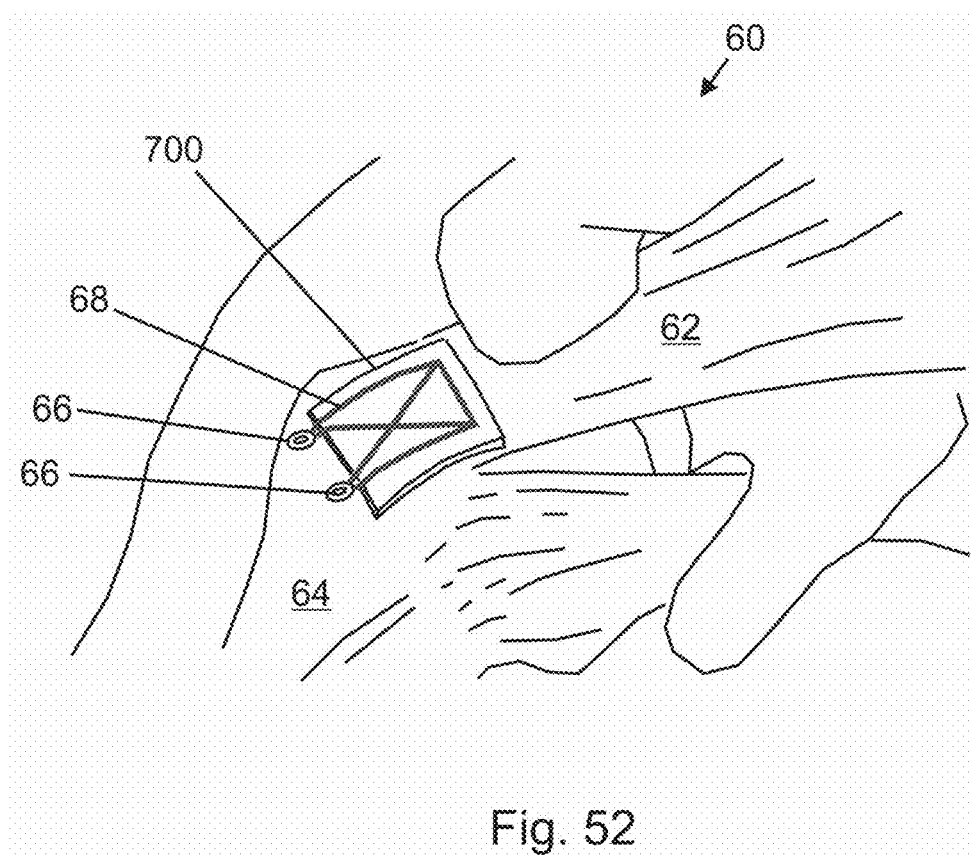
FIG. 52 is a diagrammatic perspective view of a lamellar scaffold of the present invention applied for tissue augmentation in a rotator cuff repair.
Figure 53:
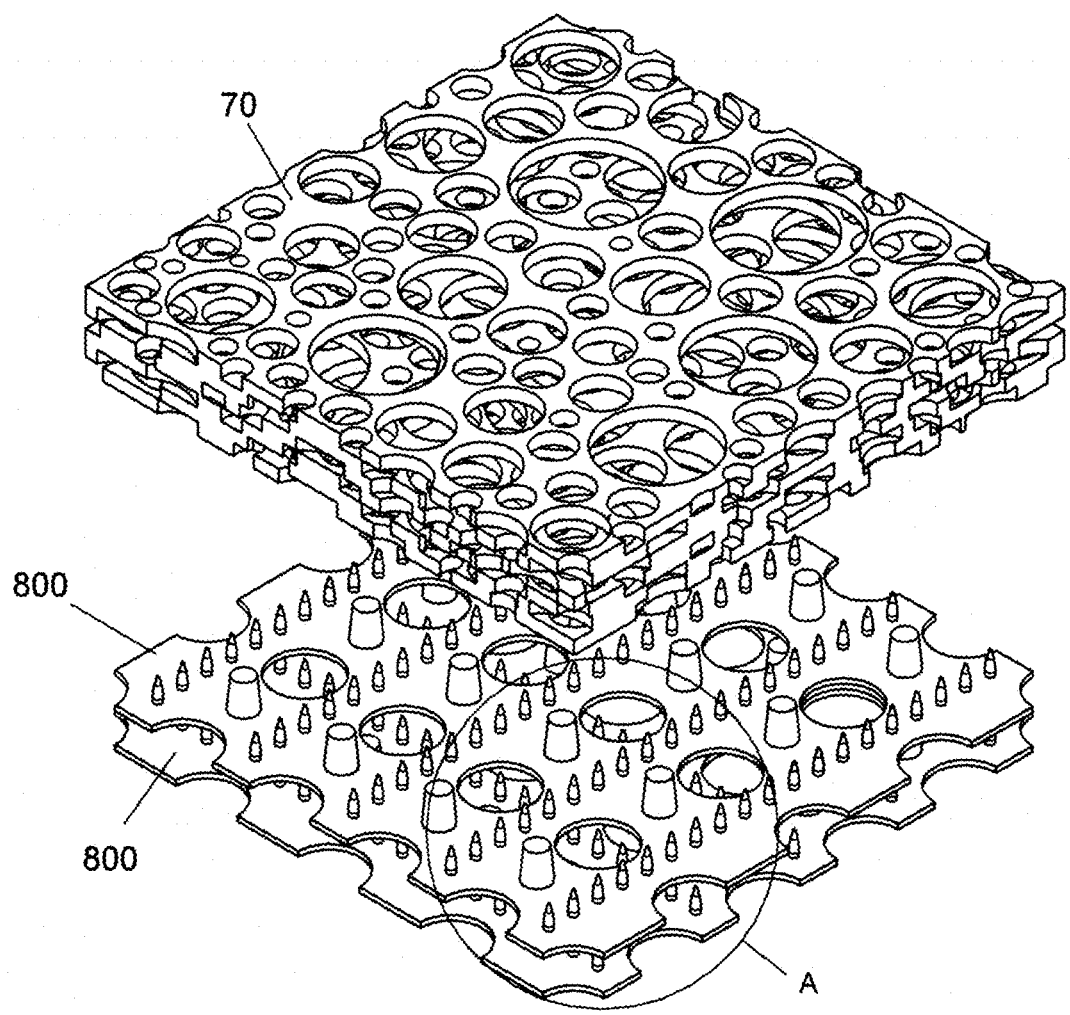
FIG. 53 is an exploded view of an alternate embodiment of the present invention wherein a scaffold of the present invention supplements a prior art scaffold.
Figure 54:
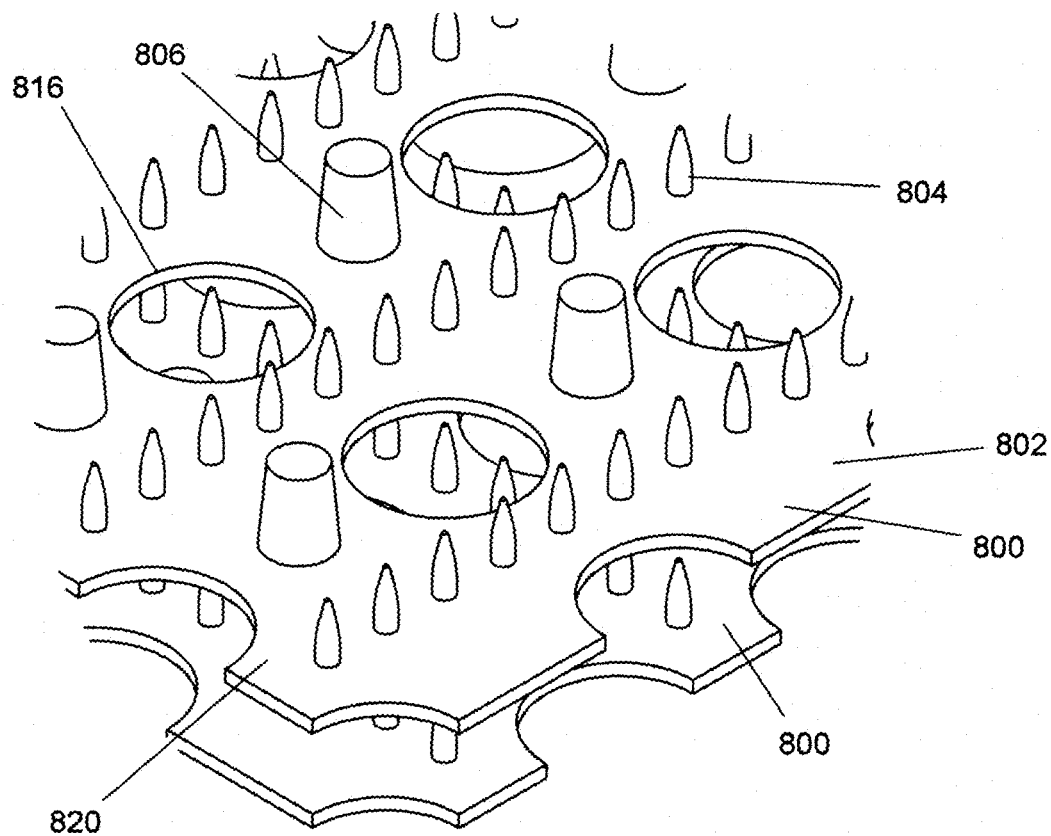
FIG. 54 is an expanded view of the objects of FIG. 53 at location A.
Figure 55:
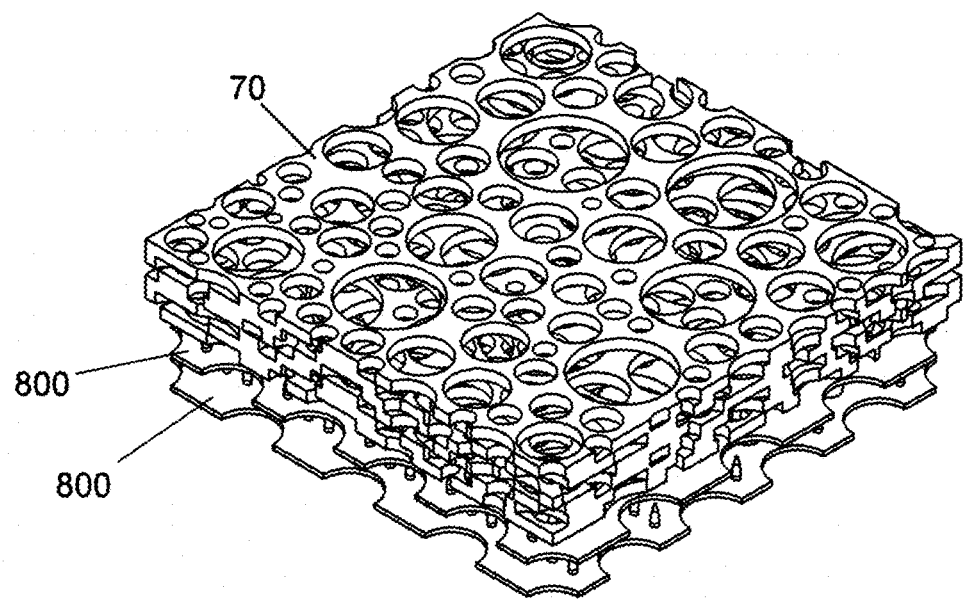
FIG. 55 is a perspective view of the objects of FIG. 53 assembled for use.
Figure 56:
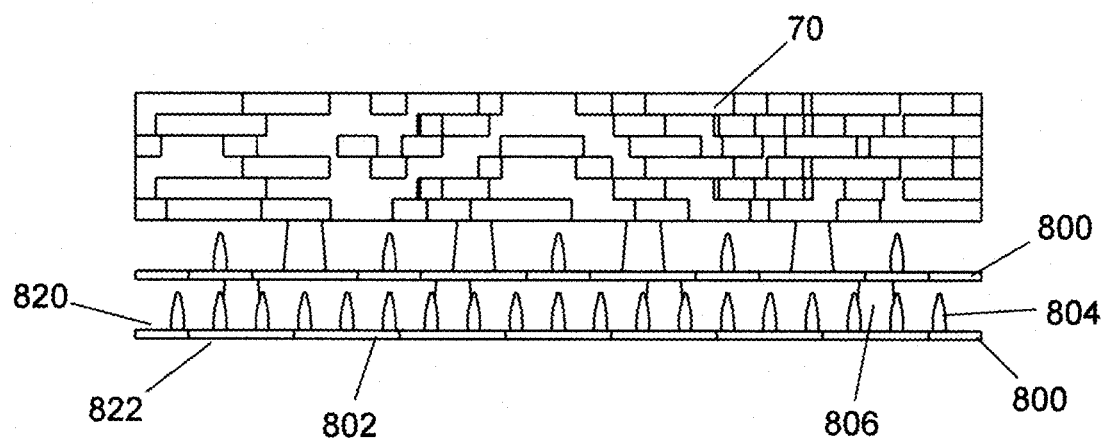
FIG. 56 is a side elevational view of the objects of FIG. 55.

Biomimetic lamellar scaffolds of the present invention may be used in this manner for tissue augmentation. For instance, FIG. 52 depicts a scaffold 700 used for augmentation of rotator cuff 62 in the repair of a tear of cuff 62. A tear occurs when the lateral attachment of cuff 62 is separated from humerus 64. Cuff 62 is reattached to humerus 64 using suture 68 and suture anchors 66. The reattachment technique depicted is referred to as a "double-row" repair since sutures 68 are passed over cuff 62 from a medial row of anchors placed under cuff 62 to a second row 66 of anchors lateral to the edge of cuff 62. Sutures 68 compress the lateral portion of cuff 62 against a prepared portion of humerus 64. The lateral portion of cuff 62 reattaches itself to the humerus. If the lateral portion of the cuff is damaged by detachment from humerus 64, augmentation of cuff 62 is desirable to ensure success of the procedure. As depicted in FIG. 52, lamellar scaffold 700 is compressed against cuff 62 by sutures 68. While cuff 62 is reattaching to humerus 64, stem cells from cuff 62 propagate into scaffold 700 creating a supplemental layer of ligamentous tissue as scaffold 700 is absorbed. This results in a more secure reattachment with a decreased likelihood of re-injury.

Commercially available regenerative tissue scaffold patches for tissue augmentation may be formed with an acellular collagen scaffold and preserved vascular channels that enable repopulation and revascularization by host tissue. Typical of a matrix of this type is the GraftJacket from Wright Medical (Memphis, Tenn.). The GraftJacket is a human dermal collagen matrix that may be readily incorporated into the body. The material is essentially acellular and is treated with a proprietary process to preserve the intact matrix including vascular channels. The scaffold may be used to reinforce primary soft-tissue repairs throughout the body. After preparing a site for augmentation using the matrix, the scaffold is secured in place using sutures, staples, or fibrin glue, among other methods. The performance of scaffolds of this type may be enhanced by the addition of a biomimetic scaffold of the present invention. Specifically, one or more lamella with nanofiber matrices optimized for the propagation of stem cells may be positioned between the prepared site and the dermal collagen matrix to enhance the flow of stem cells into the matrix. FIGS. 53 through 56 diagrammatically depict a portion of a biomimetic scaffold formed of lamellae 800 positioned adjacent to collagen matrix 70, lamellae 800 being parallel to the plane of matrix 70. Lamellae 800 are alike in construction to lamella 600 (FIGS. 34 through 39) in all aspects of form and function having a planar portion 802, ordered arrays of nanofibers 804, pedestals 806 and perforations 816. Perforations 816 may comprise a larger portion of the surface area of planar portion 802 than perforations 816 of lamella 800 so as to increase the ease of flow of stem cells into and through the biomimetic scaffold formed of lamellae 800. External signaling provided by biomimetic arrays of nanofibers 804 to stem cells entering the scaffold portion formed by lamellae 800 may increase the differentiation of those cells into the types desired to populate matrix 70.

Figure 57:
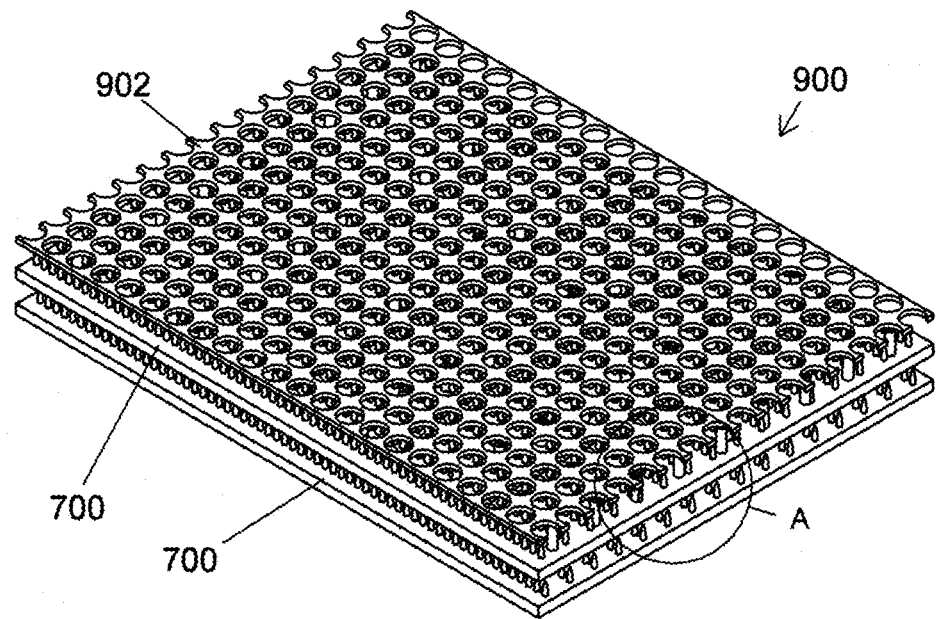
FIG. 57 is a perspective view of an alternate embodiment lamellar scaffold of the present invention comprising a structural element for enhanced strength and ease of fixation.
Figure 58:
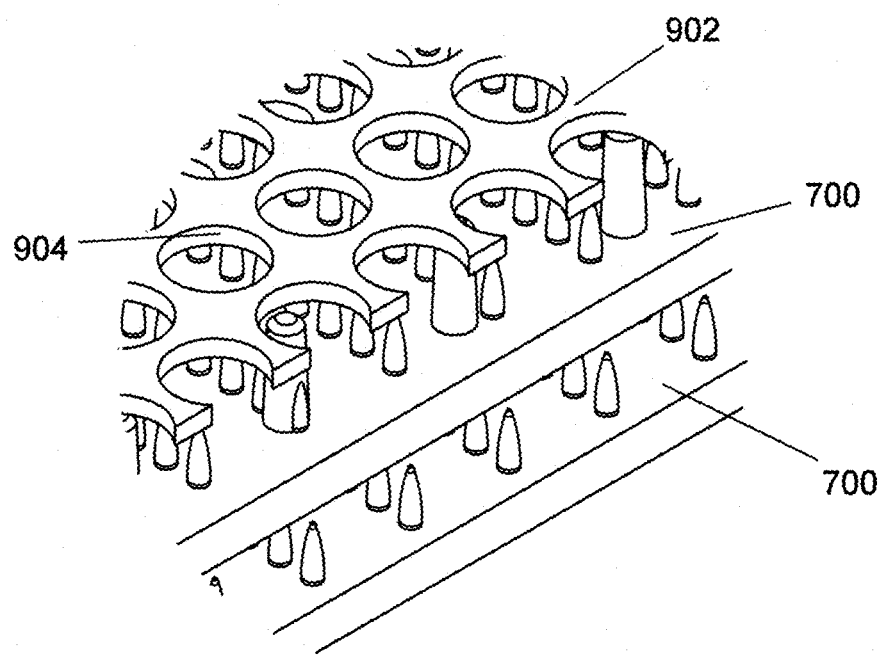
FIG. 58 is an expanded view of the objects of FIG. 57 at location A.

In another embodiment lamellar scaffold intended primarily for repairing or augmenting soft tissue structures, a porous layer of bioabsorbable material is added to the top surface of the scaffold to increase the strength of the scaffold and to aid in fixation of the scaffold at the treatment site. Referring now to FIGS. 57 and 58, scaffold 900 is formed of a plurality of lamellae 700 with bioabsorbable element 902 positioned adjacent to the top-most lamella 700. Element 902 has a plurality of perforations 904 that allow communication between the interlamellar spaces of scaffold 900 and the surrounding environment. As depicted in FIGS. 57 and 58 element 902 ends at the margins of lamellae 700. In other embodiments element 902 extends beyond the margins so that scaffold 900 can be affixed at the treatment site using sutures or bioabsorbable staples without perforating the body of the scaffold. As depicted scaffold 900 has lamellae 700 oriented parallel to the basal plane of the scaffold. In other embodiments comprising element 902 the lamellae are perpendicular to the basal plane of the scaffold. Element 902 may be formed of any bioabsorbable material having suitable strength and absorption properties.

Figure 59:
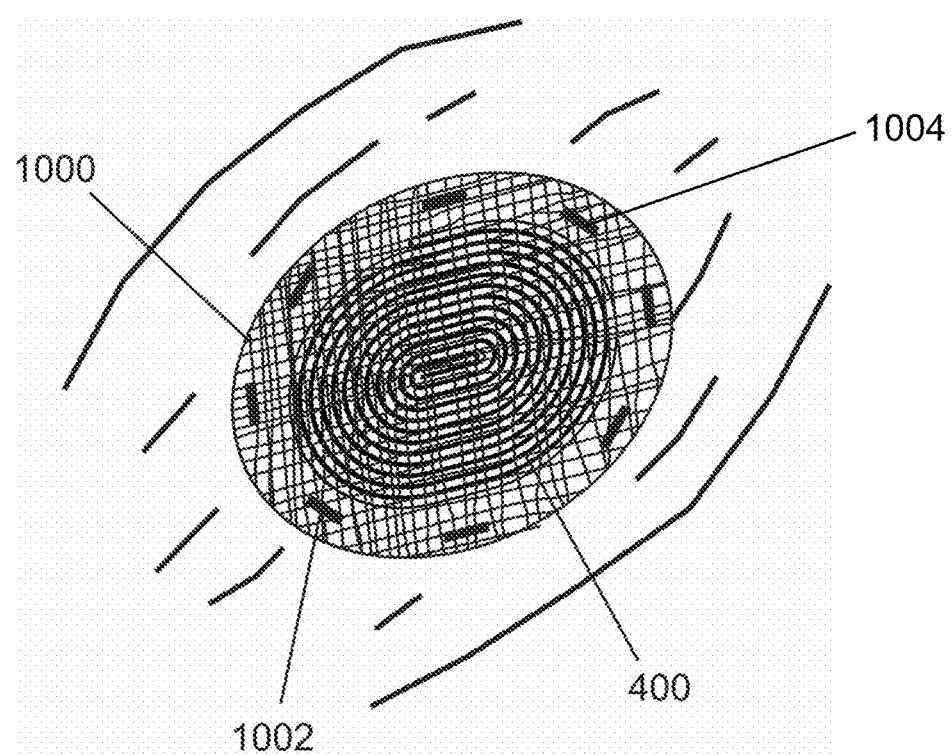
FIG. 59 depicts a lamellar scaffold of the present invention affixed to a soft tissue structure for augmentation thereof.
Figure 60:
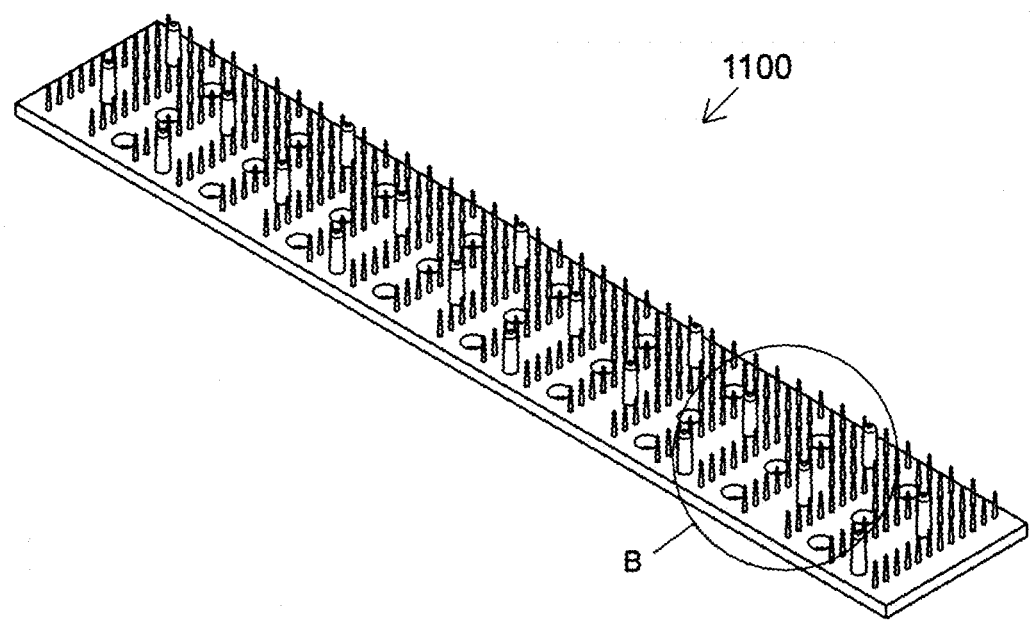
FIG. 60 is a perspective view of a lamella for an alternate embodiment lamellar scaffold of the present invention.
Figure 61:
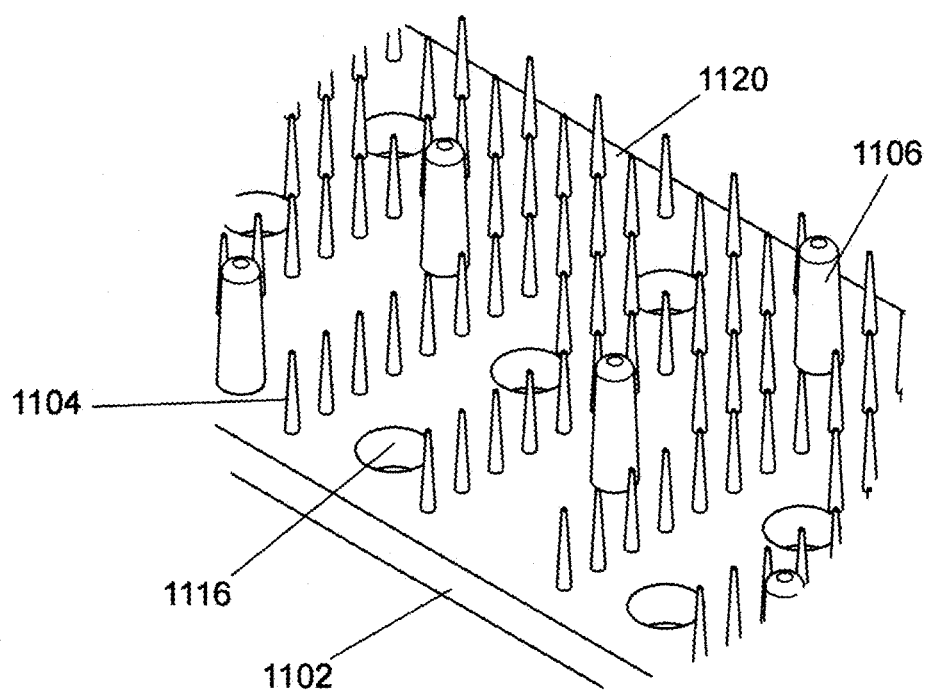
FIG. 61 is an expanded view of the objects of FIG. 60 at location B.
Figure 62:
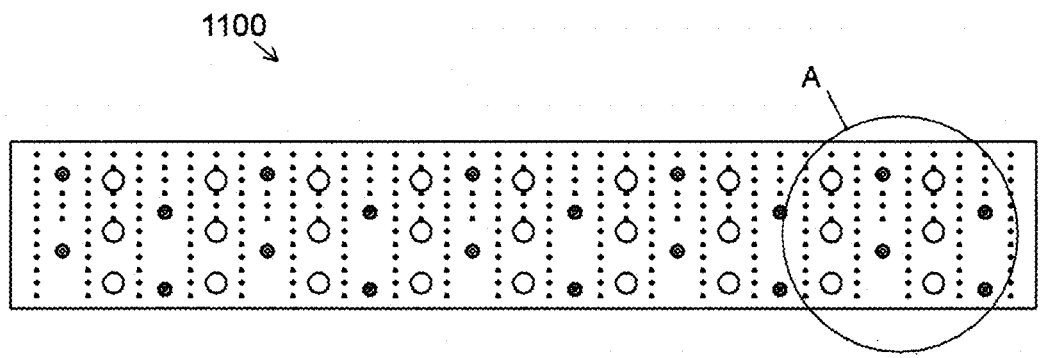
FIG. 62 is a plan view of the objects of FIG. 60.
Figure 63:
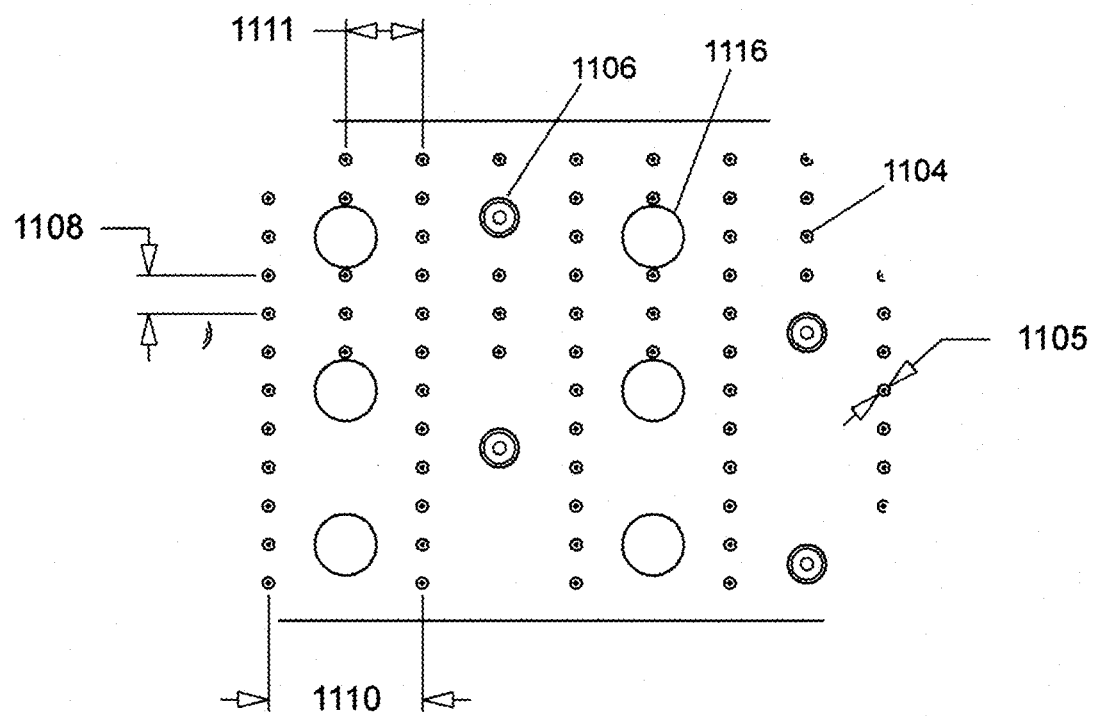
FIG. 63 is an expanded view of the objects of FIG. 62 at location A.
Figure 64:
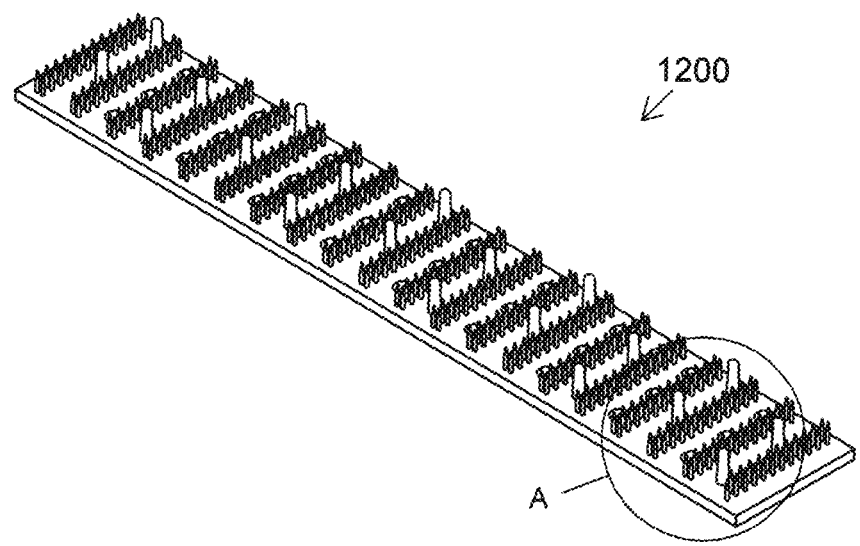
FIG. 64 is a perspective view of a lamella for an alternate embodiment lamellar scaffold of the present invention.
Figure 65:
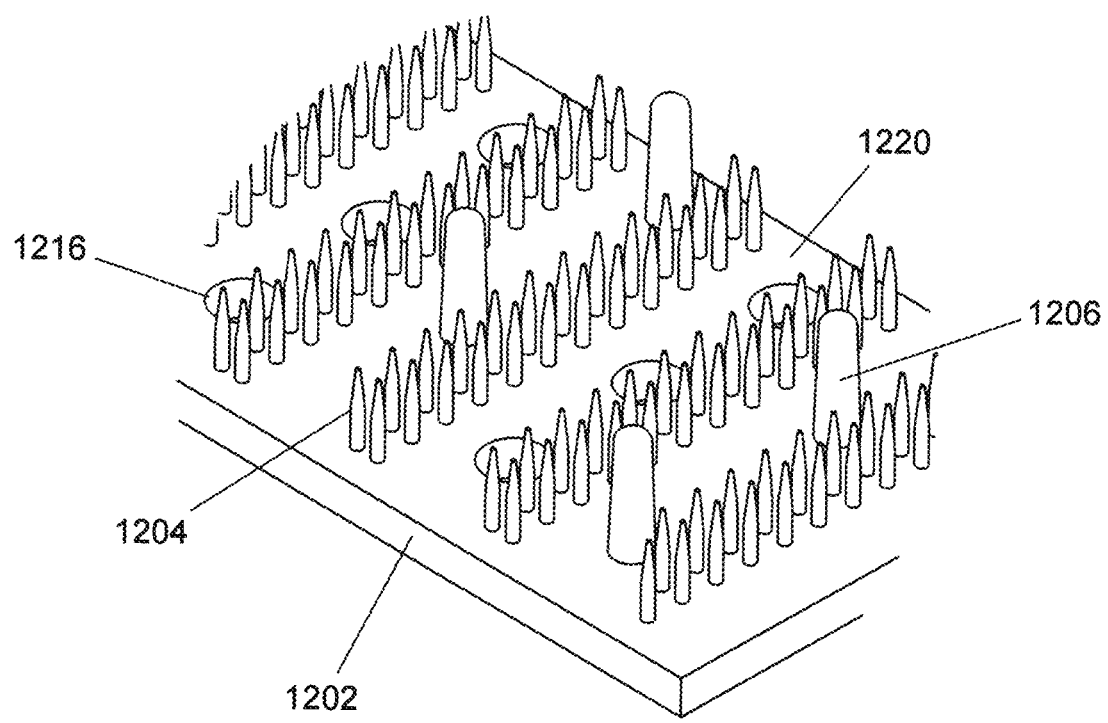
FIG. 65 is an expanded view of the objects of FIG. 64 at location A.
Figure 66:
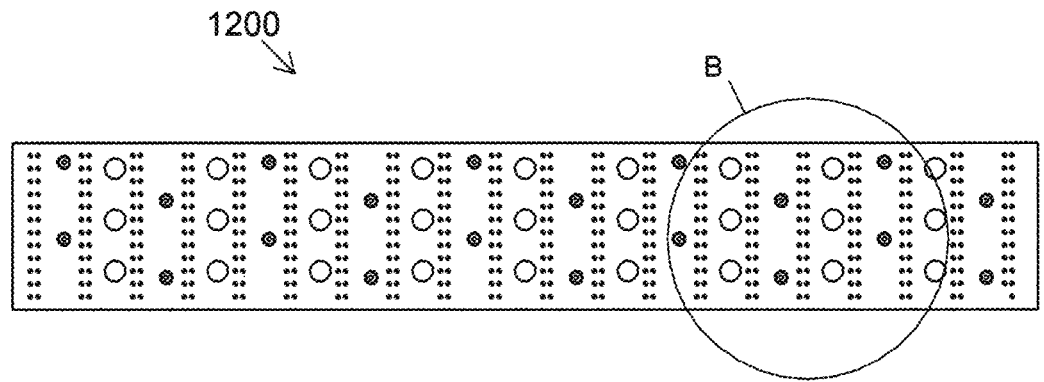
FIG. 66 is a plan view of the objects of FIG. 64.
Figure 67:
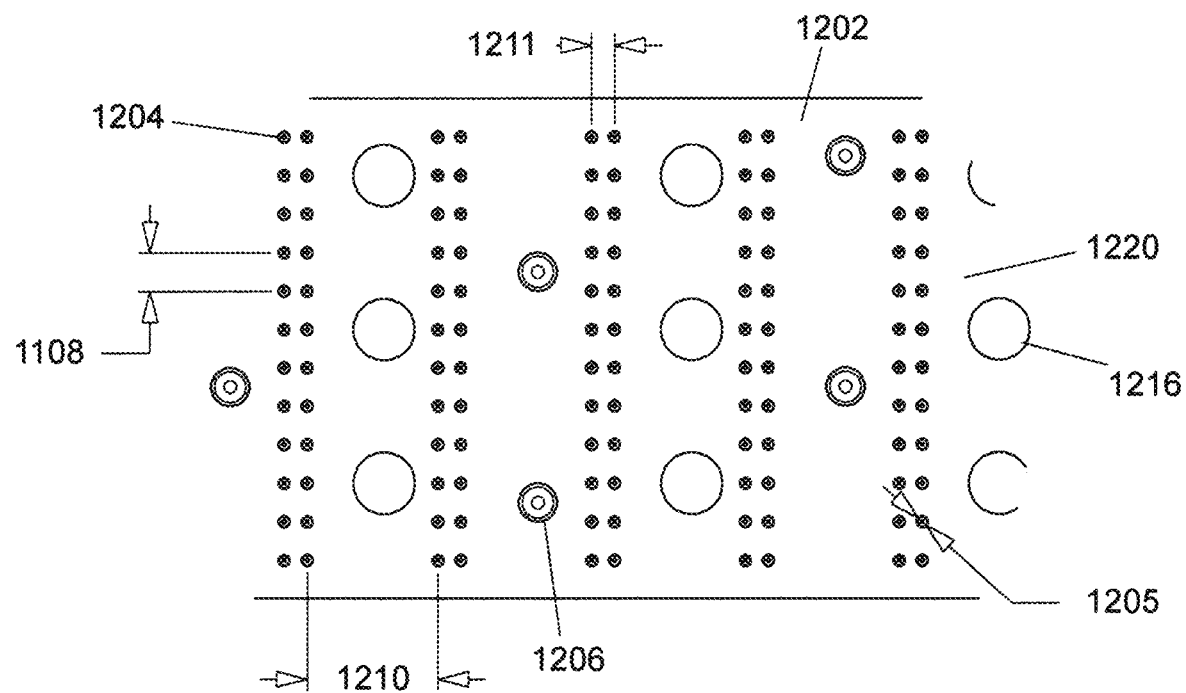
FIG. 67 is an expanded view of the objects of FIG. 66 at location B.
Figure 68:
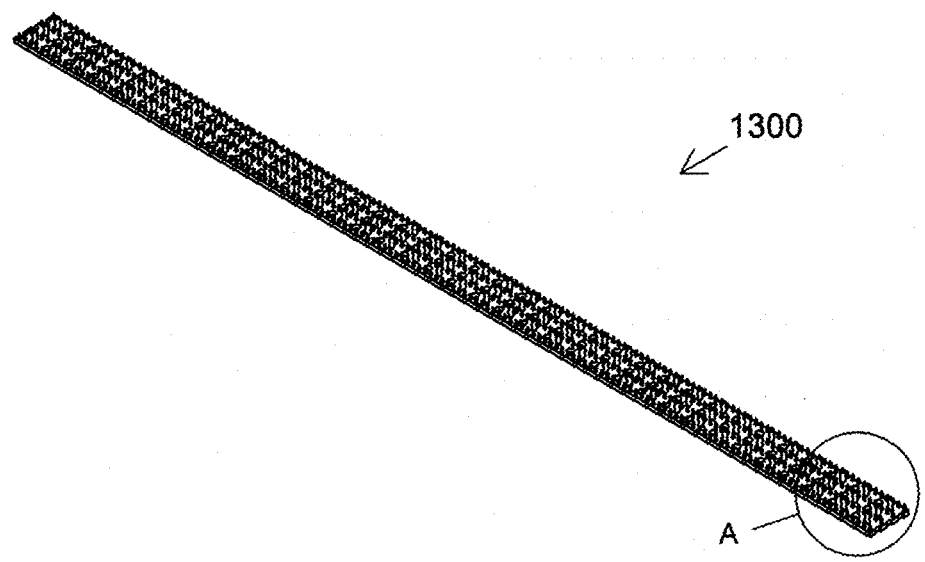
FIG. 68 is a perspective view of a lamella for an alternate embodiment scaffold of the present invention for forming elongate tissue structures.
Figure 69:
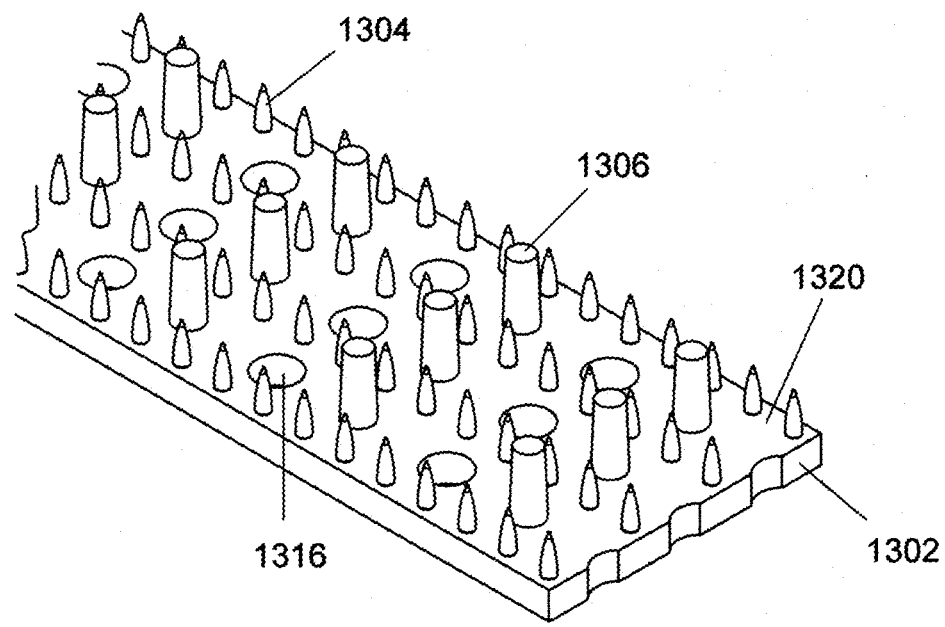
FIG. 69 is an expanded view of the objects of FIG. 68 at location A.
Figure 70:
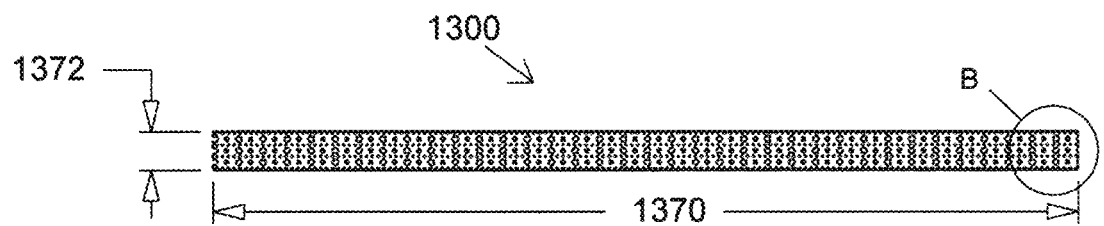
FIG. 70 is a plan view of the objects of FIG. 68.
Figure 71:
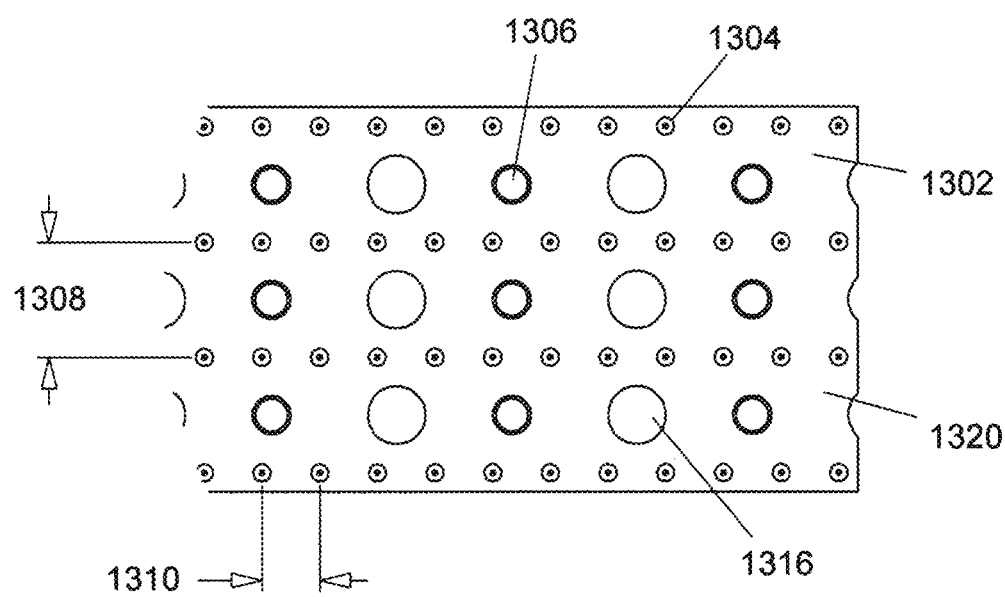
FIG. 71 is an expanded view of the objects of FIG. 70 at location B.
Figure 72:
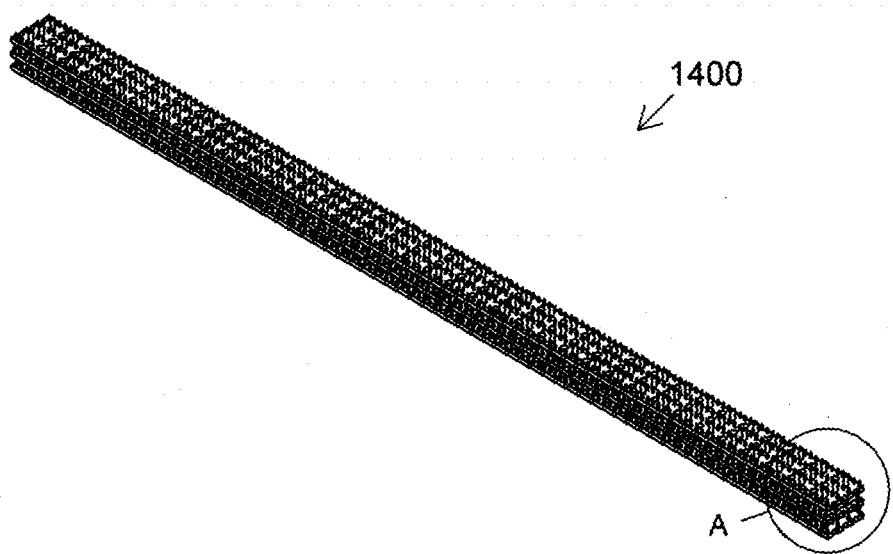
FIG. 72 is an alternate embodiment scaffold formed of lamellae depicted in FIG. 68.
Figure 73:
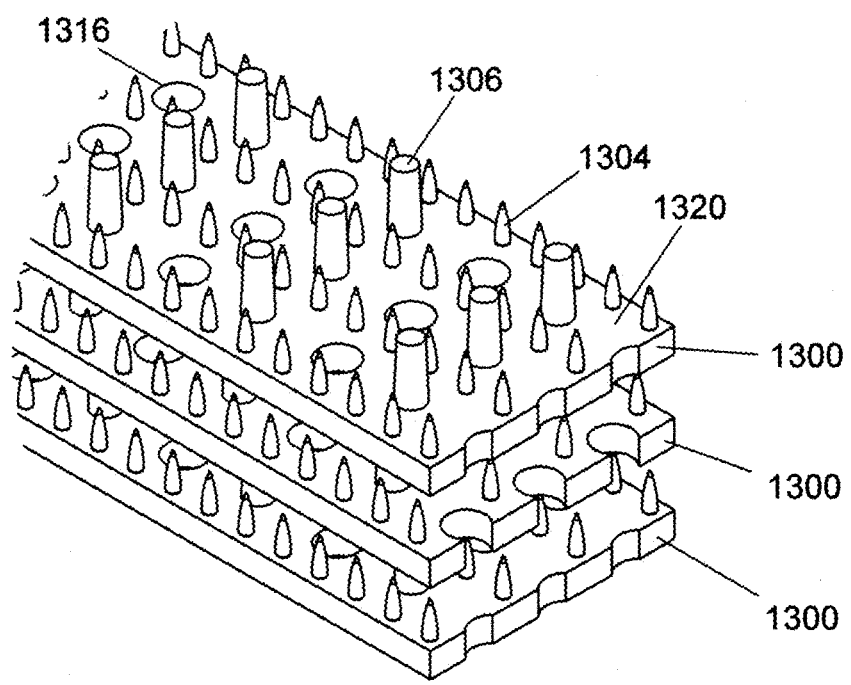
FIG. 73 is an expanded view of the objects of FIG. 72 at location A.
Figure 74:
FIG. 74 is a side elevational view of the objects of FIG. 72.
Figure 75:
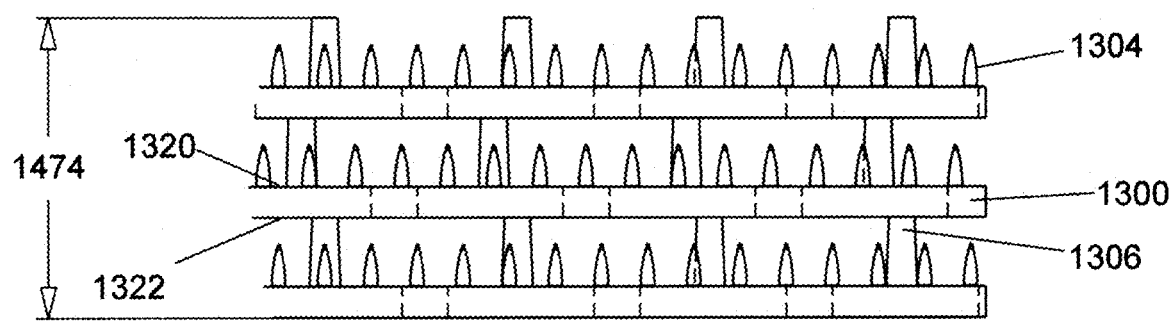
FIG. 75 is an expanded view of the objects of FIG. 74 at location B.

FIG. 59 depicts a scaffold construct 1000 attached at a soft tissue treatment site for the purpose of regenerating or augmenting tissue. Scaffold construct 1000 has spiral wound scaffold 400 (see FIGS. 12 through 14) positioned at the site and secured by bioabsorbable woven element 1002. As depicted, woven element 1002 is affixed at the site by bioabsorbable tissue staples 1004, though any suitable fixation method may be used including suturing. Woven element 1002 prevents movement of scaffold 400 during healing without restricting communication between the biomimetic interlamellar spaces of scaffold 400 and the surrounding environment.

Lamellae previously described for scaffolds of the present invention have formed on them arrays formed of rows of nanofibers with a regular spacing of nanofibers within a row, and with uniform spacing of rows over the first surface of the lamellae. In other scaffold embodiments of the present invention the arrays of nanofibers may have discrete zones in which the array within in each zone is optimized for, for instance, maintaining the stemness of stem cells, or for differentiating stem cells into cells of a preferred type. An illustrative example of a lamella 1100 with an array having two zones is depicted in FIGS. 60 through 63. Lamella 1100 is like lamella 100 (FIGS. 1 through 6) in all aspects of form and function except as specifically hereafter described. Like lamella 100, lamella 1100 is configured to be positioned in a scaffold with the lamellae perpendicular to the base plane of the scaffold. Lamella 1100 has a first array portion with a first spacing between rows 1110, and a second array portion with spacing between rows 1111. Spacing 1110 may be optimized, for instance, for the differentiation of stem cells into osteocytes, while spacing 1111 may be optimized, for instance, for the differentiation of stem cells into chondrocytes. The number and characteristics of the arrays on a lamella may be optimized to create a desired stratified tissue structure.

FIGS. 64 through 67 depicted a lamella 1200 that like lamella 100 is configured for use in a scaffold of the present invention in which lamellae 1200 are perpendicular to the basal plane of the scaffold. Lamella 1200 is identical to lamella 100 in all aspects of form and function except as specifically subsequently described. Lamella 1200 has rows of "hedges" formed of nanofibers spaced distance 1211 apart, the hedges being distance 1210 apart. Distance 1210 is greater than distance 1211. Lamella 1200 has hedges formed of two rows of nanofibers. In other embodiments the hedges may be formed of three or more rows. In some embodiments the spacing of nanofiber rows in a hedge are uniform. In others they are non-uniform, the spacing of the rows in a hedge, and the spacing between hedges being optimized to achieve specific cell behaviors.

In embodiments of mimetic lamellar scaffolds of the present invention previously herein described, the scaffold is implanted in the body of a patient and tissue regeneration occurs within the patient. Scaffolds of the present invention may also be used for the regeneration of tissue external to the patient to create structures for subsequent implantation in the patient. Scaffolds of the present invention have the ability to provide a temporary structure that mimics the extracellular matrix so as to provide a support means and also to affect stem cell behavior to create specific tissue types through the use of biomimetic nanofiber arrays that mimic collagen tendrils.

FIGS. 68 through 71 depict an elongate lamella 1300 for a scaffold for the in vitro growing of an elongate soft tissue structure like a ligament. As depicted, lamella 1300 has a length 1370 and width 1372 suitable for a scaffold of the present invention for creating an ACL for use with aperture fixation, that is, for fixation in the femoral tunnel using an interference screw. Length 1370 is preferably between 120 and 180 millimeters. Width is preferably between six and ten millimeters. Nanofibers positioned distance 1310 apart from rows parallel to the axis of the lamella, the rows being spaced distance 1308 apart. Distances 1308 and 1310 are optimized to cause the growth of ligamentous tissue with cells that favor an axial orientation.

A scaffold 1400 for in vitro growing elongate soft tissue structures is depicted in FIGS. 72 through 75. Scaffold 1400, formed of lamellae 1300 has a height 1474 that is preferably between six and ten millimeters.

In use, scaffold 1400 is placed in a culture vessel containing a culture medium with pluripotent stein cells, preferably bone marrow stromal cells, so that the medium saturates scaffold 1400. Characteristics of the nanofiber arrays of lamellae 1300 cause the preferential differentiation into ligament tissue aligned with the axis of scaffold 1400.

Figure 76:
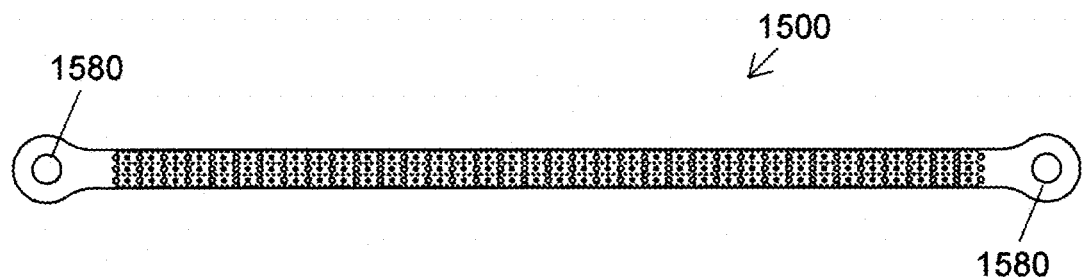
FIG. 76 is a plan view of a lamella for an alternate embodiment scaffold of the present invention for ex vivo growing of an elongate tissue structure.
Figure 77:
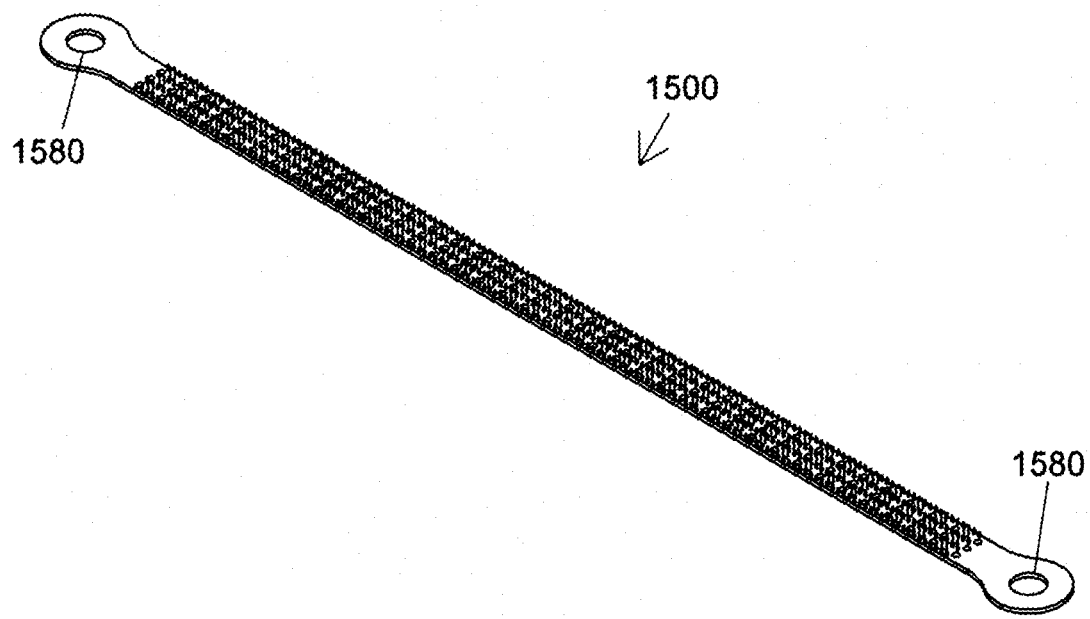
FIG. 77 is a perspective view of the objects of FIG. 76.
Figure 78:
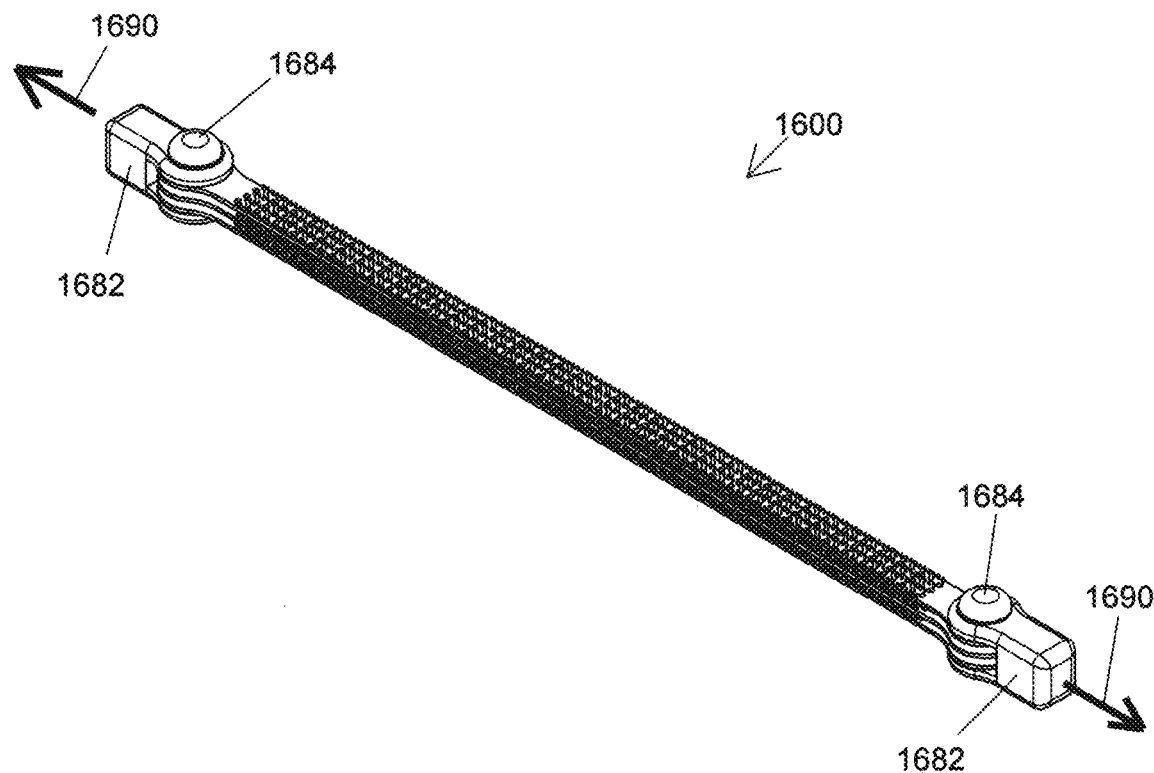
FIG. 78 is a perspective view of an alternate embodiment scaffold of the present invention assembled to means for subjecting the scaffold to a tensile force.
Figure 79:
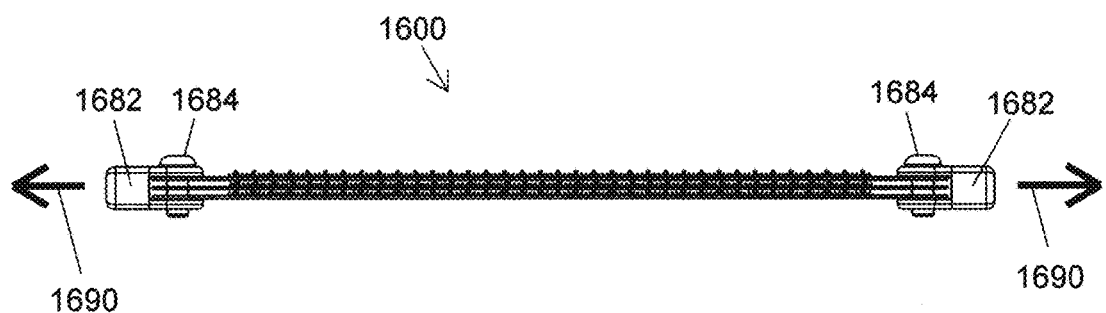
FIG. 79 is a side elevational view of the objects of FIG. 78.
Figure 80:
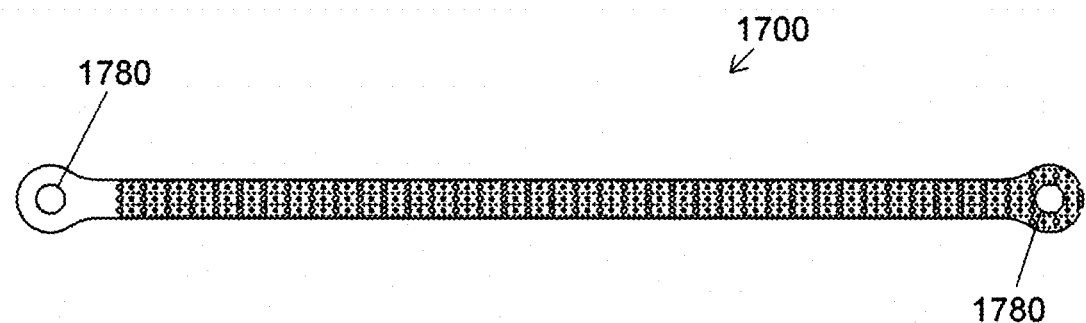
FIG. 80 is a plan view of a lamella for an alternate embodiment scaffold of the present invention configured to produce an ACL graft with an eyelet formed on one end of the graft for fixation.
Figure 81:
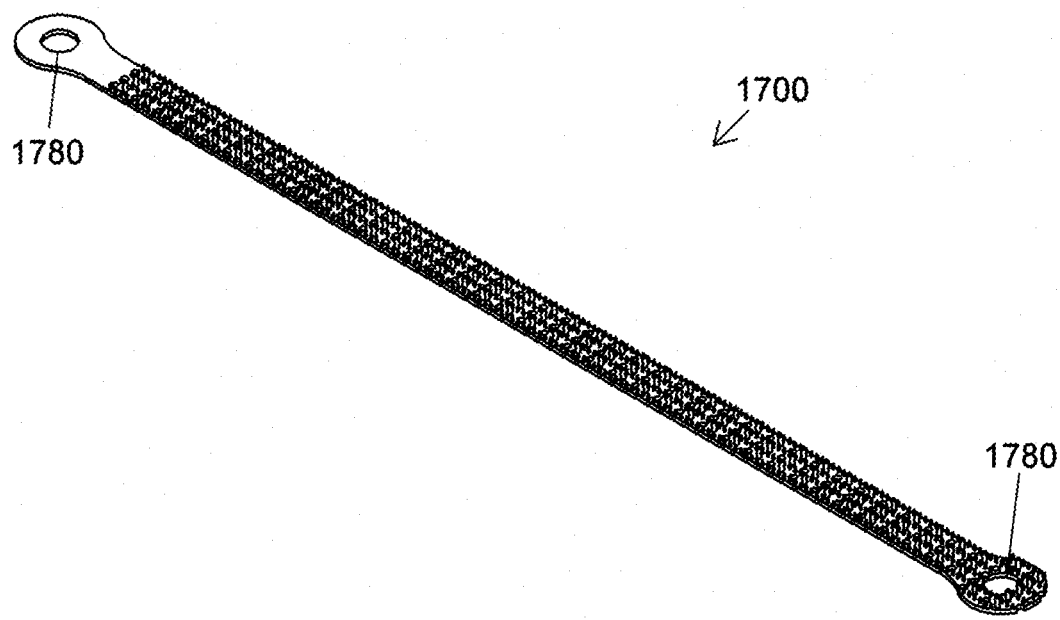
FIG. 81 is a perspective view of the objects of FIG. 80.
Figure 82:
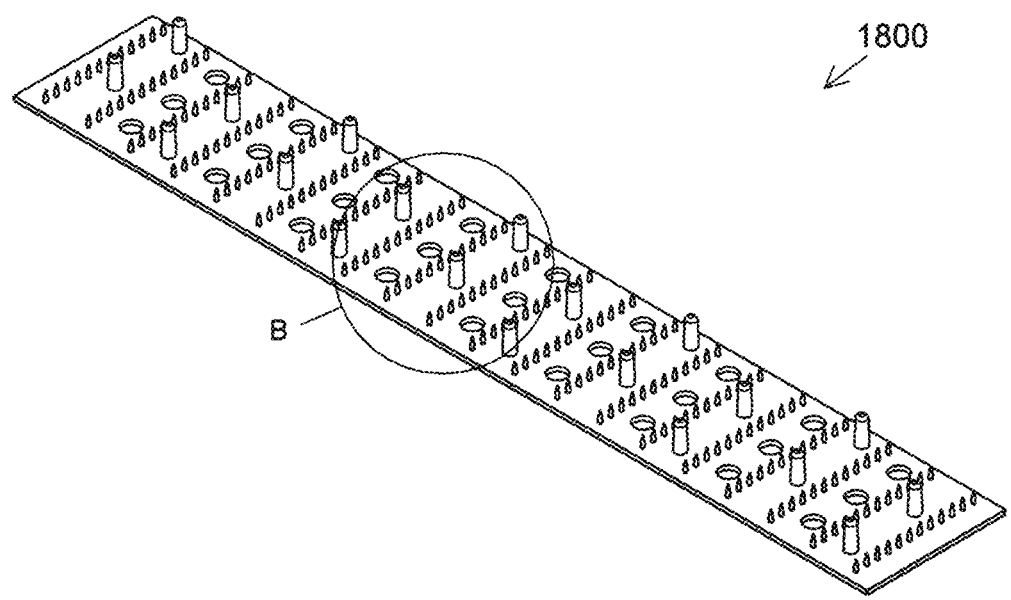
FIG. 82 is a perspective view of a lamella for an alternate embodiment scaffold of the present invention.
Figure 83:
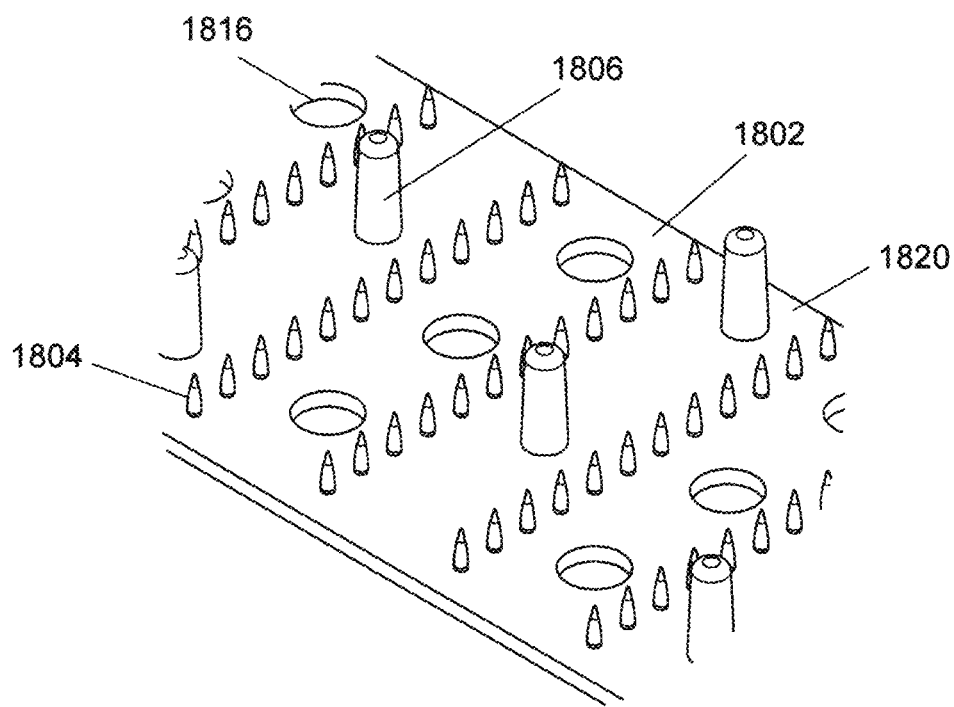
FIG. 83 is an expanded view of the lamella of FIG. 82 at location B.
Figure 84:
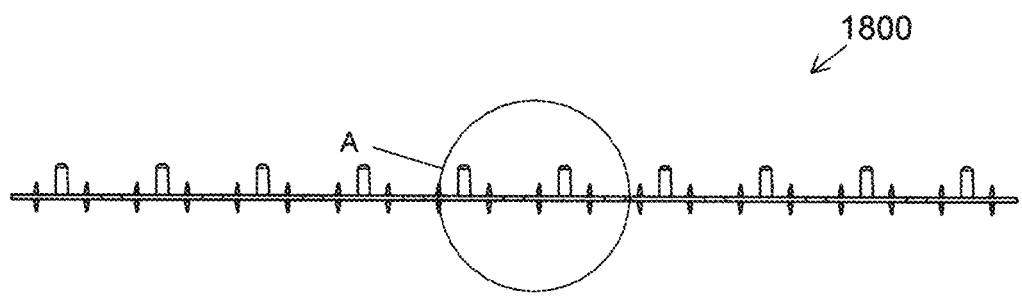
FIG. 84 is a side elevational view of the lamella of FIG. 82.
Figure 85:
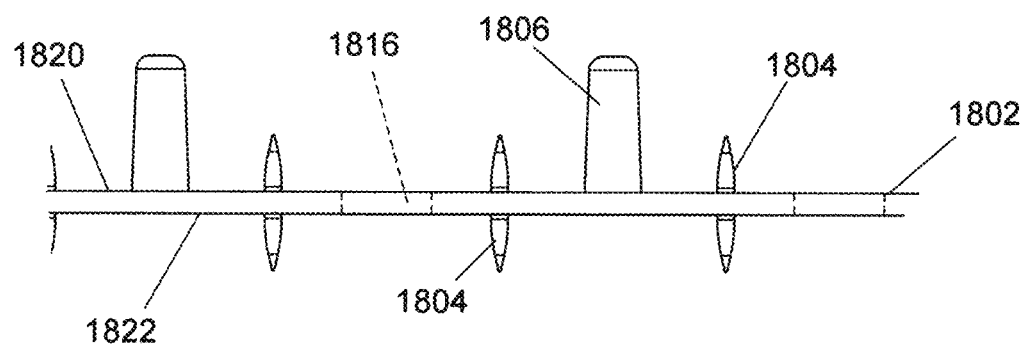
FIG. 85 is an expanded view of the lamella of FIG. 84 at location A.

The differentiation of stem cells into ligament tissue in vitro is strongly affected by loading of the scaffold and developing tissue. Specifically, cyclic tensional or torsional loading like that undergone by a native ACL favors the forming of ligament tissue. FIGS. 76 and 77 depict a lamella 1500 for a lamellar scaffold of the present invention incorporating means for applying a tensile or torsional load to the scaffold. Lamella 1500 is identical in all aspects of form and function to lamella 1300 except as specifically subsequently described. Lamella 1500 has formed at each end an eyelet 1580 through which a tensile force may be applied to lamella 1500. FIGS. 78 and 79 depict scaffold 1600 configured for growing an ACL or similar elongate structure. Lamellae 1500 are stacked and aligned such that links 1682 may be attached to scaffold 1600 using pins 1684 that engage eyelets 1580 of lamellae 1500. The culture vessel into which scaffold 1600 is placed has a means for applying cyclic tensile forces 1690 of predetermined length, force and frequency to scaffold 1600 at suitable times throughout the growth of ligament tissue in scaffold 1600. When formation of the tissue is complete and scaffold 1600 is completely absorbed, the eyelet portions of lamellae 1500 are detached.

A soft tissue graft formed using scaffolds 1400 or 1600 will have a square cross-section. Other scaffolds of the present invention for creating elongate soft tissue grafts have a cylindrical form created by coiling lamellae 1300 or similar. An ACL formed using scaffolds 1400 or 1600 is attached in the usual manner using interference screws or a similar aperture fixation method.

Suspensory fixation of an ACL using an implant commonly referred to as a "button" (for example, the GFS Ultimate by Marcus Medical (Sarasota, Fla.) or similar) requires a longer graft with smaller cross-section. The graft is folded to create a loop through which sutures for engaging the button are passed for femoral fixation. The dimensions of scaffold 1600 may be modified to create this longer thinner ligament. Alternatively, an ACL may be formed with features that enable easy secure fixation at implantation. A lamella 1700 for a lamellar scaffold of the present invention is configured for growing an "improved" ACL configured for increased ease of suspensory femoral fixation. Lamella 1700 is identical to lamella 1500 in al aspects of form and function except as specifically hereafter described. The nanofiber array, pedestals and perforations of lamella 1500 are extended to so as to cover the surface surrounding eyelet 1780 at a first end of lamella 1700. An ACL grown using a lamellar matrix formed of lamellae 1700 will have an eyelet portion configured like the eyelet portion of lamellae 1500 and 1700 when viewed in a plan view. Suture may be threaded through the loop for suspensory fixation. Alternatively, a larger diameter tunnel may be formed with the graft extending through the tunnel so that the eyelet may be secured to the anterior surface of the femur using a washer and screw, staple or another mechanical fixation.

The ability of scaffolds of the present invention to affect the differentiation of stein cells through the configuration of nanofiber arrays formed on lamellae that make up the scaffold enable the forming of ACL and other elongate tissue structures with advanced features. For instance, a commonly used ACL graft type is a bone-tendon-bone (BTB) patellar tendon graft. The BTB graft has a bone portion attached to each end of the graft so that fixation during graft placement is achieved by affixing the bone blocks to the femur and tibia. A BTB may grown in vitro using scaffolds of the present invention made of lamellae like 1600, but with the nanofiber array having three zones, a first central zone wherein the nanofiber array characteristics are optimized for the growth of ligament tissue, and two end zones wherein the nanofiber array characteristics are optimized for the growth of bone. Additionally, the developing graft may be subjected to appropriate compressive, torsional and tensile stresses to encourage development of the desired tissue types.

Figure 86:
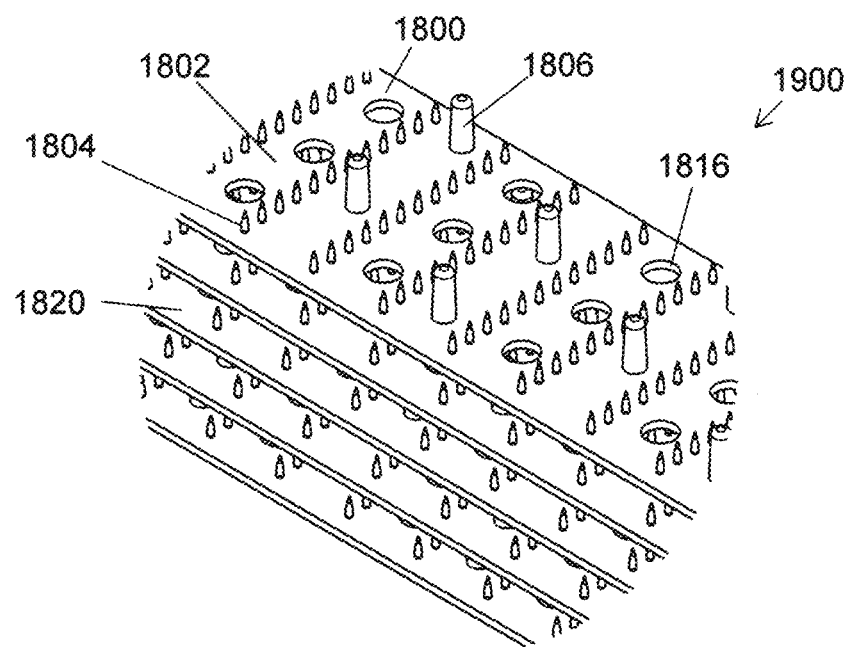
FIG. 86 is a perspective view of a portion of an alternate embodiment scaffold of the present invention formed from lamellas of FIG. 82.
Figure 87:
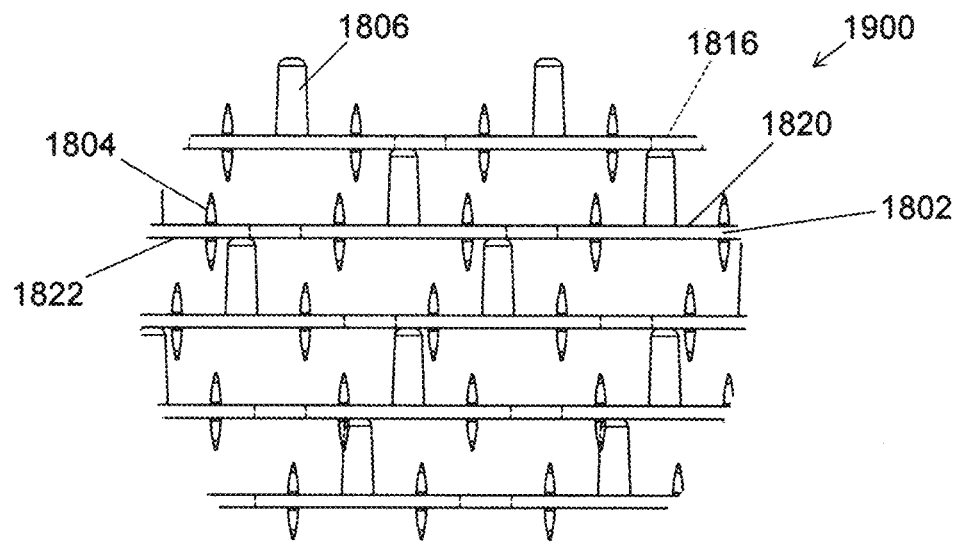
FIG. 87 is a side elevational view of the scaffold portion of FIG. 86.

In embodiments previously herein described lamellae forming scaffolds of the present invention have nanofiber arrays formed on a first surface of a lamella only. In other embodiments of the present invention, nanofiber arrays may be formed on both first and second opposed surfaces of the lamella with the nanofibers from both surfaces extending into the interlamellar spaces. FIGS. 82 through 85 depict a representative lamella 1800 for a scaffold of the present invention identical in all aspects of form and function to lamella 100 (FIGS. 1 to 6) except as specifically hereafter described. Lamella 1800 has arrays of nanofibers 1804 formed on both first surface 1820 and second surface 1822 of planar portion 1802. Referring now to FIGS. 86 and 87, scaffold portion 1900 formed of lamellas 1800 has formed therein interlamellar spaces in which nanofibers 1804 formed on the first and second surfaces 1820 and 1822 of adjacent lamellas 1800 both protrude into the interlamellar space. In all other aspects scaffold portion 1900 is alike in form and function to scaffolds previously herein described.

This description and appended claims include the words "below", "above", "side", "top", "bottom", "upper", "lower", "when", "upright", etc. to provide an orientation of embodiments of the invention to allow for proper description of example embodiments. The foregoing positional terms refer to the apparatus when in the orientation shown in FIG. 1. A person of skill in the art will recognize that the apparatus can assume different orientations when in use. It is also contemplated that embodiments of the invention may be in orientations other than upright without departing from the spirit and scope of the invention as set forth in the appended claims. Further, it is contemplated that "above" means having an elevation greater than, and "below" means having an elevation less than such that one part need not be directly over or directly under another part to be within the scope of "above" or "below" as used herein.

The phrase "in one embodiment," as used herein does not necessarily refer to the same embodiment, although it may. Conditional language used herein, such as, among others, "can", "might", "may", "e.g.," and the like, unless specifically stated otherwise, or otherwise understood within the context as used, is generally intended to convey that certain embodiments include, while other embodiments do not include, certain features, elements and/or states.

Although embodiments of the present invention have been described in detail, it will be understood by those skilled in the art that various modifications can be made therein without departing from the spirit and scope of the invention as set forth in the appended claims.

This written description uses examples to disclose the invention and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

It will be understood that the particular embodiments described herein are shown by way of illustration and not as limitations of the invention. The principal features of this invention may be employed in various embodiments without departing from the scope of the invention. Those of ordinary skill in the art will recognize numerous equivalents to the specific procedures described herein. Such equivalents are considered to be within the scope of this invention and are covered by the claims.

All of the compositions and/or methods disclosed and claimed herein may be made and/or executed without undue experimentation in light of the present disclosure. While the compositions and methods of this invention have been described in terms of the embodiments included herein, it will be apparent to those of ordinary skill in the art that variations may be applied to the compositions and/or methods and in the steps or in the sequence of steps of the method described herein without departing from the concept, spirit, and scope of the invention. All such similar substitutes and modifications apparent to those skilled in the art are deemed to be within the spirit, scope, and concept of the invention as defined by the appended claims.

Thus, although there have been described particular embodiments of the present invention, it is not intended that such references be construed as limitations upon the scope of this invention except as set forth in the following

What is claimed is:

1. A lamellar scaffold for tissue regeneration, comprising:
    a plurality of lamellae oriented substantially perpendicular to a basal plane of the scaffold, each lamella of the plurality formed of a polymer film including a first surface and a second surface, the first surface having a patterned array of tapered polymer nanofibers protruding therefrom, the second surface having no nanofibers;
    a plurality of interlamellar spaces formed between the first and second surfaces of adjacent lamellae; and
    a plurality of protuberances formed on the lamellae to maintain the interlamellar spaces;
    wherein the patterned array of tapered polymer nanofibers on the first surface of each lamella protrudes into an adjacent interlamellar space and is configured to influence the propagation and differentiation of cells populated to or recruited to the scaffold;
    wherein the tapered polymer nanofibers have a basal diameter of from about 0.1 to about 0.8 microns and a length of from about 10 to about 100 microns; and
    wherein the basal plane of the scaffold is defined by a bottom surface of the scaffold.

2. The lamellar scaffold of claim 1, wherein the bottom surface of the scaffold is configured to be placed adjacent to a surface of a tissue in need of regeneration.

3. The lamellar scaffold of claim 2, wherein adjacent to a surface of a tissue in need of regeneration is substantially parallel to a surface of a tissue in need of regeneration.

4. The lamellar scaffold of claim 1, wherein the patterned array of tapered polymer nanofibers protrudes from the first surface at an angle substantially normal to the first surface.

5. The lamellar scaffold of claim 1, wherein the lamellae further comprise perforations between the first surface and the second surface.

6. The lamellar scaffold of claim 1, wherein the polymer film is bioabsorbable.

7. The lamellar scaffold of claim 1, wherein the polymer film is treated with another polymer or a biological substance to improve surface wetting and cell attachment.

8. The lamellar scaffold of claim 7, wherein the polymer film is treated with poly-L-lysine, poly-D-lysine, a proteoglycan, or a glycoprotein.

9. The lamellar scaffold of claim 1, wherein the lamellae are arranged in a substantially parallel configuration with the first surface of each lamella adjacent to the second surface of its adjacent lamella.

10. The lamellar scaffold of claim 1, wherein the lamellae are arranged in a concentric spiral.

11. The lamellar scaffold of claim 1, wherein the patterned array of tapered nanofibers comprises rows of nanofibers.

12. The lamellar scaffold of claim 1, wherein the patterned array of tapered nanofibers is substantially uniform over the first surface of each lamella.

13. The lamellar scaffold of claim 1, wherein the first surface of each lamella includes a first region with a first patterned array of tapered nanofibers, and a second region with a second patterned array of tapered nanofibers that is different from the first pattered array of tapered nanofibers.

14. A lamellar scaffold for tissue regeneration, comprising:
    a plurality of lamellae oriented substantially perpendicular to a bottom surface of the scaffold, each lamella of the plurality formed of a polymer film including a first surface and a second surface, the first surface having a patterned array of tapered polymer nanofibers protruding therefrom, the second surface having no nanofibers;

a plurality of interlamellar spaces formed between the first and second surfaces of adjacent lamellae; and a plurality of protuberances formed on the lamellae to maintain the interlamellar spaces;

wherein the patterned array of tapered polymer nanofibers on the first surface of each lamella protrudes into an adjacent interlamellar space and is configured to influence the propagation and differentiation of cells populated to or recruited to the scaffold;

wherein the tapered polymer nanofibers have a basal diameter of from about 0.1 to about 0.8 microns and a length of from about 10 to about 100 microns; and wherein the protuberances have a diameter greater than the diameter of the tapered polymer nanofibers.

15. The lamellar scaffold of claim 14, wherein the bottom surface of the scaffold is configured to be placed adjacent to a surface of a tissue in need of regeneration.

16. The lamellar scaffold of claim 15, wherein adjacent to a surface of a tissue in need of regeneration is substantially parallel to a surface of a tissue in need of regeneration.

17. The lamellar scaffold of claim 14, wherein a basal portion of substantially each tapered polymer nanofiber protrudes at an angle substantially perpendicular to the first surface.

18. A lamellar scaffold for tissue regeneration, comprising:

a plurality of lamellae oriented substantially perpendicular to a surface of a tissue in need of regeneration, each lamella of the plurality formed of a polymer film including a first surface and a second surface, the first surface having a patterned array of tapered polymer nanofibers protruding therefrom, the second surface having no nanofibers;

a plurality of interlamellar spaces formed between the first and second surfaces of adjacent lamellae; and a plurality of protuberances formed on the lamellae to maintain the interlamellar spaces;

wherein the patterned array of tapered polymer nanofibers on the first surface of each lamella protrudes into an adjacent interlamellar space and is configured to influence the propagation and differentiation of cells populated to or recruited to the scaffold; and wherein the tapered polymer nanofibers have a basal diameter of from about 0.1 to about 0.8 microns and a length of from about 10 to about 100 microns.

19. The lamellar scaffold of claim 18, wherein the plurality of lamellae are arranged in a substantially parallel configuration with the first surface of each lamella adjacent to the second surface of its adjacent lamella.

20. The lamellar scaffold of claim 18, wherein the scaffold includes a bottom surface;

the plurality of lamellae are oriented substantially perpendicular to the bottom surface; and the bottom surface is configured to be placed substantially parallel to the surface of the tissue in need of regeneration.

* * * * *